United States Patent
Tegels et al.

(10) Patent No.: US 10,470,877 B2
(45) Date of Patent: Nov. 12, 2019

(54) APPARATUS AND METHODS FOR ANTERIOR VALVE LEAFLET MANAGEMENT

(71) Applicant: Tendyne Holdings, Inc., Roseville, MN (US)

(72) Inventors: Zachary J. Tegels, Minneapolis, MN (US); Michael J. Urick, Chaska, MN (US)

(73) Assignee: Tendyne Holdings, Inc., St. Paul, MN (US)

( * ) Notice: Subject to any disclaimer, the term of this patent is extended or adjusted under 35 U.S.C. 154(b) by 329 days.

(21) Appl. No.: 15/499,129

(22) Filed: Apr. 27, 2017

(65) Prior Publication Data

US 2017/0319333 A1    Nov. 9, 2017

Related U.S. Application Data

(60) Provisional application No. 62/331,235, filed on May 3, 2016.

(51) Int. Cl.
    *A61F 2/24*       (2006.01)
    *A61B 18/14*      (2006.01)
    (Continued)

(52) U.S. Cl.
    CPC ........ *A61F 2/2409* (2013.01); *A61B 17/0401* (2013.01); *A61B 18/1492* (2013.01);
    (Continued)

(58) Field of Classification Search
    CPC ........ A61B 2018/00369; A61F 2/2427; A61F 2/243; A61F 2/2433; A61F 2/2436;
    (Continued)

(56) References Cited

U.S. PATENT DOCUMENTS 2,697,008 A    12/1954   Rowley
3,409,013 A    11/1968   Berry
(Continued)

FOREIGN PATENT DOCUMENTS

CN    1486161        3/2004
CN    1961845 A      5/2007
(Continued)

OTHER PUBLICATIONS

US 9,155,620 B2, 10/2015, Gross et al. (withdrawn)
(Continued)

*Primary Examiner* — Gregory A Anderson
(74) *Attorney, Agent, or Firm* — Lerner, David, Littenberg, Krumholz & Mentlik, LLP

(57) ABSTRACT

In some embodiments, a method includes delivering to a native valve annulus (e.g., a native mitral valve annulus) of a heart a prosthetic heart valve having a body expandable from a collapsed, delivery configuration to an expanded, deployed configuration. The method can further include, after the delivering, causing the prosthetic heart valve to move from the delivery configuration to the deployed configuration. With the prosthetic heart valve in its deployed configuration, an anchor can be delivered and secured to at least one of a fibrous trigone of the heart or an anterior native leaflet of the native valve. With the prosthetic heart valve disposed in the native valve annulus and in its deployed configuration, an anchoring tether can extending from the anchor can be secured to a wall of the heart to urge the anterior native leaflet towards the body of the prosthetic heart valve.

9 Claims, 32 Drawing Sheets

(51) Int. Cl.
  *A61B 17/04* (2006.01)
  *A61B 18/00* (2006.01)
  *A61B 17/064* (2006.01)

(52) U.S. Cl.
  CPC .......... *A61F 2/2418* (2013.01); *A61F 2/2427* (2013.01); *A61F 2/2457* (2013.01); *A61B 2017/0417* (2013.01); *A61B 2017/0649* (2013.01); *A61B 2018/00369* (2013.01); *A61B 2018/00619* (2013.01); *A61F 2/2445* (2013.01); *A61F 2250/001* (2013.01); *A61F 2250/0006* (2013.01); *A61F 2250/0063* (2013.01)

(58) Field of Classification Search
  CPC .... A61F 2/2439; A61F 2/2454; A61F 2/2457; A61F 2/246; A61F 2/2463; A61F 2/2466
  See application file for complete search history.

(56) References Cited

U.S. PATENT DOCUMENTS

| | | |
|---|---|---|
| 3,472,230 A | 10/1969 | Fogarty et al. |
| 3,476,101 A | 11/1969 | Ross |
| 3,548,417 A | 12/1970 | Kisher |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,976,079 A | 8/1976 | Samuels et al. |
| 4,003,382 A | 1/1977 | Dyke |
| 4,035,849 A | 7/1977 | Angell et al. |
| 4,056,854 A | 11/1977 | Boretos et al. |
| 4,073,438 A | 2/1978 | Meyer |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,490,859 A | 1/1985 | Black et al. |
| 4,535,483 A | 8/1985 | Klawitter et al. |
| 4,574,803 A | 3/1986 | Storz |
| 4,585,705 A | 4/1986 | Broderick et al. |
| 4,592,340 A | 6/1986 | Boyles |
| 4,605,407 A | 8/1986 | Black et al. |
| 4,612,011 A | 9/1986 | Kautzky |
| 4,626,255 A | 12/1986 | Reichart et al. |
| 4,638,886 A | 1/1987 | Marietta |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,824,180 A | 4/1989 | Levrai |
| 4,829,990 A | 5/1989 | Thuroff et al. |
| 4,830,117 A | 5/1989 | Capasso |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,923,013 A | 5/1990 | De Gennaro |
| 4,960,424 A | 10/1990 | Grooters |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 4,996,873 A | 3/1991 | Takeuchi |
| 5,007,896 A | 4/1991 | Shiber |
| 5,026,366 A | 6/1991 | Leckrone |
| 5,032,128 A | 7/1991 | Alonso |
| 5,035,706 A | 7/1991 | Giantureo et al. |
| 5,037,434 A | 8/1991 | Lane |
| 5,047,041 A | 9/1991 | Sammuels |
| 5,059,177 A | 10/1991 | Towne et al. |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,201,880 A | 4/1993 | Wright et al. |
| 5,266,073 A | 11/1993 | Wall |
| 5,282,847 A | 2/1994 | Trescony et al. |
| 5,295,958 A | 3/1994 | Shturman |
| 5,306,296 A | 4/1994 | Wright et al. |
| 5,332,402 A | 7/1994 | Teitelbaum |
| 5,336,616 A | 8/1994 | Livesey et al. |
| 5,344,442 A | 9/1994 | Deac |
| 5,360,444 A | 11/1994 | Kusuhara |
| 5,364,407 A | 11/1994 | Poll |
| 5,370,685 A | 12/1994 | Stevens |
| 5,397,351 A | 3/1995 | Pavcnik et al. |
| 5,411,055 A | 5/1995 | Kane et al. |
| 5,411,552 A | 5/1995 | Andersen et al. |
| 5,415,667 A | 5/1995 | Frater |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,184 A | 9/1996 | Machiraju |
| 5,554,185 A | 9/1996 | Block et al. |
| 5,571,175 A | 11/1996 | Vanney et al. |
| 5,591,185 A | 1/1997 | Kilmer et al. |
| 5,607,462 A | 3/1997 | Imran |
| 5,607,464 A | 3/1997 | Trescony et al. |
| 5,609,626 A | 3/1997 | Quijano et al. |
| 5,639,274 A | 6/1997 | Fischell et al. |
| 5,662,704 A | 9/1997 | Gross |
| 5,665,115 A | 9/1997 | Cragg |
| 5,674,279 A | 10/1997 | Wright et al. |
| 5,697,905 A | 12/1997 | Ambrosio |
| 5,702,368 A | 12/1997 | Stevens et al. |
| 5,716,417 A | 2/1998 | Girard et al. |
| 5,728,068 A | 3/1998 | Leone et al. |
| 5,728,151 A | 3/1998 | Garrison et al. |
| 5,735,842 A | 4/1998 | Krueger et al. |
| 5,741,333 A | 4/1998 | Frid |
| 5,749,890 A | 5/1998 | Shaknovich |
| 5,756,476 A | 5/1998 | Epstein |
| 5,769,812 A | 6/1998 | Stevens et al. |
| 5,792,179 A | 8/1998 | Sideris |
| 5,800,508 A | 9/1998 | Goicoechea et al. |
| 5,833,673 A | 11/1998 | Ockuly et al. |
| 5,840,081 A | 11/1998 | Andersen et al. |
| 5,855,597 A | 1/1999 | Jayaraman |
| 5,855,601 A | 1/1999 | Bessler |
| 5,855,602 A | 1/1999 | Angell |
| 5,904,697 A | 5/1999 | Gifford, III et al. |
| 5,925,063 A | 7/1999 | Khosravi |
| 5,957,949 A | 9/1999 | Leonhardt et al. |
| 5,968,052 A | 10/1999 | Sullivan, III et al. |
| 5,968,068 A | 10/1999 | Dehdashtian et al. |
| 5,972,030 A | 10/1999 | Garrison et al. |
| 5,993,481 A | 11/1999 | Marcade et al. |
| 6,027,525 A | 2/2000 | Suh et al. |
| 6,042,607 A | 3/2000 | Williamson, IV et al. |
| 6,045,497 A | 4/2000 | Schweich, Jr. et al. |

(56) References Cited

U.S. PATENT DOCUMENTS

| | | |
|---|---|---|
| 6,063,112 A | 5/2000 | Sgro et al. |
| 6,077,214 A | 6/2000 | Mortier et al. |
| 6,099,508 A | 8/2000 | Bousquet |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,183,411 B1 | 2/2001 | Mortier et al. |
| 6,210,408 B1 | 4/2001 | Chandrasakaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,287,339 B1 | 9/2001 | Vazquez et al. |
| 6,299,637 B1 | 10/2001 | Shaolian |
| 6,302,906 B1 | 10/2001 | Goecoechea et al. |
| 6,312,465 B1 | 11/2001 | Griffin et al. |
| 6,332,893 B1 | 12/2001 | Mortier et al. |
| 6,350,277 B1 | 2/2002 | Kocur |
| 6,358,277 B1 | 3/2002 | Duran |
| 6,379,372 B1 | 4/2002 | Dehdashtian et al. |
| 6,402,679 B1 | 6/2002 | Mortier et al. |
| 6,402,680 B2 | 6/2002 | Mortier et al. |
| 6,402,781 B1 | 6/2002 | Langberg et al. |
| 6,406,420 B1 | 6/2002 | McCarthy et al. |
| 6,425,916 B1 | 7/2002 | Garrison et al. |
| 6,440,164 B1 | 8/2002 | Di Matteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,537,198 B1 | 3/2003 | Vidlund et al. |
| 6,540,782 B1 | 4/2003 | Snyders |
| 6,569,196 B1 | 5/2003 | Vesely et al. |
| 6,575,252 B2 | 6/2003 | Reed |
| 6,582,462 B1 | 6/2003 | Andersen et al. |
| 6,605,112 B1 | 8/2003 | Moll |
| 6,616,684 B1 | 9/2003 | Vidlund et al. |
| 6,622,730 B2 | 9/2003 | Ekvall et al. |
| 6,629,534 B1 | 10/2003 | St. Goar et al. |
| 6,629,921 B1 | 10/2003 | Schweich, Jr. et al. |
| 6,648,077 B2 | 11/2003 | Hoffman |
| 6,648,921 B2 | 11/2003 | Anderson et al. |
| 6,652,578 B2 | 11/2003 | Bailey et al. |
| 6,669,724 B2 | 12/2003 | Park et al. |
| 6,706,065 B2 | 3/2004 | Langberg et al. |
| 6,709,456 B2 | 3/2004 | Langberg et al. |
| 6,723,038 B1 | 4/2004 | Schroeder et al. |
| 6,726,715 B2 | 4/2004 | Sutherland |
| 6,730,118 B2 | 5/2004 | Spenser et al. |
| 6,733,525 B2 | 5/2004 | Yang et al. |
| 6,740,105 B2 | 5/2004 | Yodfat et al. |
| 6,746,401 B2 | 6/2004 | Panescu |
| 6,746,471 B2 | 6/2004 | Mortier et al. |
| 6,752,813 B2 | 6/2004 | Goldfarb et al. |
| 6,764,510 B2 | 7/2004 | Vidlund et al. |
| 6,797,002 B2 | 9/2004 | Spence et al. |
| 6,810,882 B2 | 11/2004 | Langberg et al. |
| 6,830,584 B1 | 12/2004 | Seguin |
| 6,854,668 B2 | 2/2005 | Wancho et al. |
| 6,855,144 B2 | 2/2005 | Lesh |
| 6,858,001 B1 | 2/2005 | Aboul-Hosn |
| 6,890,353 B2 | 5/2005 | Cohn et al. |
| 6,893,460 B2 | 5/2005 | Spenser et al. |
| 6,896,690 B1 | 5/2005 | Lambrecht et al. |
| 6,908,424 B2 | 6/2005 | Mortier et al. |
| 6,908,481 B2 | 6/2005 | Cribier |
| 6,936,067 B2 | 8/2005 | Buchanan |
| 6,945,996 B2 | 9/2005 | Sedransk |
| 6,955,175 B2 | 10/2005 | Stevens et al. |
| 6,974,476 B2 | 12/2005 | McGuckin et al. |
| 6,976,543 B1 | 12/2005 | Fischer |
| 6,997,950 B2 | 2/2006 | Chawla |
| 7,018,406 B2 | 3/2006 | Seguin et al. |
| 7,018,408 B2 | 3/2006 | Bailey et al. |
| 7,044,905 B2 | 5/2006 | Vidlund et al. |
| 7,060,021 B1 | 6/2006 | Wilk |
| 7,077,862 B2 | 7/2006 | Vidlund et al. |
| 7,087,064 B1 | 8/2006 | Hyde |
| 7,100,614 B2 | 9/2006 | Stevens et al. |
| 7,101,395 B2 | 9/2006 | Tremulis et al. |
| 7,108,717 B2 | 9/2006 | Freidberg |
| 7,112,219 B2 | 9/2006 | Vidlund et al. |
| 7,115,141 B2 | 10/2006 | Menz et al. |
| 7,141,064 B2 | 11/2006 | Scott et al. |
| 7,175,656 B2 | 2/2007 | Khairkhahan |
| 7,198,646 B2 | 4/2007 | Figulla et al. |
| 7,201,772 B2 | 4/2007 | Schwammenthal et al. |
| 7,247,134 B2 | 7/2007 | Vidlund et al. |
| 7,252,682 B2 | 8/2007 | Seguin |
| 7,267,686 B2 | 9/2007 | DiMatteo et al. |
| 7,275,604 B1 | 10/2007 | Wall |
| 7,276,078 B2 | 10/2007 | Spenser et al. |
| 7,276,084 B2 | 10/2007 | Yang et al. |
| 7,316,706 B2 | 1/2008 | Bloom et al. |
| 7,318,278 B2 | 1/2008 | Zhang et al. |
| 7,326,236 B2 | 2/2008 | Andreas et al. |
| 7,329,278 B2 | 2/2008 | Seguin et al. |
| 7,331,991 B2 | 2/2008 | Kheradvar et al. |
| 7,335,213 B1 | 2/2008 | Hyde et al. |
| 7,374,571 B2 | 5/2008 | Pease et al. |
| 7,377,941 B2 | 5/2008 | Rhee et al. |
| 7,381,210 B2 | 6/2008 | Zarbatany et al. |
| 7,381,218 B2 | 6/2008 | Schreck |
| 7,393,360 B2 | 7/2008 | Spenser et al. |
| 7,404,824 B1 | 7/2008 | Webler et al. |
| 7,416,554 B2 | 8/2008 | Lam et al. |
| 7,422,072 B2 | 9/2008 | Dade |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,470,285 B2 | 12/2008 | Nugent et al. |
| 7,500,989 B2 | 3/2009 | Solem et al. |
| 7,503,931 B2 | 3/2009 | Kowalsky et al. |
| 7,510,572 B2 | 3/2009 | Gabbay |
| 7,510,575 B2 | 3/2009 | Spenser et al. |
| 7,513,908 B2 | 4/2009 | Lattouf |
| 7,524,330 B2 | 4/2009 | Berreklouw |
| 7,527,647 B2 | 5/2009 | Spence |
| 7,534,260 B2 | 5/2009 | Lattouf |
| 7,556,646 B2 | 7/2009 | Yang et al. |
| 7,579,381 B2 | 8/2009 | Dove |
| 7,585,321 B2 | 9/2009 | Cribier |
| 7,591,847 B2 | 9/2009 | Navia et al. |
| 7,618,446 B2 | 11/2009 | Andersen et al. |
| 7,618,447 B2 | 11/2009 | Case et al. |
| 7,621,948 B2 | 11/2009 | Herrmann et al. |
| 7,632,304 B2 | 12/2009 | Park |
| 7,632,308 B2 | 12/2009 | Loulmet |
| 7,635,386 B1 | 12/2009 | Gammie |
| 7,674,222 B2 | 3/2010 | Nikolic et al. |
| 7,674,286 B2 | 3/2010 | Alfieri et al. |
| 7,695,510 B2 | 4/2010 | Bloom et al. |
| 7,708,775 B2 | 5/2010 | Rowe et al. |
| 7,748,389 B2 | 7/2010 | Salahieh et al. |
| 7,766,961 B2 | 8/2010 | Patel et al. |
| 7,789,909 B2 | 9/2010 | Andersen et al. |
| 7,803,168 B2 | 9/2010 | Gifford et al. |
| 7,803,184 B2 | 9/2010 | McGuckin, Jr. et al. |
| 7,803,185 B2 | 9/2010 | Gabbay |
| 7,806,928 B2 | 10/2010 | Rowe et al. |
| 7,837,727 B2 | 11/2010 | Goetz et al. |
| 7,854,762 B2 | 12/2010 | Speziali et al. |
| 7,892,281 B2 | 2/2011 | Seguin et al. |
| 7,896,915 B2 | 3/2011 | Guyenot et al. |
| 7,901,454 B2 | 3/2011 | Kapadia et al. |
| 7,927,370 B2 | 4/2011 | Webler et al. |
| 7,931,630 B2 | 4/2011 | Nishtala et al. |

(56) References Cited

U.S. PATENT DOCUMENTS

| | | |
|---|---|---|
| 7,942,928 B2 | 5/2011 | Webler et al. |
| 7,955,247 B2 | 6/2011 | Levine et al. |
| 7,955,385 B2 | 6/2011 | Crittenden |
| 7,972,378 B2 | 7/2011 | Tabor et al. |
| 7,988,727 B2 | 8/2011 | Santamore et al. |
| 7,993,394 B2 | 8/2011 | Hariton et al. |
| 8,007,992 B2 | 8/2011 | Tian et al. |
| 8,029,556 B2 | 10/2011 | Rowe |
| 8,043,368 B2 | 10/2011 | Crabtree |
| 8,052,749 B2 | 11/2011 | Salahieh |
| 8,052,750 B2 | 11/2011 | Tuval et al. |
| 8,052,751 B2 | 11/2011 | Aklog et al. |
| 8,062,355 B2 | 11/2011 | Figulla et al. |
| 8,062,359 B2 | 11/2011 | Marquez et al. |
| 8,070,802 B2 | 12/2011 | Lamphere et al. |
| 8,109,996 B2 | 2/2012 | Stacchino et al. |
| 8,142,495 B2 | 3/2012 | Hasenkam et al. |
| 8,152,821 B2 | 4/2012 | Gambale et al. |
| 8,157,810 B2 | 4/2012 | Case et al. |
| 8,167,932 B2 | 5/2012 | Bourang et al. |
| 8,167,934 B2 | 5/2012 | Styrc et al. |
| 8,187,299 B2 | 5/2012 | Goldfarb et al. |
| 8,206,439 B2 | 6/2012 | Gomez Duran |
| 8,216,301 B2 | 7/2012 | Bonhoeffer et al. |
| 8,226,711 B2 | 7/2012 | Mortier et al. |
| 8,236,045 B2 | 8/2012 | Benichou et al. |
| 8,241,274 B2 | 8/2012 | Keogh et al. |
| 8,252,051 B2 | 8/2012 | Chau et al. |
| 8,303,653 B2 | 11/2012 | Bonhoeffer et al. |
| 8,308,796 B2 | 11/2012 | Lashinski et al. |
| 8,323,334 B2 | 12/2012 | Deem et al. |
| 8,353,955 B2 | 1/2013 | Styrc et al. |
| RE44,075 E | 3/2013 | Williamson et al. |
| 8,449,599 B2 | 5/2013 | Chau et al. |
| 8,454,656 B2 | 6/2013 | Tuval |
| 8,470,028 B2 | 6/2013 | Thornton et al. |
| 8,480,730 B2 | 7/2013 | Maurer et al. |
| 8,486,138 B2 | 7/2013 | Vesely |
| 8,506,623 B2 | 8/2013 | Wilson et al. |
| 8,506,624 B2 | 8/2013 | Vidlund et al. |
| 8,578,705 B2 | 11/2013 | Sindano et al. |
| 8,579,913 B2 | 11/2013 | Nielsen |
| 8,591,573 B2 | 11/2013 | Barone |
| 8,591,576 B2 | 11/2013 | Hasenkam et al. |
| 8,597,347 B2 | 12/2013 | Maurer et al. |
| 8,685,086 B2 | 4/2014 | Navia et al. |
| 8,790,394 B2 | 7/2014 | Miller et al. |
| 8,845,717 B2 | 9/2014 | Khairkhahan et al. |
| 8,888,843 B2 | 11/2014 | Khairkhahan et al. |
| 8,900,214 B2 | 12/2014 | Nance et al. |
| 8,900,295 B2 | 12/2014 | Migliazza et al. |
| 8,926,696 B2 | 1/2015 | Cabiri et al. |
| 8,932,342 B2 | 1/2015 | McHugo et al. |
| 8,932,348 B2 | 1/2015 | Solem et al. |
| 8,945,208 B2 | 2/2015 | Jimenez et al. |
| 8,956,407 B2 | 2/2015 | Macoviak et al. |
| 8,979,922 B2 | 3/2015 | Thambar et al. |
| 8,986,376 B2 | 3/2015 | Solem |
| 9,011,522 B2 | 4/2015 | Annest et al. |
| 9,023,099 B2 | 5/2015 | Duffy et al. |
| 9,034,032 B2 | 5/2015 | McLean et al. |
| 9,034,033 B2 | 5/2015 | McLean et al. |
| 9,039,757 B2 | 5/2015 | McLean et al. |
| 9,039,759 B2 | 5/2015 | Alkhatib et al. |
| 9,078,645 B2 | 7/2015 | Conklin et al. |
| 9,078,749 B2 | 7/2015 | Lutter et al. |
| 9,084,676 B2 | 7/2015 | Chau et al. |
| 9,095,433 B2 | 8/2015 | Lutter et al. |
| 9,125,742 B2 | 9/2015 | Yoganathan et al. |
| 9,149,357 B2 | 10/2015 | Sequin |
| 9,161,837 B2 | 10/2015 | Kapadia |
| 9,168,137 B2 | 10/2015 | Subramanian et al. |
| 9,232,995 B2 | 1/2016 | Kovalsky et al. |
| 9,232,998 B2 | 1/2016 | Wilson et al. |
| 9,232,999 B2 | 1/2016 | Maurer et al. |
| 9,241,702 B2 | 1/2016 | Maisano et al. |
| 9,254,192 B2 | 2/2016 | Lutter et al. |
| 9,265,608 B2 | 2/2016 | Miller et al. |
| 9,289,295 B2 | 3/2016 | Aklog et al. |
| 9,289,297 B2 | 3/2016 | Wilson et al. |
| 9,345,573 B2 | 5/2016 | Nyuli et al. |
| 9,480,557 B2 | 11/2016 | Pellegrini et al. |
| 9,480,559 B2 | 11/2016 | Vidlund et al. |
| 9,526,611 B2 | 12/2016 | Tegels et al. |
| 9,597,181 B2 | 3/2017 | Christianson et al. |
| 9,610,159 B2 | 4/2017 | Christianson et al. |
| 9,675,454 B2 | 6/2017 | Vidlund et al. |
| 9,730,792 B2 | 8/2017 | Lutter et al. |
| 9,827,092 B2 | 11/2017 | Vidlund et al. |
| 9,833,315 B2 | 12/2017 | Vidlund et al. |
| 9,867,700 B2 | 1/2018 | Bakis et al. |
| 9,895,221 B2 | 2/2018 | Vidlund |
| 9,986,993 B2 | 6/2018 | Vidlund et al. |
| 10,034,749 B2 * | 7/2018 | Spence ................ A61F 2/2409 |
| 2001/0018611 A1 | 8/2001 | Solem et al. |
| 2001/0021872 A1 | 9/2001 | Bailey et al. |
| 2001/0025171 A1 | 9/2001 | Mortier et al. |
| 2002/0010427 A1 | 1/2002 | Scarfone et al. |
| 2002/0116054 A1 | 8/2002 | Lundell et al. |
| 2002/0139056 A1 | 10/2002 | Finnell |
| 2002/0151961 A1 | 10/2002 | Lashinski et al. |
| 2002/0161377 A1 | 10/2002 | Rabkin |
| 2002/0173842 A1 | 11/2002 | Buchanan |
| 2002/0183827 A1 | 12/2002 | Derus et al. |
| 2003/0010509 A1 | 1/2003 | Hoffman |
| 2003/0036698 A1 | 2/2003 | Kohler et al. |
| 2003/0050694 A1 | 3/2003 | Yang et al. |
| 2003/0078652 A1 | 4/2003 | Sutherland |
| 2003/0100939 A1 | 5/2003 | Yodfat et al. |
| 2003/0105519 A1 | 6/2003 | Fasol et al. |
| 2003/0105520 A1 | 6/2003 | Alferness et al. |
| 2003/0120340 A1 | 6/2003 | Liska et al. |
| 2003/0130731 A1 | 7/2003 | Vidlund et al. |
| 2003/0149476 A1 | 8/2003 | Damm et al. |
| 2003/0212454 A1 | 11/2003 | Scott et al. |
| 2004/0039436 A1 | 2/2004 | Spenser et al. |
| 2004/0049266 A1 | 3/2004 | Anduiza et al. |
| 2004/0064014 A1 | 4/2004 | Melvin et al. |
| 2004/0092858 A1 | 5/2004 | Wilson et al. |
| 2004/0093075 A1 | 5/2004 | Kuehne |
| 2004/0097865 A1 | 5/2004 | Anderson et al. |
| 2004/0127983 A1 | 7/2004 | Mortier et al. |
| 2004/0133263 A1 | 7/2004 | Dusbabek et al. |
| 2004/0147958 A1 | 7/2004 | Lam et al. |
| 2004/0152947 A1 | 8/2004 | Schroeder et al. |
| 2004/0162610 A1 | 8/2004 | Liska et al. |
| 2004/0163828 A1 | 8/2004 | Silverstein et al. |
| 2004/0181239 A1 | 9/2004 | Dorn et al. |
| 2004/0186565 A1 | 9/2004 | Schreck |
| 2004/0186566 A1 | 9/2004 | Hindrichs et al. |
| 2004/0260317 A1 | 12/2004 | Bloom et al. |
| 2004/0260389 A1 | 12/2004 | Case et al. |
| 2005/0004652 A1 | 1/2005 | Van der Burg et al. |
| 2005/0004666 A1 | 1/2005 | Alfieri et al. |
| 2005/0075727 A1 | 4/2005 | Wheatley |
| 2005/0080402 A1 | 4/2005 | Santamore et al. |
| 2005/0085900 A1 | 4/2005 | Case et al. |
| 2005/0096498 A1 | 5/2005 | Houser et al. |
| 2005/0107661 A1 | 5/2005 | Lau et al. |
| 2005/0113798 A1 | 5/2005 | Slater et al. |
| 2005/0113810 A1 | 5/2005 | Houser et al. |
| 2005/0113811 A1 | 5/2005 | Houser et al. |
| 2005/0119519 A9 | 6/2005 | Girard et al. |
| 2005/0121206 A1 | 6/2005 | Dolan |
| 2005/0125012 A1 | 6/2005 | Houser et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0137698 A1 | 6/2005 | Salahieh et al. |
| 2005/0148815 A1 | 7/2005 | Mortier et al. |
| 2005/0177180 A1 | 8/2005 | Kaganov et al. |
| 2005/0197695 A1 | 9/2005 | Stacchino et al. |
| 2005/0203614 A1 | 9/2005 | Forster et al. |
| 2005/0203615 A1 | 9/2005 | Forster et al. |

(56) References Cited

U.S. PATENT DOCUMENTS

| | | |
|---|---|---|
| 2005/0203617 A1 | 9/2005 | Forster et al. |
| 2005/0234546 A1 | 10/2005 | Nugent et al. |
| 2005/0240200 A1 | 10/2005 | Bergheim |
| 2005/0251209 A1 | 11/2005 | Saadat et al. |
| 2005/0256567 A1 | 11/2005 | Lim et al. |
| 2005/0283231 A1 | 12/2005 | Haug et al. |
| 2005/0288766 A1 | 12/2005 | Plain et al. |
| 2006/0004442 A1 | 1/2006 | Spenser et al. |
| 2006/0025784 A1 | 2/2006 | Starksen et al. |
| 2006/0025857 A1 | 2/2006 | Bergheim et al. |
| 2006/0030885 A1 | 2/2006 | Hyde |
| 2006/0042803 A1 | 3/2006 | Gallaher |
| 2006/0047338 A1 | 3/2006 | Jenson et al. |
| 2006/0052868 A1 | 3/2006 | Mortier et al. |
| 2006/0058872 A1 | 3/2006 | Salahieh et al. |
| 2006/0094983 A1 | 5/2006 | Burbank et al. |
| 2006/0129025 A1 | 6/2006 | Levine et al. |
| 2006/0142784 A1 | 6/2006 | Kontos |
| 2006/0161040 A1 | 7/2006 | McCarthy et al. |
| 2006/0161249 A1 | 7/2006 | Realyvasquez et al. |
| 2006/0167541 A1 | 7/2006 | Lattouf |
| 2006/0195134 A1 | 8/2006 | Crittenden |
| 2006/0195183 A1 | 8/2006 | Navia et al. |
| 2006/0229708 A1 | 10/2006 | Powell et al. |
| 2006/0229719 A1 | 10/2006 | Marquez et al. |
| 2006/0241745 A1 | 10/2006 | Solem |
| 2006/0247491 A1 | 11/2006 | Vidlund et al. |
| 2006/0252984 A1 | 11/2006 | Rahdert et al. |
| 2006/0259135 A1* | 11/2006 | Navia ................ A61F 2/2409 623/2.11 |
| 2006/0259136 A1 | 11/2006 | Nguyen et al. |
| 2006/0259137 A1 | 11/2006 | Artof et al. |
| 2006/0276874 A1 | 12/2006 | Wilson et al. |
| 2006/0282161 A1 | 12/2006 | Huynh et al. |
| 2006/0287716 A1 | 12/2006 | Banbury et al. |
| 2006/0287717 A1 | 12/2006 | Rowe et al. |
| 2007/0005131 A1 | 1/2007 | Taylor |
| 2007/0005231 A1 | 1/2007 | Seguchi |
| 2007/0010877 A1 | 1/2007 | Salahieh et al. |
| 2007/0016286 A1 | 1/2007 | Herrmann et al. |
| 2007/0016288 A1 | 1/2007 | Gurskis et al. |
| 2007/0027535 A1 | 2/2007 | Purdy et al. |
| 2007/0038291 A1 | 2/2007 | Case et al. |
| 2007/0050020 A1 | 3/2007 | Spence |
| 2007/0061010 A1 | 3/2007 | Hauser et al. |
| 2007/0066863 A1 | 3/2007 | Rafiee et al. |
| 2007/0073387 A1 | 3/2007 | Forster et al. |
| 2007/0078297 A1 | 4/2007 | Rafiee et al. |
| 2007/0083076 A1 | 4/2007 | Lichtenstein |
| 2007/0083259 A1 | 4/2007 | Bloom et al. |
| 2007/0093890 A1 | 4/2007 | Eliasen et al. |
| 2007/0100439 A1 | 5/2007 | Cangialosi et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118210 A1 | 5/2007 | Pinchuk |
| 2007/0118213 A1 | 5/2007 | Loulmet |
| 2007/0142906 A1 | 6/2007 | Figulla et al. |
| 2007/0161846 A1 | 7/2007 | Nikolic et al. |
| 2007/0162048 A1 | 7/2007 | Quinn et al. |
| 2007/0162103 A1 | 7/2007 | Case et al. |
| 2007/0168024 A1 | 7/2007 | Khairkhahan |
| 2007/0185565 A1 | 8/2007 | Schwammenthal et al. |
| 2007/0185571 A1 | 8/2007 | Kapadia et al. |
| 2007/0203575 A1 | 8/2007 | Forster et al. |
| 2007/0213813 A1 | 9/2007 | Von Segesser et al. |
| 2007/0215362 A1 | 9/2007 | Rodgers |
| 2007/0221388 A1 | 9/2007 | Johnson |
| 2007/0233239 A1 | 10/2007 | Navia et al. |
| 2007/0239265 A1 | 10/2007 | Birdsall |
| 2007/0256843 A1 | 11/2007 | Pahila |
| 2007/0265658 A1 | 11/2007 | Nelson et al. |
| 2007/0267202 A1 | 11/2007 | Mariller |
| 2007/0270932 A1 | 11/2007 | Headley et al. |
| 2007/0270943 A1 | 11/2007 | Solem |
| 2007/0293944 A1 | 12/2007 | Spenser et al. |
| 2008/0009940 A1 | 1/2008 | Cribier |
| 2008/0033543 A1 | 2/2008 | Gurskis et al. |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0082163 A1 | 4/2008 | Woo |
| 2008/0082166 A1 | 4/2008 | Styrc et al. |
| 2008/0091264 A1 | 4/2008 | Machold et al. |
| 2008/0114442 A1 | 5/2008 | Mitchell et al. |
| 2008/0125861 A1 | 5/2008 | Webler et al. |
| 2008/0147179 A1 | 6/2008 | Cai et al. |
| 2008/0154355 A1 | 6/2008 | Benichou et al. |
| 2008/0154356 A1 | 6/2008 | Obermiller et al. |
| 2008/0161911 A1 | 7/2008 | Revuelta et al. |
| 2008/0172035 A1 | 7/2008 | Starksen et al. |
| 2008/0177381 A1 | 7/2008 | Navia et al. |
| 2008/0183203 A1 | 7/2008 | Fitzgerald et al. |
| 2008/0183273 A1 | 7/2008 | Mesana et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0243150 A1 | 10/2008 | Starksen et al. |
| 2008/0243245 A1 | 10/2008 | Thambar et al. |
| 2008/0255660 A1 | 10/2008 | Guyenot et al. |
| 2008/0255661 A1 | 10/2008 | Straubinger et al. |
| 2008/0281411 A1 | 11/2008 | Berreklouw |
| 2008/0288060 A1 | 11/2008 | Kaye et al. |
| 2008/0293996 A1 | 11/2008 | Evans et al. |
| 2009/0005863 A1 | 1/2009 | Goetz et al. |
| 2009/0048668 A1 | 2/2009 | Wilson et al. |
| 2009/0054968 A1 | 2/2009 | Bonhoeffer et al. |
| 2009/0054974 A1 | 2/2009 | McGuckin, Jr. et al. |
| 2009/0062908 A1 | 3/2009 | Bonhoeffer et al. |
| 2009/0076598 A1 | 3/2009 | Salahieh et al. |
| 2009/0082619 A1 | 3/2009 | De Marchena |
| 2009/0088836 A1 | 4/2009 | Bishop et al. |
| 2009/0099410 A1 | 4/2009 | De Marchena |
| 2009/0112309 A1 | 4/2009 | Jaramillo |
| 2009/0131849 A1 | 5/2009 | Maurer et al. |
| 2009/0132035 A1 | 5/2009 | Roth et al. |
| 2009/0137861 A1 | 5/2009 | Goldberg et al. |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0177266 A1 | 7/2009 | Powell et al. |
| 2009/0192601 A1 | 7/2009 | Rafiee et al. |
| 2009/0210052 A1 | 8/2009 | Forster et al. |
| 2009/0216322 A1 | 8/2009 | Le et al. |
| 2009/0222076 A1 | 9/2009 | Figulla et al. |
| 2009/0224529 A1 | 9/2009 | Gill |
| 2009/0234318 A1 | 9/2009 | Loulmet et al. |
| 2009/0234435 A1 | 9/2009 | Johnson et al. |
| 2009/0234443 A1 | 9/2009 | Ottma et al. |
| 2009/0240320 A1 | 9/2009 | Tuval et al. |
| 2009/0248149 A1 | 10/2009 | Gabbay |
| 2009/0276040 A1 | 11/2009 | Rowe et al. |
| 2009/0281619 A1 | 11/2009 | Le et al. |
| 2009/0287299 A1 | 11/2009 | Tabor et al. |
| 2009/0292262 A1 | 11/2009 | Adams et al. |
| 2009/0319037 A1 | 12/2009 | Rowe et al. |
| 2009/0326575 A1 | 12/2009 | Galdonik et al. |
| 2010/0016958 A1 | 1/2010 | St. Goar et al. |
| 2010/0021382 A1 | 1/2010 | Dorshow et al. |
| 2010/0023117 A1 | 1/2010 | Yoganathan et al. |
| 2010/0036479 A1 | 2/2010 | Hill et al. |
| 2010/0049313 A1 | 2/2010 | Alon et al. |
| 2010/0082094 A1 | 4/2010 | Quadri et al. |
| 2010/0161041 A1 | 6/2010 | Maisano et al. |
| 2010/0168839 A1 | 7/2010 | Braido et al. |

(56) References Cited

U.S. PATENT DOCUMENTS

| | | |
|---|---|---|
| 2010/0179641 A1 | 7/2010 | Ryan et al. |
| 2010/0185277 A1 | 7/2010 | Braido et al. |
| 2010/0185278 A1 | 7/2010 | Schankereli |
| 2010/0191326 A1 | 7/2010 | Alkhatib |
| 2010/0192402 A1 | 8/2010 | Yamaguchi et al. |
| 2010/0204781 A1 | 8/2010 | Alkhatib |
| 2010/0210899 A1 | 8/2010 | Schankereli |
| 2010/0217382 A1 | 8/2010 | Chau et al. |
| 2010/0249489 A1 | 9/2010 | Jarvik |
| 2010/0249923 A1 | 9/2010 | Alkhatib et al. |
| 2010/0280604 A1 | 11/2010 | Zipory et al. |
| 2010/0286768 A1 | 11/2010 | Alkhatib |
| 2010/0298755 A1 | 11/2010 | McNamara et al. |
| 2010/0298931 A1 | 11/2010 | Quadri et al. |
| 2011/0004296 A1 | 1/2011 | Lutter et al. |
| 2011/0015616 A1 | 1/2011 | Straubinger et al. |
| 2011/0015728 A1 | 1/2011 | Jimenez et al. |
| 2011/0015729 A1 | 1/2011 | Jimenez et al. |
| 2011/0029072 A1 | 2/2011 | Gabbay |
| 2011/0066231 A1 | 3/2011 | Cartledge et al. |
| 2011/0066233 A1 | 3/2011 | Thornton et al. |
| 2011/0112632 A1 | 5/2011 | Chau et al. |
| 2011/0137397 A1 | 6/2011 | Chau et al. |
| 2011/0137408 A1 | 6/2011 | Bergheim |
| 2011/0224655 A1 | 9/2011 | Asirvatham et al. |
| 2011/0224678 A1 | 9/2011 | Gabbay |
| 2011/0224728 A1 | 9/2011 | Martin et al. |
| 2011/0224784 A1 | 9/2011 | Quinn |
| 2011/0245911 A1 | 10/2011 | Quill et al. |
| 2011/0251682 A1 | 10/2011 | Murray, III et al. |
| 2011/0264191 A1 | 10/2011 | Rothstein |
| 2011/0264206 A1 | 10/2011 | Tabor |
| 2011/0288637 A1 | 11/2011 | De Marchena |
| 2011/0319988 A1 | 12/2011 | Schankereli et al. |
| 2011/0319989 A1 | 12/2011 | Lane et al. |
| 2012/0010694 A1 | 1/2012 | Lutter et al. |
| 2012/0016468 A1 | 1/2012 | Robin et al. |
| 2012/0022640 A1 | 1/2012 | Gross et al. |
| 2012/0035703 A1 | 2/2012 | Lutter et al. |
| 2012/0035713 A1 | 2/2012 | Lutter et al. |
| 2012/0035722 A1 | 2/2012 | Tuval |
| 2012/0053686 A1 | 3/2012 | McNamara et al. |
| 2012/0059487 A1 | 3/2012 | Cunanan et al. |
| 2012/0089171 A1 | 4/2012 | Hastings et al. |
| 2012/0101571 A1 | 4/2012 | Thambar et al. |
| 2012/0101572 A1 | 4/2012 | Kovalsky et al. |
| 2012/0116351 A1 | 5/2012 | Chomas et al. |
| 2012/0123529 A1 | 5/2012 | Levi et al. |
| 2012/0165930 A1 | 6/2012 | Gifford et al. |
| 2012/0179244 A1 | 7/2012 | Schankereli et al. |
| 2012/0203336 A1 | 8/2012 | Annest |
| 2012/0215303 A1 | 8/2012 | Quadri et al. |
| 2012/0226348 A1 | 9/2012 | Lane et al. |
| 2012/0283824 A1 | 11/2012 | Lutter et al. |
| 2012/0289945 A1 | 11/2012 | Segermark |
| 2013/0030522 A1 | 1/2013 | Rowe et al. |
| 2013/0053950 A1 | 2/2013 | Rowe et al. |
| 2013/0066341 A1 | 3/2013 | Ketai et al. |
| 2013/0079873 A1 | 3/2013 | Migliazza et al. |
| 2013/0131788 A1 | 5/2013 | Quadri et al. |
| 2013/0172978 A1 | 7/2013 | Vidlund et al. |
| 2013/0184811 A1 | 7/2013 | Rowe et al. |
| 2013/0190860 A1 | 7/2013 | Sundt, III |
| 2013/0190861 A1 | 7/2013 | Chau et al. |
| 2013/0197622 A1 | 8/2013 | Mitra et al. |
| 2013/0226288 A1 | 8/2013 | Goldwasser et al. |
| 2013/0231735 A1 | 9/2013 | Deem et al. |
| 2013/0274874 A1 | 10/2013 | Hammer |
| 2013/0282101 A1 | 10/2013 | Eidenschink et al. |
| 2013/0310928 A1 | 11/2013 | Morriss et al. |
| 2013/0317603 A1 | 11/2013 | McLean et al. |
| 2013/0325041 A1 | 12/2013 | Annest et al. |
| 2013/0325110 A1 | 12/2013 | Khalil et al. |
| 2013/0338752 A1 | 12/2013 | Geusen et al. |
| 2014/0046433 A1 | 2/2014 | Kovalsky |
| 2014/0081323 A1 | 3/2014 | Hawkins |
| 2014/0094918 A1 | 4/2014 | Vishnubholta et al. |
| 2014/0142691 A1 | 5/2014 | Pouletty |
| 2014/0163668 A1 | 6/2014 | Rafiee |
| 2014/0194981 A1 | 7/2014 | Menk et al. |
| 2014/0194983 A1 | 7/2014 | Kovalsky et al. |
| 2014/0214159 A1 | 7/2014 | Vidlund et al. |
| 2014/0222142 A1 | 8/2014 | Kovalsky et al. |
| 2014/0243966 A1 | 8/2014 | Garde et al. |
| 2014/0257475 A1* | 9/2014 | Gross ............... A61F 2/2439 623/2.38 |
| 2014/0277411 A1* | 9/2014 | Bortlein ............. A61F 2/24 623/2.11 |
| 2014/0277419 A1 | 9/2014 | Garde et al. |
| 2014/0296969 A1 | 10/2014 | Tegels et al. |
| 2014/0296970 A1 | 10/2014 | Ekvall et al. |
| 2014/0296971 A1 | 10/2014 | Tegels et al. |
| 2014/0296972 A1 | 10/2014 | Tegels et al. |
| 2014/0296975 A1 | 10/2014 | Tegels et al. |
| 2014/0303718 A1 | 10/2014 | Tegels et al. |
| 2014/0309732 A1 | 10/2014 | Solem |
| 2014/0316516 A1 | 10/2014 | Vidlund et al. |
| 2014/0324160 A1 | 10/2014 | Benichou et al. |
| 2014/0324161 A1 | 10/2014 | Tegels et al. |
| 2014/0324164 A1 | 10/2014 | Gross et al. |
| 2014/0331475 A1 | 11/2014 | Duffy et al. |
| 2014/0358224 A1 | 12/2014 | Tegels et al. |
| 2014/0364942 A1 | 12/2014 | Straubinger et al. |
| 2014/0364944 A1 | 12/2014 | Lutter et al. |
| 2014/0379076 A1 | 12/2014 | Vidlund et al. |
| 2015/0005874 A1 | 1/2015 | Vidlund et al. |
| 2015/0011821 A1 | 1/2015 | Gorman et al. |
| 2015/0025553 A1 | 1/2015 | Del Nido et al. |
| 2015/0057705 A1 | 2/2015 | Vidlund et al. |
| 2015/0073542 A1 | 3/2015 | Heldman |
| 2015/0073545 A1 | 3/2015 | Braido |
| 2015/0094802 A1 | 4/2015 | Buchbinder et al. |
| 2015/0105856 A1 | 4/2015 | Rowe et al. |
| 2015/0119936 A1 | 4/2015 | Gilmore et al. |
| 2015/0119978 A1 | 4/2015 | Tegels et al. |
| 2015/0127093 A1 | 5/2015 | Hosmer et al. |
| 2015/0127096 A1 | 5/2015 | Rowe et al. |
| 2015/0134050 A1 | 5/2015 | Solem et al. |
| 2015/0142100 A1 | 5/2015 | Morriss et al. |
| 2015/0142101 A1 | 5/2015 | Coleman et al. |
| 2015/0142103 A1 | 5/2015 | Vidlund |
| 2015/0142104 A1 | 5/2015 | Braido |
| 2015/0173897 A1 | 6/2015 | Raanani et al. |
| 2015/0196393 A1 | 7/2015 | Vidlund et al. |
| 2015/0196688 A1 | 7/2015 | James et al. |
| 2015/0202044 A1 | 7/2015 | Chau et al. |
| 2015/0216653 A1 | 8/2015 | Freudenthanl |
| 2015/0216660 A1 | 8/2015 | Pintor et al. |
| 2015/0223820 A1 | 8/2015 | Olson et al. |
| 2015/0223934 A1 | 8/2015 | Vidlund et al. |
| 2015/0238312 A1 | 8/2015 | Lashinski |
| 2015/0238729 A1 | 8/2015 | Jenson et al. |
| 2015/0272731 A1 | 10/2015 | Racchini et al. |
| 2015/0305860 A1 | 10/2015 | Wang et al. |
| 2015/0305864 A1 | 10/2015 | Quadri et al. |
| 2015/0305868 A1 | 10/2015 | Lutter et al. |
| 2015/0313620 A1* | 11/2015 | Suri ............... A61B 17/0401 606/205 |
| 2015/0327995 A1 | 11/2015 | Morin et al. |
| 2015/0328001 A1 | 11/2015 | McLean et al. |
| 2015/0335424 A1 | 11/2015 | McLean et al. |
| 2015/0335429 A1 | 11/2015 | Morriss et al. |
| 2015/0342717 A1 | 12/2015 | O'Donnell et al. |
| 2015/0351903 A1 | 12/2015 | Morriss et al. |
| 2015/0351906 A1 | 12/2015 | Hammer et al. |
| 2016/0000562 A1 | 1/2016 | Siegel |
| 2016/0008131 A1* | 1/2016 | Christianson ....... A61F 2/2418 623/2.11 |
| 2016/0067042 A1 | 3/2016 | Murad et al. |
| 2016/0074160 A1 | 3/2016 | Christianson et al. |
| 2016/0106537 A1 | 4/2016 | Christianson et al. |
| 2016/0113764 A1 | 4/2016 | Sheahan et al. |
| 2016/0143736 A1 | 5/2016 | Vidlund et al. |
| 2016/0151155 A1 | 6/2016 | Lutter et al. |

(56) References Cited

U.S. PATENT DOCUMENTS

| | | | |
|---|---|---|---|
| 2016/0206280 A1 | 7/2016 | Vidlund et al. |
| 2016/0242902 A1 | 8/2016 | Morriss et al. |
| 2016/0262879 A1 | 9/2016 | Meiri et al. |
| 2016/0262881 A1 | 9/2016 | Schankereli et al. |
| 2016/0278955 A1 | 9/2016 | Liu et al. |
| 2016/0317290 A1 | 11/2016 | Chau et al. |
| 2016/0324635 A1 | 11/2016 | Vidlund et al. |
| 2016/0331527 A1 | 11/2016 | Vidlund et al. |
| 2016/0346086 A1 | 12/2016 | Solem |
| 2016/0367365 A1 | 12/2016 | Conklin |
| 2016/0367367 A1 | 12/2016 | Maisano et al. |
| 2016/0367368 A1 | 12/2016 | Vidlund et al. |
| 2017/0079790 A1 | 3/2017 | Vidlund et al. |
| 2017/0100248 A1 | 4/2017 | Tegels et al. |
| 2017/0128208 A1 | 5/2017 | Christianson et al. |
| 2017/0181854 A1 | 6/2017 | Christianson et al. |
| 2017/0196688 A1 | 7/2017 | Christianson et al. |
| 2017/0252153 A1 | 9/2017 | Chau et al. |
| 2017/0266001 A1 | 9/2017 | Vidlund et al. |
| 2017/0281343 A1 | 10/2017 | Christianson et al. |
| 2017/0312076 A1 | 11/2017 | Lutter et al. |
| 2017/0312077 A1 | 11/2017 | Vidlund et al. |
| 2018/0028314 A1 | 2/2018 | Ekvall et al. |
| 2018/0078368 A1 | 3/2018 | Vidlund et al. |
| 2018/0078370 A1 | 3/2018 | Kovalsky et al. |
| 2018/0147055 A1 | 5/2018 | Vidlund et al. |

FOREIGN PATENT DOCUMENTS

| | | |
|---|---|---|
| CN | 2902226 | 5/2007 |
| CN | 101146484 | 3/2008 |
| CN | 101180010 | 5/2008 |
| CN | 101984938 | 3/2011 |
| CN | 102869317 | 1/2013 |
| CN | 102869318 | 1/2013 |
| CN | 102869321 | 1/2013 |
| CN | 103220993 | 7/2013 |
| CN | 102639179 B | 10/2014 |
| DE | 2246526 | 3/1973 |
| DE | 19532846 | 3/1997 |
| DE | 19546692 | 6/1997 |
| DE | 19857887 | 7/2000 |
| DE | 19907646 | 8/2000 |
| DE | 10049812 | 4/2002 |
| DE | 10049813 | 4/2002 |
| DE | 10049815 | 4/2002 |
| DE | 102006052564 | 12/2007 |
| DE | 102006052710 | 5/2008 |
| DE | 102007043830 A1 | 4/2009 |
| DE | 102007043831 | 4/2009 |
| EP | 0103546 | 5/1988 |
| EP | 1057460 | 12/2000 |
| EP | 1088529 | 4/2001 |
| EP | 1469797 | 11/2005 |
| EP | 2111800 | 10/2009 |
| EP | 2193762 | 6/2010 |
| EP | 2747707 | 4/2015 |
| EP | 2918248 | 9/2015 |
| EP | 2278944 | 3/2016 |
| FR | 2788217 | 7/2000 |
| FR | 2815844 | 5/2002 |
| JP | 2003-505146 | 2/2003 |
| JP | 2005-515836 | 6/2005 |
| JP | 2009-514628 | 4/2009 |
| JP | 2009-519783 | 5/2009 |
| JP | 2013-512765 | 4/2013 |
| NL | 1017275 | 8/2002 |
| SU | 1271508 | 11/1986 |
| WO | WO 92/17118 | 10/1992 |
| WO | WO 93/01768 | 2/1993 |
| WO | WO 98/29057 | 7/1998 |
| WO | WO 99/40964 | 8/1999 |
| WO | WO 99/47075 | 9/1999 |
| WO | WO 2000/018333 | 4/2000 |
| WO | WO 2000/030550 | 6/2000 |
| WO | WO 2000/041652 | 7/2000 |
| WO | WO 2000/047139 | 8/2000 |
| WO | WO 2001/035878 | 5/2001 |
| WO | WO 2001/049213 | 7/2001 |
| WO | WO 2001/054624 | 8/2001 |
| WO | WO 2001/054625 | 8/2001 |
| WO | WO 2001/056512 | 8/2001 |
| WO | WO 2001/061289 | 8/2001 |
| WO | WO 2001/076510 | 10/2001 |
| WO | WO 2001/082840 | 11/2001 |
| WO | WO 2002/004757 | 1/2002 |
| WO | WO 2002/022054 | 3/2002 |
| WO | WO 2002/028321 | 4/2002 |
| WO | WO 2002/036048 | 5/2002 |
| WO | WO 2002/041789 | 5/2002 |
| WO | WO 2002/043620 | 6/2002 |
| WO | WO 2002/049540 | 6/2002 |
| WO | WO 2002/076348 | 10/2002 |
| WO | WO 2003/003943 | 1/2003 |
| WO | WO 2003/030776 | 4/2003 |
| WO | WO 2003/047468 | 6/2003 |
| WO | WO 2003/049619 | 6/2003 |
| WO | WO 2004/019825 | 3/2004 |
| WO | WO 2005/102181 | 11/2005 |
| WO | WO 2006/014233 | 2/2006 |
| WO | WO 2006/034008 | 3/2006 |
| WO | WO 2006/064490 | 6/2006 |
| WO | WO 2006/070372 | 7/2006 |
| WO | WO 2006/105009 | 10/2006 |
| WO | WO 2006/113906 | 10/2006 |
| WO | WO 2006/127756 | 11/2006 |
| WO | WO 2007/081412 | 7/2007 |
| WO | WO 2007/100408 | 9/2007 |
| WO | WO 2008/005405 | 1/2008 |
| WO | WO 2008/035337 | 3/2008 |
| WO | WO 2008/091515 | 7/2008 |
| WO | WO 2008/125906 | 10/2008 |
| WO | WO 2008/147964 | 12/2008 |
| WO | WO 2009/024859 | 2/2009 |
| WO | WO 2009/026563 | 2/2009 |
| WO | WO 2009/045338 | 4/2009 |
| WO | WO 2009/132187 | 10/2009 |
| WO | WO 2010/090878 | 8/2010 |
| WO | WO 2010/098857 | 9/2010 |
| WO | WO 2010/121076 | 10/2010 |
| WO | WO 2011/017440 | 2/2011 |
| WO | WO 2011/022658 | 2/2011 |
| WO | WO 2011/069048 | 6/2011 |
| WO | WO 2011/072084 | 6/2011 |
| WO | WO 2011/106735 | 9/2011 |
| WO | WO 2011/109813 | 9/2011 |
| WO | WO 2011/159342 | 12/2011 |
| WO | WO 2011/163275 | 12/2011 |
| WO | WO 2012/027487 | 3/2012 |
| WO | WO 2012/036742 | 3/2012 |
| WO | WO 2012/095116 | 7/2012 |
| WO | WO 2012/177942 | 12/2012 |
| WO | WO 2013/045262 | 4/2013 |
| WO | WO 2013/059747 | 4/2013 |
| WO | WO 2013/096411 | 6/2013 |
| WO | WO 2013/175468 | 11/2013 |
| WO | WO 2014/121280 | 8/2014 |
| WO | WO 2014/144937 | 9/2014 |
| WO | WO 2014/162306 | 10/2014 |
| WO | WO 2014/189974 | 11/2014 |
| WO | WO 2015/051430 | 4/2015 |
| WO | WO 2015/058039 | 4/2015 |
| WO | WO 2015/063580 | 5/2015 |
| WO | WO 2015/065646 | 5/2015 |
| WO | WO 2015/120122 | 8/2015 |
| WO | WO 2015/138306 | 9/2015 |
| WO | WO 2015/173609 | 11/2015 |
| WO | WO 2016/112085 | 7/2016 |
| WO | WO 2016/126942 | 8/2016 |
| WO | WO 2016/168609 | 10/2016 |
| WO | WO 2016/196933 | 12/2016 |
| WO | WO 2017/096157 | 6/2017 |
| WO | WO 2017/132008 | 8/2017 |

(56) References Cited

FOREIGN PATENT DOCUMENTS

| WO | WO 2017/218375 | 12/2017 |
|---|---|---|
| WO | WO 2018/005779 | 1/2018 |
| WO | WO 2018/013515 | 1/2018 |

OTHER PUBLICATIONS

Al Zaibag, M. et al., "Percutaneous Balloon Valvotomy in Tricuspid Stenosis," British Heart Journal, Jan. 1987, 57(1):51-53.

Al-Khaja, N. et al., "Eleven Years' Experience with Carpentier-Edwards Biological Valves in Relation to Survival and Complications," European Journal of Cardiothoracic Surgery, Jun. 30, 1989, 3:305-311.

Almagor, Y. et al., "Balloon Expandable Stent Implantation in Stenotic Right Heart Valved Conduits," Journal of the American College of Cardiology, Nov. 1, 1990, 16(6):1310-1314.

Andersen, H. R. et al., "Transluminal implantation of artificial heart valves. Description of a new expandable aortic valve and initial results with implantation by catheter technique in closed chest pigs," European Heart Journal, 1992, 13(5):704-708.

Andersen, H. R., "History of Percutaneous Aortic Valve Prosthesis," Herz, Aug. 2009, 34(5):343-346.

Andersen, H. R., "Transluminal catheter implanted prosthetic heart valves," International Journal of Angiology, 1998, 7(2):102-106.

Ashton, R. C., Jr. et al., "Development of an Intraluminal Device for the Treatment of Aortic Regurgitation: Prototype and in Vitro Testing System," Journal of Thoracic and Cardiovascular Surgery, 1996, 112:979-983.

Benchimol, A. et al., "Simultaneous Left Ventricular Echocardiography and Aortic Blood Velocity During Rapid Right Ventricular Pacing in Man," The American Journal of the Medical Sciences, Jan.-Feb. 1977, 273(1):55-62.

Bernacca, G. M. et al., "Polyurethane heart valves: Fatigue failure, calcification, and polyurethane structure," Journal of Biomedical Materials Research, Mar. 5, 1997, 34(3):371-379.

Boudjemline, Y. et al., "Steps Toward the Percutaneous Replacement of Atrioventricular Valves: An Experimental Study," Journal of the American College of Cardiology, Jul. 2005, 46(2):360-365.

Buckberg, G. et al., "Restoring Papillary Muscle Dimensions During Restoration in Dilated Hearts," Interactive CardioVascular and Thoracic Surgery, 2005, 4:475-477.

Chamberlain, G., "Ceramics Replace Body Parts," Design News, Jun. 9, 1997, Issue 11, vol. 52, 5 pages.

Choo, S. J. et al., "Aortic Root Geometry: Pattern of Differences Between Leaflets and Sinuses of Valsava," The Journal of Heart Valve Disease, Jul. 1999, 8:407-415.

Declaration of Malcolm J. R. Dalrymple-Hay, Nov. 9, 2012, pp. 1-11; with Curriculum Vitae, Oct. 4, 2012.

Dotter, C. T. et al., "Transluminal Treatment of Arteriosclerotic Obstruction. Description of a New Technic and a Preliminary Report of its Application," Circulation, Nov. 1964, 30:654-670.

Drawbaugh, K., "Feature—Heart Surgeons Explore Minimally Invasive Methods," Reuters Limited, Jul. 16, 1996, 3 pages.

Gray, H., The Aorta, Anatomy of the Human Body, 1918, Retrieved from the Internet <http://www.bartleby.com/107/142.html> , Oct. 12, 2012, 5 pages.

Gray, H., The Heart, Anatomy of the Human Body, 1918, Retrieved from the Internet <http://education.yahoo.com/reference/gray/subjects/subject/138> , Oct. 8, 2012, 9 pages.

Greenhalgh, E. S., "Design and characterization of a biomimetic prosthetic aortic heart valve," 1994, ProQuest Dissertations and Theses, Department of Fiber and Polymer Science, North Carolina State University at Raleigh, 159 pages.

Inoue, K. et al., "Clinical Application of Transvenous Mitral Commissurotomy by a New Balloon Catheter," The Journal of Thoracic and Cardiovascular Surgery, 1984, 87:394-402.

Jin, X. Y. et al., "Aortic Root Geometry and Stentless Porcine Valve Competence," Seminars in Thoracic and Cardiovascular Surgery, Oct. 1999, 11(4):145-150.

Knudsen, L. L. et al., "Catheter-implanted prosthetic heart valves. Transluminal catheter implantation of a new expandable artificial heart valve in the descending thoracic aorta in isolated vessels and closed chest pigs," The International Journal of Artificial Organs, 1993, 16(5):253-262.

Kolata, G., "Device That Opens Clogged Arteries Gets a Failing Grade in a New Study," New York Times [online], <http://www.nytimes.com/1991/01/03/health/device-that-opens-clogged-arteries-gets-a-faili . . . ,>, published Jan. 3, 1991, retrieved from the Internet on Feb. 5, 2016, 3 pages.

Lawrence, D. D., "Percutaneous Endovascular Graft: Experimental Evaluation," Radiology, 1987, 163:357-360.

Lozonschi, L., et al. "Transapical mitral valved stent implantation: A survival series in swine," The Journal of Thoracic and Cardiovascular Surgery, 140(2):422-426 (Aug. 2010) published online Mar. 12, 2010, 1 page.

Lutter, G. et al., "Mitral Valved Stent Implantation," European Journal of Cardio-Thoracic Surgery, 2010, 38:350-355, 2 pages.

Ma, L. et al., "Double-crowned valved stents for off-pump mitral valve replacement," European Journal of Cardio-Thoracic Surgery, Aug. 2005, 28(2):194-198.

Moazami, N. et al., "Transluminal aortic valve placement: A feasibility study with a newly designed collapsible aortic valve," ASAIO Journal, Sep./ Oct. 1996, 42(5):M381-M385.

Orton, C., "Mitralseal: Hybrid Transcatheter Mitral Valve Replacement," Retrieved from the Internet: <http:/www.acvs.org/symposium/proceedings2011/data/papers/102.pdf>, pp. 311-312.

Pavcnik, D. et al. "Development and Initial Experimental Evaluation of a Prosthetic Aortic Valve for Transcatheter Placement," Radiology, 1992; 183:151-154.

Porstmann, W. et al., "Der Verschluß des Ductus Arteriosus Persistens ohne Thorakotomie," Thoraxchirurgie Vaskuläre Chirurgie, Band 15, Heft 2, Stuttgart, Apr. 1967, pp. 199-203.

Rashkind, W. J., "Creation of an Atrial Septal Defect Without Thoracotomy," The Journal of the American Medical Association, Jun. 13, 1966, 196(11):173-174.

Rashkind, W. J., "Historical Aspects of Interventional Cardiology: Past, Present, Future," Texas Heart Institute Journal, Dec. 1986, 13(4):363-367.

Reul, H. et al., "The Geometry of the Aortic Root in Health, at Valve Disease and After Valve Replacement," J. Biomechanics, 1990, 23(2):181-191.

Rosch, J. et al., "The Birth, Early Years and Future of Interventional Radiology," J Vasc Interv Radiol., Jul. 2003, 4:841-853.

Ross, D. N., "Aortic Valve Surgery," Guy's Hospital, London, 1968, pp. 192-197.

Rousseau, E. P. M. et al., "A mechanical analysis of the closed Hancock heart valve prosthesis," Journal of Biomechanics, 1988, 21(7):545-562.

Sabbah, A. N. et al., "Mechanical Factors in the Degeneration of Porcine Bioprosthetic Valves: An Overview," Dec. 1989, Journal of Cardiac Surgery, 4(4):302-309.

Selby, J. B., "Experience with New Retrieval Forceps for Foreign Body Removal in the Vascular, Urinary, and Biliary Systems," Radiology, 1990, 176:535-538.

Serruys, P. W. et al., "Stenting of Coronary Arteries. Are we the Sorcerer's Apprentice?," European Heart Journal , Sep. 1989, 10(9):774-782.

"Shape Memory Alloys," Retrieved from the Internet: <http://webdocs.cs.ualberta.ca/~database/MEMS/sma.html>, Feb. 5, 2016, 3 pages.

Sigwart, U., "An Overview of Intravascular Stents: Old and New," Chapter 48, Interventional Cardiology, 2nd Edition, W.B. Saunders Company, Philadelphia, PA, © 1994, 1990, pp. 803-815.

Tofeig, M. et al., "Transcatheter Closure of a Mid-Muscular Ventricular Septal Defect with an Amplatzer VSD Occluder Device," Heart, 1999, 81:438-440.

Uchida, B. T. et al., "Modifications of Gianturco Expandable Wire Stents," Am. J. Roentgenol., May 1988, 150(5):1185-1187.

Watt, A. H. et al., "Intravenous Adenosine in the Treatment of the Supraventricular Tachycardia; a Dose-Ranging Study and Interaction with Dipyridamole," British Journal of Clinical Pharmacology, 1986, 21:227-230.

(56) References Cited

OTHER PUBLICATIONS

Webb, J. G. et al., "Percutaneous Aortic Valve Implantation Retrograde from the Femoral Artery," Circulation, 2006, 113:842-850.
Wheatley, D. J., "Valve Prostheses," Rob & Smith's Operative Surgery, Fourth Edition, 1986, pp. 415-424, Butterworths.
Yoganathan, A. P. et al., "The Current Status of Prosthetic Heart Valves," In Polymetric Materials and Artificial Organs, American Chemical Society, 1984, pp. 111-150.

\* cited by examiner

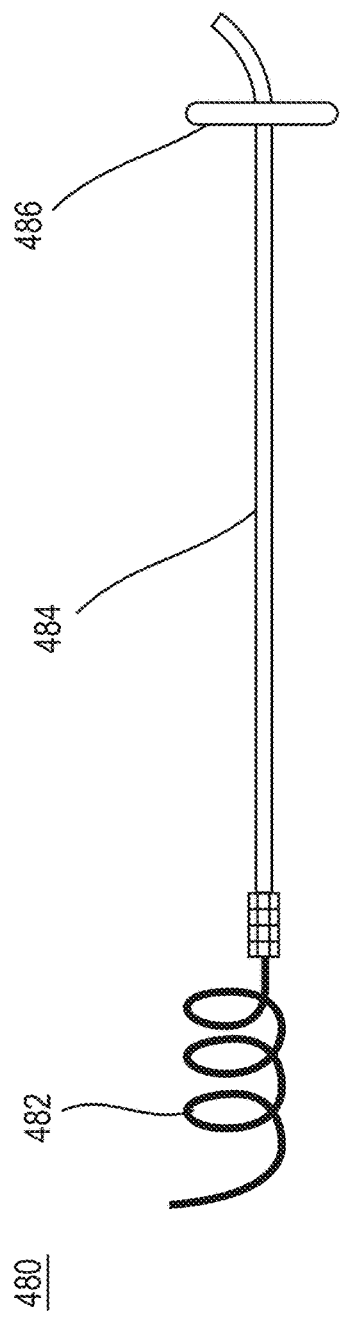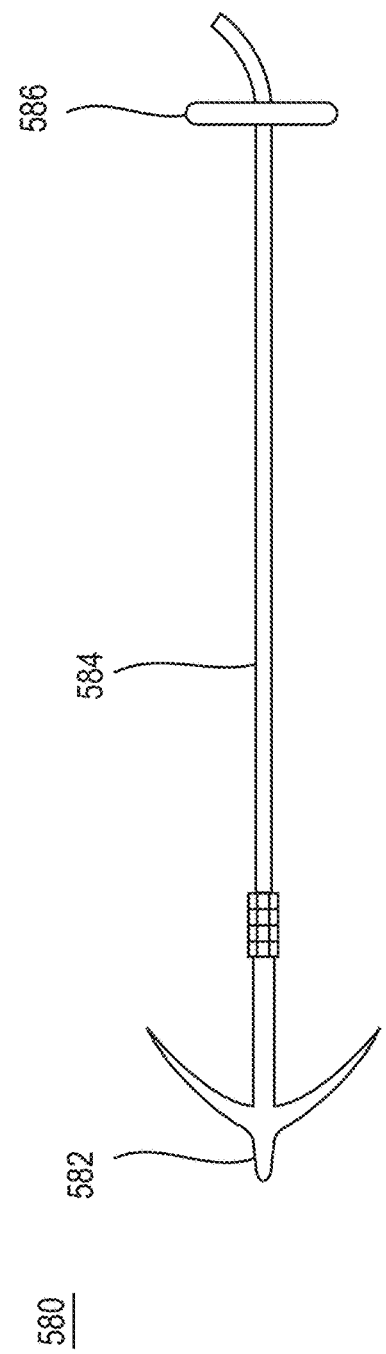

APPARATUS AND METHODS FOR ANTERIOR VALVE LEAFLET MANAGEMENT

CROSS-REFERENCE TO RELATED APPLICATIONS

This application claims priority to and the benefit of U.S. Provisional Application No. 62/331,235, filed May 3, 2016, entitled "Apparatus and Methods for Anterior Valve Leaflet Management," the disclosure of which is incorporated herein by reference in its entirety.

BACKGROUND

Embodiments described herein relate generally to prosthetic heart valves, and devices and methods for management of native mitral valve leaflets. More particularly, embodiments described herein relate to devices, systems and methods for the management of native mitral valve leaflets of patients having an implanted prosthetic heart valve.

The human heart is responsible for pumping blood around the human body. The human heart is separated into four distinct chambers, and is commonly referenced in terms of the right or left side of the heart. The right side of the heart, including the right atrium and the right ventricle, is responsible for receiving de-oxygenated blood from the body, and then pumping the de-oxygenated blood to the lungs in order to oxygenate the blood. The left side of the heart, including the left atrium and left ventricle, is responsible for receiving oxygenated blood from the lungs, and then pumping the oxygenated blood to various parts of the body. The movement of blood within the chambers of the heart is controlled by four valves: aortic, mitral, pulmonic and tricuspid. These valves open and close constantly, and as such, can be subject to wear and tear and other challenges that affect their performance (e.g., mitral valve regurgitation, prolapse, and/or stenosis), and consequently, the entire circulatory system.

Some known devices for repairing the performance of the heart, such as, for example, the performance of a mitral valve of the heart, can include a prosthetic heart valve. The prosthetic heart valve can be implanted and secured to a native annulus of the heart. Mitral valve implantation, however, can be associated with displacement of the native mitral valve apparatus. In such cases, native leaflets of the heart valve can become disposed between the prosthetic heart valve and the myocardium of the heart. Further, when the native valve leaflets are disposed in such a manner, the native valve leaflets can, for example, interfere with blood flow into and out of the left ventricle of the heart (e.g., interfere with left ventricular outflow tract (LVOT), and/or reduce effective orifice area (EOA) through the prosthetic heart valve). Native valve leaflet interference with the LVOT is often referred to as systolic anterior motion (SAM). In some cases, SAM can occur when the native valve leaflets become at least partially disposed in the flow path defined through the LVOT. The occurrence of SAM is often characterized by an undesirable flow gradient within the LVOT, and often requires one or more additional procedures to remove the prosthetic mitral valve or correct or recover the LVOT, or in some cases requires additional medication. In addition, over time, the native valve leaflets can stiffen (e.g., change modulus) due to calcification or the like, resulting in undesirable turbulence, eddies, and/or otherwise undesirable flow profiles within the heart. Even more, such degradation and/or stiffening of the native valve leaflets can, in some cases, cause degradation of the prosthetic heart valve leaflets.

Thus, a need exists for devices and methods for managing a native valve leaflet(s) (e.g., native anterior mitral valve leaflet) of a heart valve when a prosthetic heart valve is disposed and operating therein, to reduce or otherwise limit SAM and other undesirable flow gradients within the heart.

Further, patient screening prior to prosthetic mitral valve implantation can help predict potential risk of SAM. Such screening often prevents patients with considerable risk of SAM, who otherwise would benefit from mitral valve replacement, from undergoing mitral valve replacement with a prosthetic mitral valve apparatus. Thus, a need exists for devices and methods for safely and effectively delivering and deploying a prosthetic heart valve within a heart of a patient who has a considerable risk of SAM.

SUMMARY

Apparatus, systems and methods for managing a native heart valve apparatus, and particularly a native anterior leaflet of a native heart valve, when a prosthetic heart valve is delivered to, or disposed in, a native annulus of the heart are described herein. In some embodiments, a method for managing a native heart valve apparatus includes delivering to a native valve annulus (e.g., a native mitral valve annulus) of a heart a prosthetic heart valve having a body expandable from a collapsed, delivery configuration to an expanded, deployed configuration. The method can further include, after the delivering, causing the prosthetic heart valve to move from the delivery configuration to the deployed configuration. With the prosthetic heart valve in its deployed configuration, an anchor can be delivered and secured to at least one of a fibrous trigone of the heart or an anterior native leaflet of the native valve. With the prosthetic heart valve disposed in the native valve annulus and in its deployed configuration, an anchoring tether can extending from the anchor can be secured to a wall of the heart to urge the anterior native leaflet towards the body of the prosthetic heart valve.

BRIEF DESCRIPTION OF THE FIGURES

FIG. 15A is a side view of a tether-anchor apparatus having a coil anchor, according to an embodiment.

FIG. 15B is a side view of a tether-anchor apparatus having a barb anchor, according to an embodiment.

DETAILED DESCRIPTION

Apparatus, systems and methods are described herein for limiting or preventing LVOT obstruction and SAM in conjunction with an implanted prosthetic valve (e.g., prosthetic mitral valve). In some embodiments, a tether anchor as described herein can be used to manipulate a native anterior valve leaflet away from the LVOT of a heart. In some embodiments, the tether anchor can be manipulated to modify or reshape the geometry of a native mitral valve apparatus. In some embodiments, a tether as described herein can be used to plicate a native anterior leaflet.

In some embodiments, a native leaflet cutter as described herein can be used to grasp and/or resect a native leaflet, thereby limiting LVOT obstruction by the leaflet.

In some embodiments, a native leaflet manipulation system as described herein can be used to capture and immmobilize a native anterior leaflet away from the LVOT. The native leaflet manipulation system may include leaflet clips attached to or integrally formed with a prosthetic mitral valve, and can be manipulated by an operator to capture and restrain the native leaflet.

In some embodiments, tissue ablation as described herein can be used to prevent LVOT obstruction by a native anterior leaflet. An ablation catheter, as described herein with respect to some embodiments, can be used to attach a native valve leaflet to a portion of a prosthetic heart valve.

In some embodiments, a stent as described herein can be delivered and deployed in conjunction with a prosthetic heart valve. The stent, for example, can promote a passageway within the LVOT for blood flow, and can bias the native leaflet away from the passageway and against the prosthetic heart valve.

Figure 1:
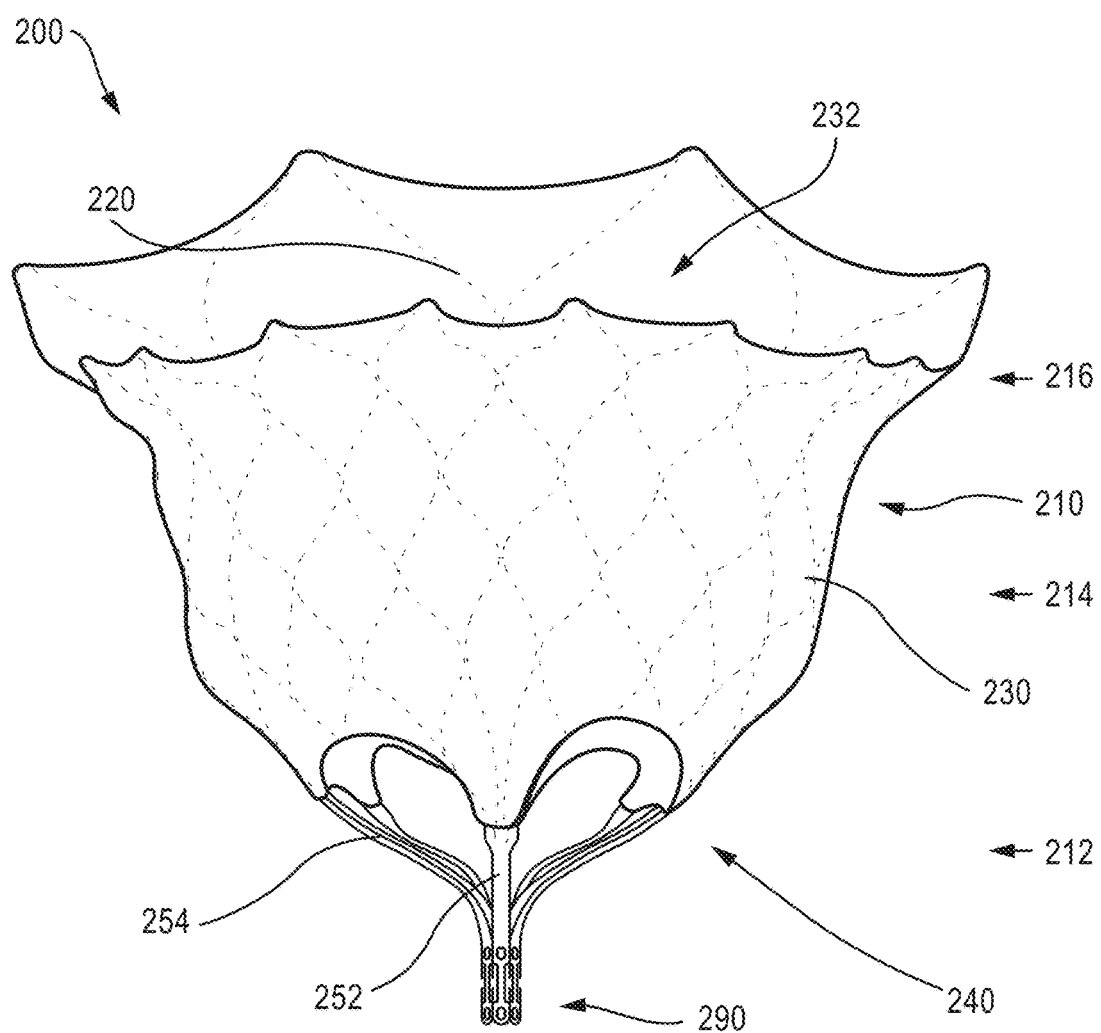
FIGS. 1-3 are front, bottom, and top views of a prosthetic heart valve according to an embodiment.
Figure 2:
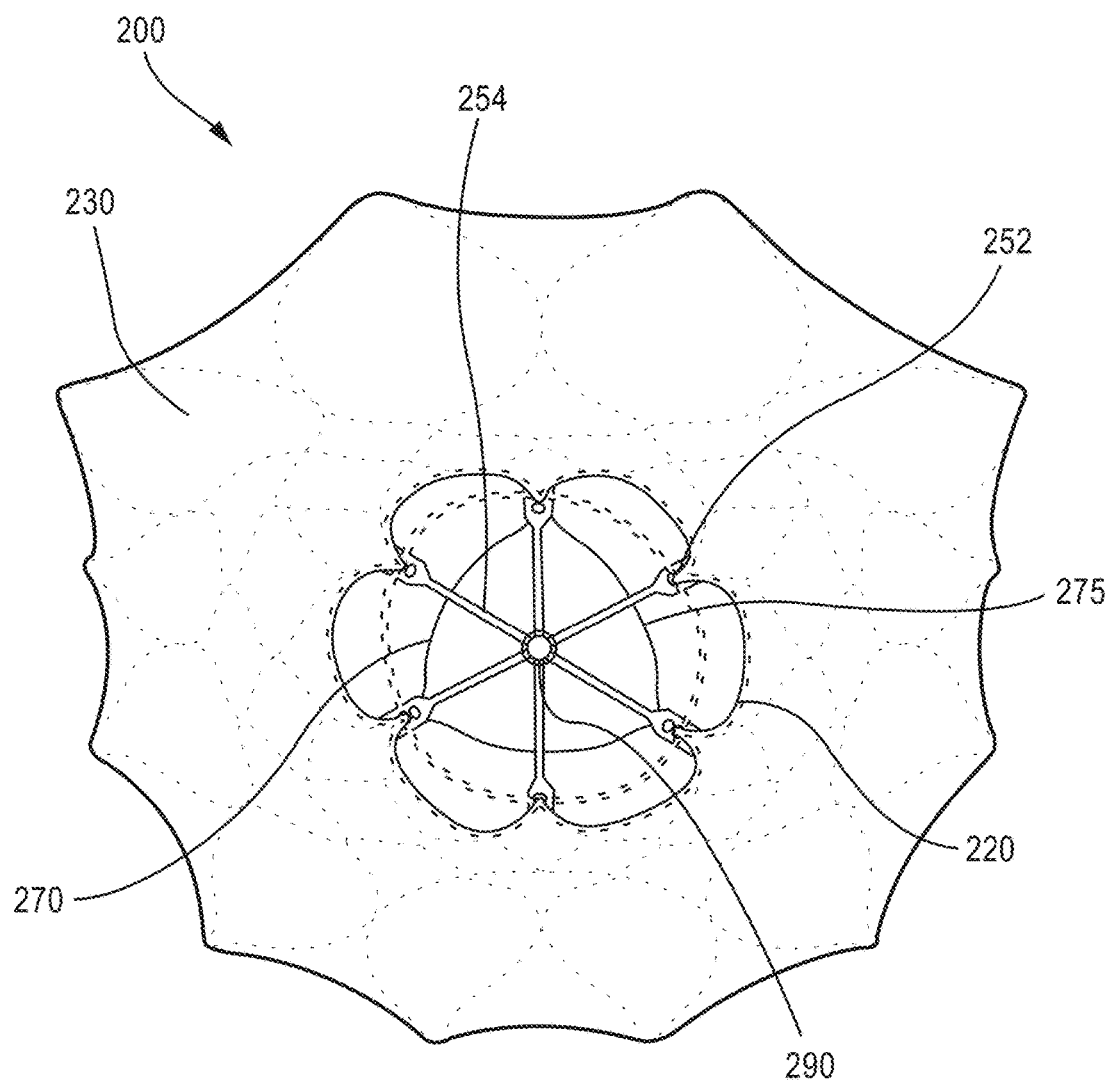
Figure 3:
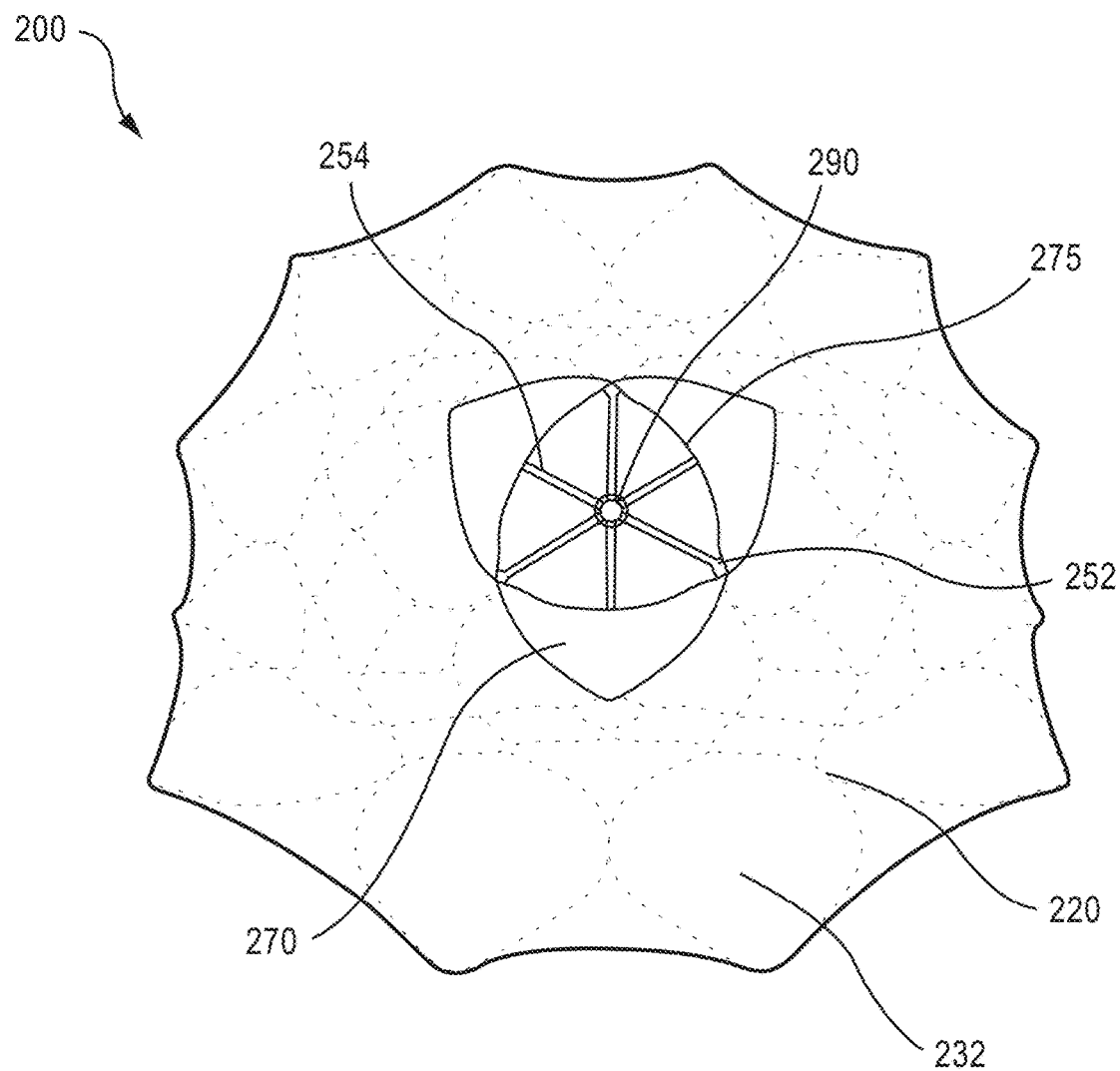

FIGS. 1-12 illustrate an embodiment of a prosthetic heart valve that can be delivered and deployed within a left atrium of a heart using a variety of different delivery approaches including, for example, a transfemoral delivery approach or a transatrial delivery approach. FIGS. 1-3 are front, bottom, and top views, respectively, of a prosthetic heart valve 200 according to an embodiment. Prosthetic heart valve 200 (also referred to herein as "valve" or "prosthetic valve") is designed to replace a damaged or diseased native heart valve such as a mitral valve. Valve 200 includes an outer frame assembly 210 and an inner valve assembly 240 coupled to the outer frame assembly 240.

As shown, outer frame assembly 210 includes an outer frame 220, covered on all or a portion of its outer face with an outer covering 230, and covered on all or a portion of its inner face by an inner covering 232. Outer frame 220 can provide several functions for prosthetic heart valve 200, including serving as the primary structure, as an anchoring mechanism and/or an attachment point for a separate anchoring mechanism to anchor the valve to the native heart valve apparatus, a support to carry inner valve assembly 240, and/or a seal to inhibit paravalvular leakage between prosthetic heart valve 200 and the native heart valve apparatus.

Outer frame 220 has a biased expanded configuration and can be manipulated and/or deformed (e.g., compressed and/or constrained) and, when released, return to its original unconstrained shape. To achieve this, outer frame 220 can be formed of materials, such as metals or plastics, that have shape memory properties. With regards to metals, Nitinol® has been found to be especially useful since it can be processed to be austenitic, martensitic or super elastic. Other shape memory alloys, such as Cu—Zn—Al—Ni alloys, and Cu—Al—Ni alloys, may also be used.

As best shown in FIG. 1, outer frame assembly 210 has an upper end (e.g., at the atrium portion 216), a lower end (e.g., at the ventricle portion 212), and a medial portion (e.g., at the annulus portion 214) therebetween. The upper end or atrium portion 216 (also referred to as "outer free end portion") defines an open end portion of the outer frame assembly 210. The medial or annulus portion 214 of the outer frame assembly 210 has a perimeter that is configured (e.g., sized, shaped) to fit into an annulus of a native atrioventricular valve. The upper end of the outer frame assembly 210 has a perimeter that is larger than the perimeter of the medial portion. In some embodiments, the perimeter of the upper end of the outer frame assembly 210 has a perimeter that is substantially larger than the perimeter of the medial portion. As shown best in FIG. 3, the upper end and the medial portion of the outer frame assembly 210 has a D-shaped cross-section. In this manner, the outer frame assembly 210 promotes a suitable fit into the annulus of the native atrioventricular valve.

Inner valve assembly 240 includes an inner frame 250, an outer covering 260, and leaflets 270. As shown, the inner valve assembly 240 includes an upper portion having a periphery formed with multiple arches. The inner frame 250 includes six axial posts or frame members that support outer covering 260 and leaflets 270. Leaflets 270 are attached along three of the posts, shown as commissure posts 252 (best illustrated in FIG. 2), and outer covering 260 is attached to the other three posts, 254 (best illustrated in FIG. 2), and optionally to commissure posts 252. Each of outer covering 260 and leaflets 270 are formed of approximately rectangular sheets of material, which are joined together at their upper, or atrium end. The lower, ventricle end of outer covering 260 may be joined to inner covering 232 of outer frame assembly 210, and the lower, ventricle end of leaflets 270 may form free edges 275, though coupled to the lower ends of commissure posts 252.

Although inner valve assembly 240 is shown as having three leaflets, in other embodiments, an inner valve assembly can include any suitable number of leaflets. The leaflets 270 are movable between an open configuration and a closed configuration in which the leaflets 270 coapt, or meet in a sealing abutment.

Outer covering 230 of the outer frame assembly 210 and inner covering 232 of outer frame assembly 210, outer covering 260 of the inner valve assembly 240 and leaflets 270 of the inner valve assembly 240 may be formed of any suitable material, or combination of materials, such as those discussed above. In this embodiment, the inner covering 232 of the outer frame assembly 210, the outer covering 260 of the inner valve assembly 240, and the leaflets 270 of the inner valve assembly 240 are formed, at least in part, of porcine pericardium. Moreover, in this embodiment, the outer covering 230 of the outer frame assembly 210 is formed, at least in part, of polyester.

Figure 4:
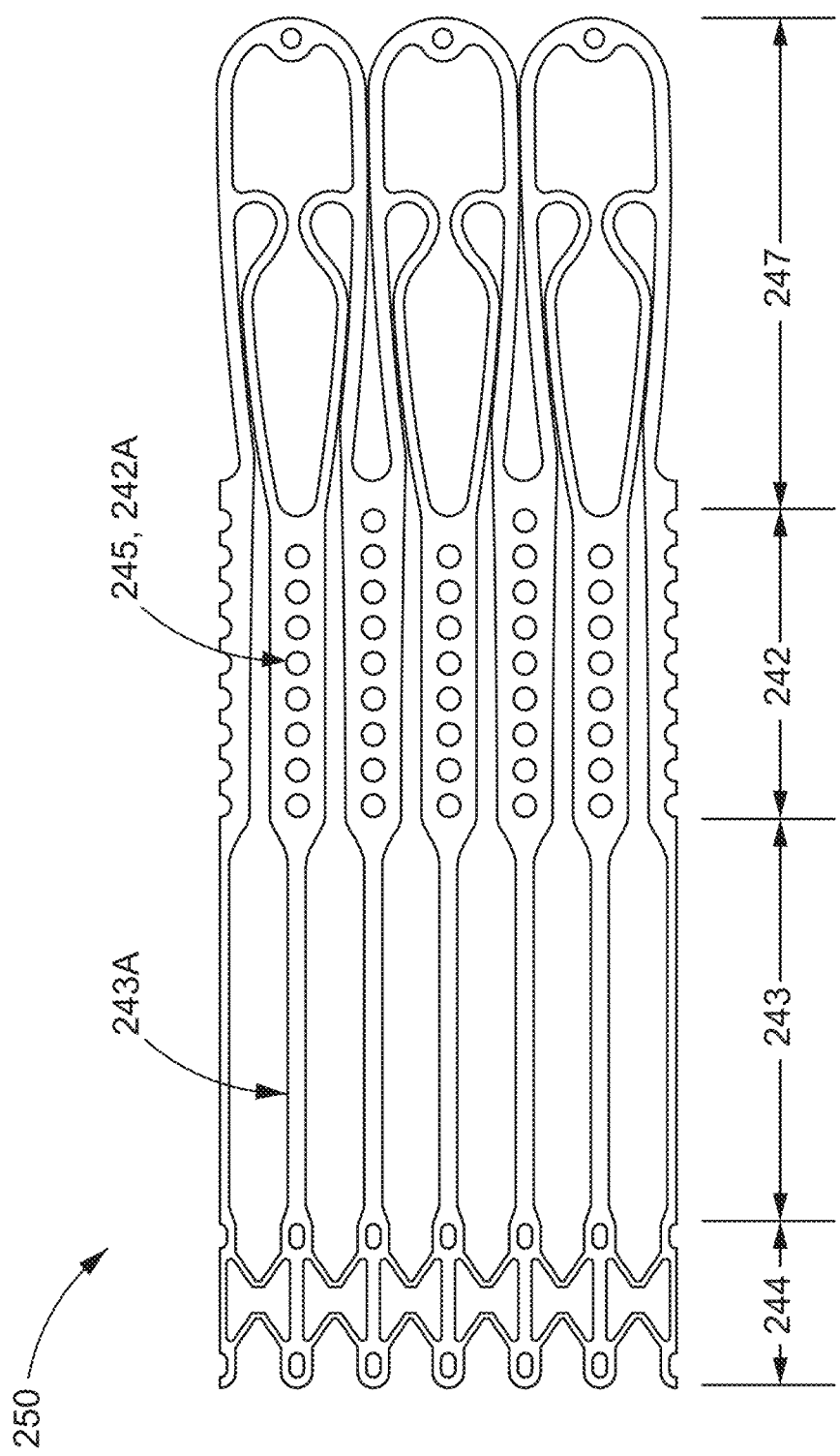
FIG. 4 is an opened and flattened view of the inner frame of the prosthetic heart valve of FIGS. 1-3, in an unexpanded configuration.
Figure 5:
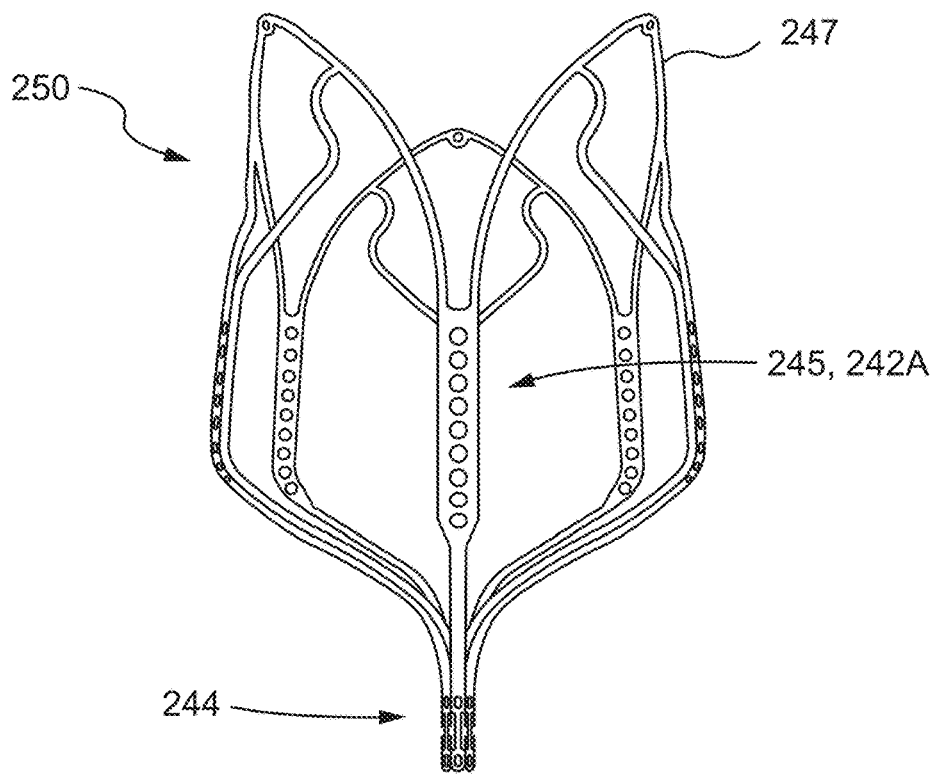
FIGS. 5 and 6 are side and bottom views, respectively, of the inner frame of FIG. 4 in an expanded configuration.
Figure 6:
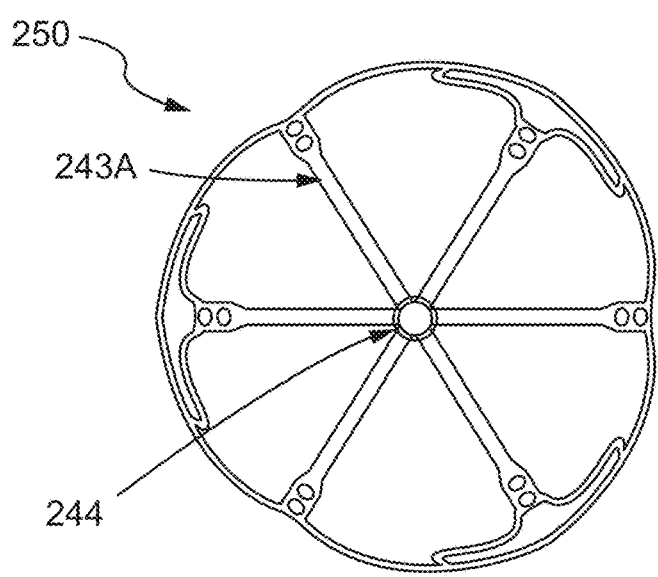

Inner frame 250 is shown in more detail in FIGS. 4-6. Specifically, FIGS. 4-6 show inner frame 250 in an undeformed, initial state (FIG. 4), a side view of the inner frame 250 in an expanded configuration (FIG. 5), and a bottom view of the inner frame 250 in the expanded configuration (FIG. 6), respectively, according to an embodiment.

In this embodiment, inner frame 250 is formed from a laser-cut tube of Nitinol®. Inner frame 250 is illustrated in FIG. 4 in an undeformed, initial state, i.e. as laser-cut, but cut and unrolled into a flat sheet for ease of illustration. Inner frame 250 can be divided into four portions, corresponding to functionally different portions of the inner frame 250 in final form: atrial portion 247, body portion 242, strut portion 243, and tether clamp or connecting portion 244. Strut portion 243 includes six struts, such as strut 243A, which connect body portion 242 to tether connecting portion 244.

Tether connecting portion 244 (also referred to as first end portion of inner frame) includes longitudinal extensions of the struts, connected circumferentially by pairs of opposed, slightly V-shaped connecting members (or "micro-Vs"). Tether connecting portion 244 is configured to be radially collapsed by application of a compressive force, which causes the micro-Vs to become more deeply V-shaped, with the vertices moving closer together longitudinally and the open ends of the V shapes moving closer together circumferentially. Thus, tether connecting portion 244 can be configured to compressively clamp or grip one end of a tether, either connecting directly onto a tether line (e.g. braided filament line) or onto an intermediate structure, such as a polymer or metal piece that is in turn firmly fixed to the tether line.

In contrast to tether connecting portion 244, atrial portion 247 (also referred to as "inner frame free end portion") and body portion 242 are configured to be expanded radially. Strut portion 243 forms a longitudinal connection and radial transition between the expanded body portion and the compressed tether connecting portion 244. Body portion 242 provides an inner frame coupling portion 245 that includes six longitudinal posts, such as post 242A. The inner frame coupling portion 245 can be used to attach leaflets 270 to inner frame 240, and/or can be used to attach inner assembly 240 to outer assembly 210, such as by connecting inner frame 250 to outer frame 220. In the illustrated embodiment, the posts include openings through which connecting members (such as suture filaments and/or wires) can be passed to couple the posts to other structures.

Inner frame 250 is shown in a fully deformed, i.e. the final, deployed configuration, in side view and bottom view in FIGS. 5 and 6, respectively.

Figure 7:
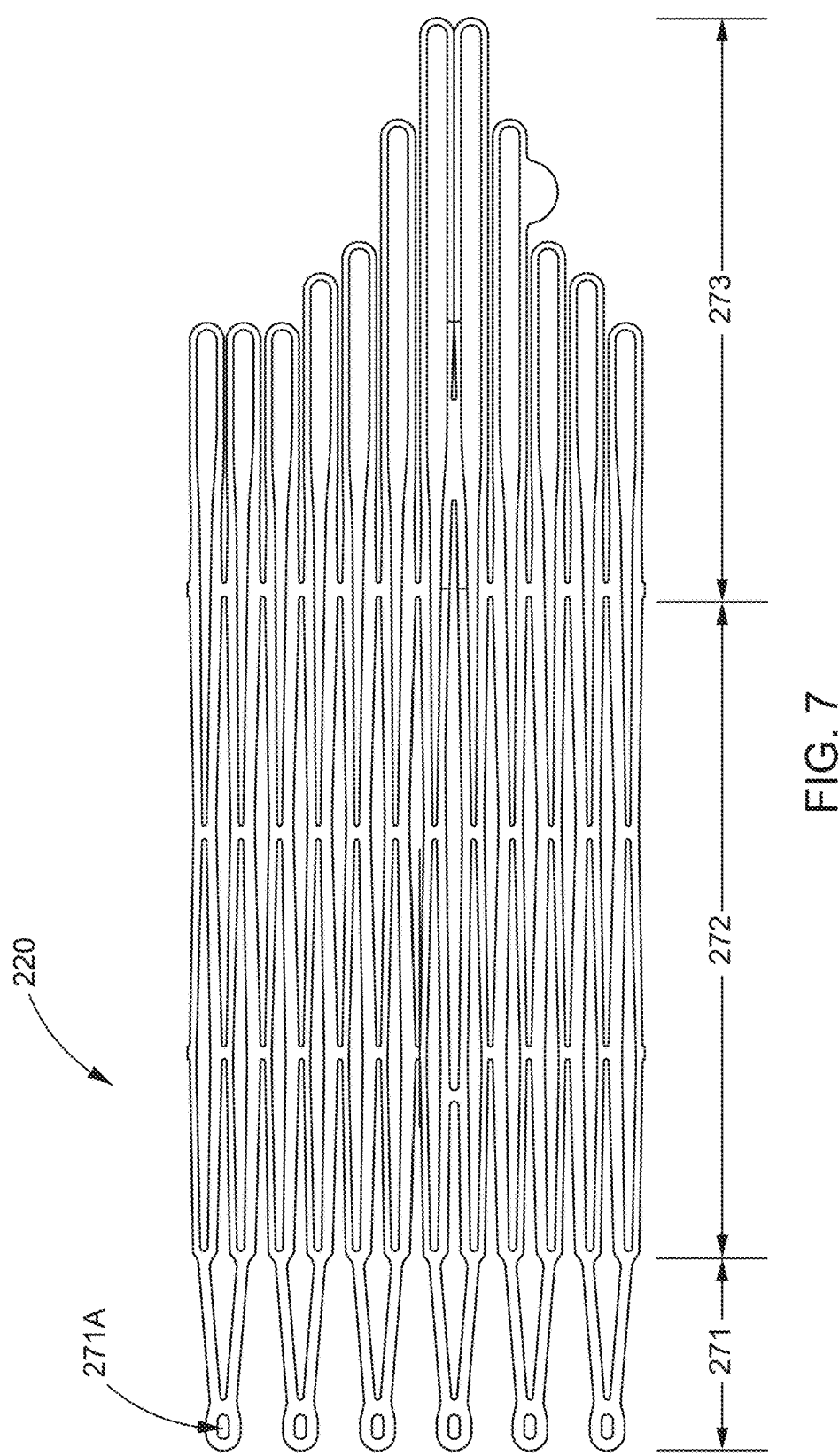
FIG. 7 is an opened and flattened view of the outer frame of the valve of FIGS. 1-3, in an unexpanded configuration.
Figure 8:
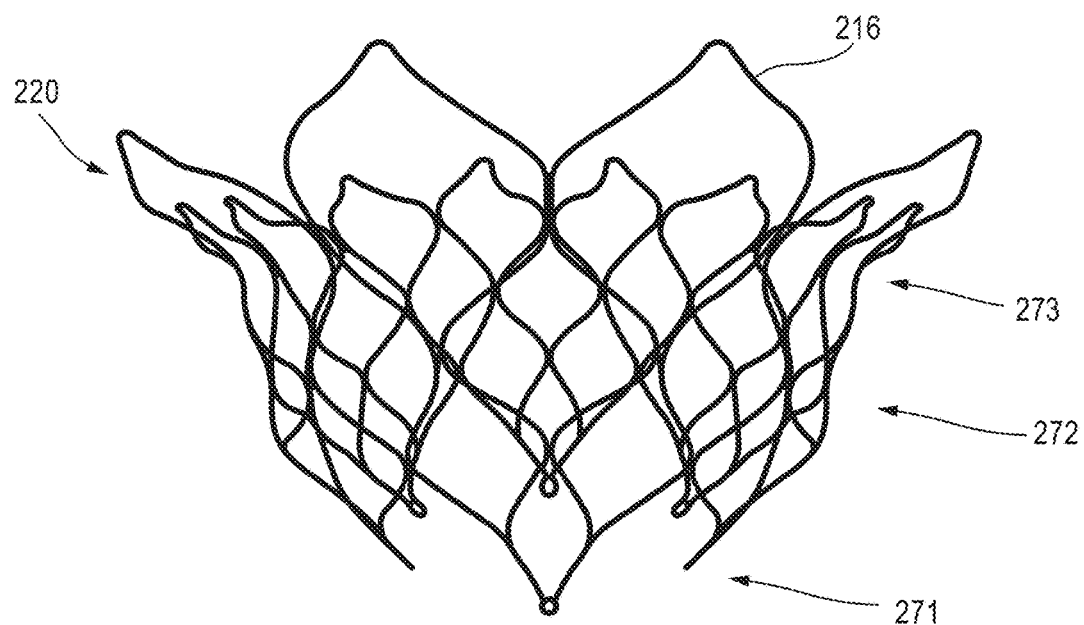
FIGS. 8 and 9 are side and top views, respectively, of the outer frame of FIG. 7 in an expanded configuration.
Figure 9:
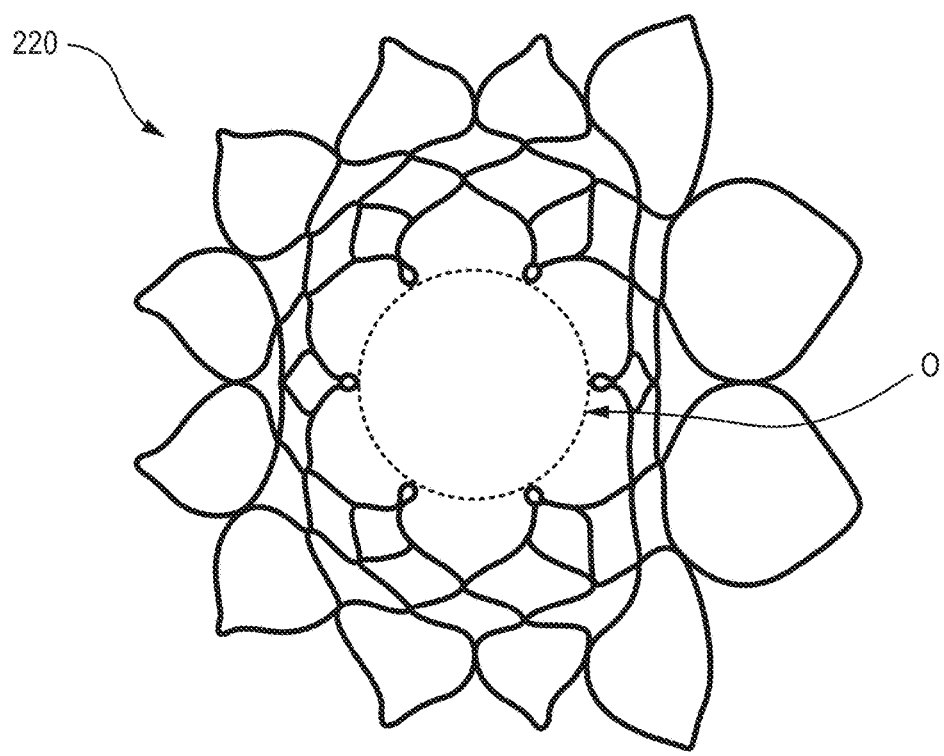

Outer frame 220 of valve 200 is shown in more detail in FIGS. 7-9. In this embodiment, outer frame 220 is also formed from a laser-cut tube of Nitinol®. Outer frame 220 is illustrated in FIG. 7 in an undeformed, initial state, i.e. as laser-cut, but cut and unrolled into a flat sheet for ease of illustration. Outer frame 220 can be divided into an outer frame coupling portion 271, a body portion 272, and a cuff portion 273 (which includes the atrium or free end portion 216), as shown in FIG. 7. Outer frame coupling portion 271 includes multiple openings or apertures, such as 271A, by which outer frame 220 can be coupled to inner frame 250, as discussed in more detail below.

Outer frame 220 is shown in a fully deformed, i.e. the final, deployed configuration, in side view and top view in FIGS. 8 and 9, respectively. As best seen in FIG. 8, the lower end of outer frame coupling portion 271 forms a roughly circular opening (identified by "O" in FIG. 9). The diameter of this opening preferably corresponds approximately to the diameter of body portion 242 of inner frame 250, to facilitate coupling of the two components of valve 200.

Figure 10:
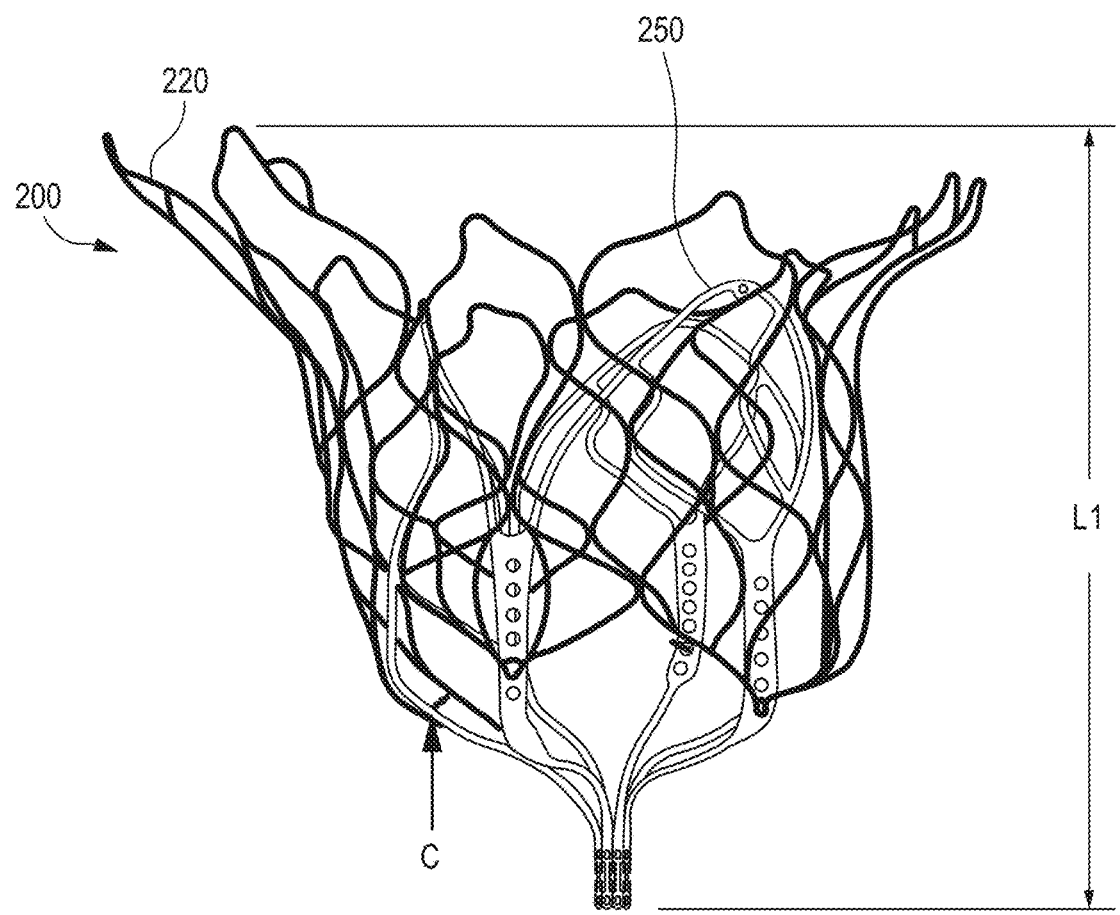
FIGS. 10-12 are side, front, and top views of an assembly of the inner frame of FIGS. 4-6 and the outer frame of FIGS. 7-9.
Figure 11:
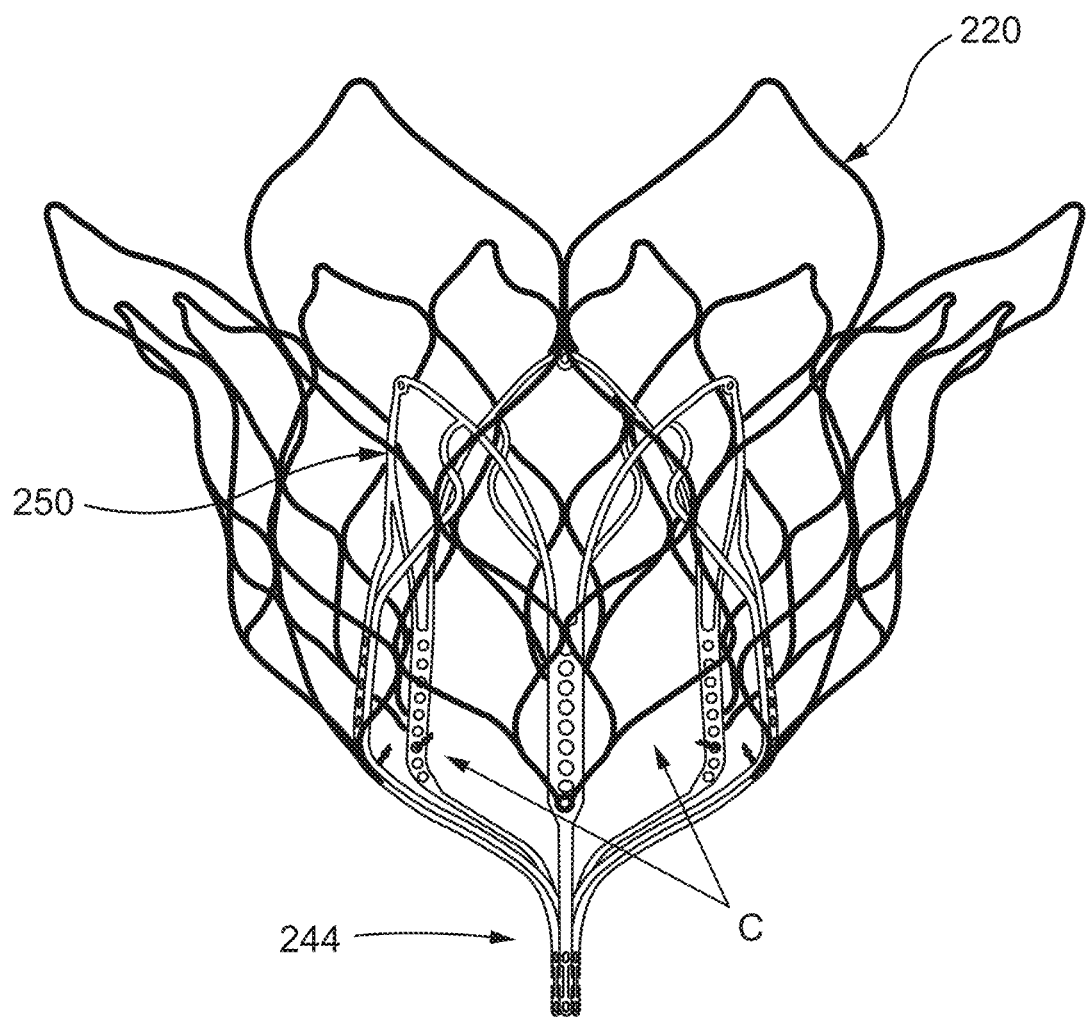
Figure 12:
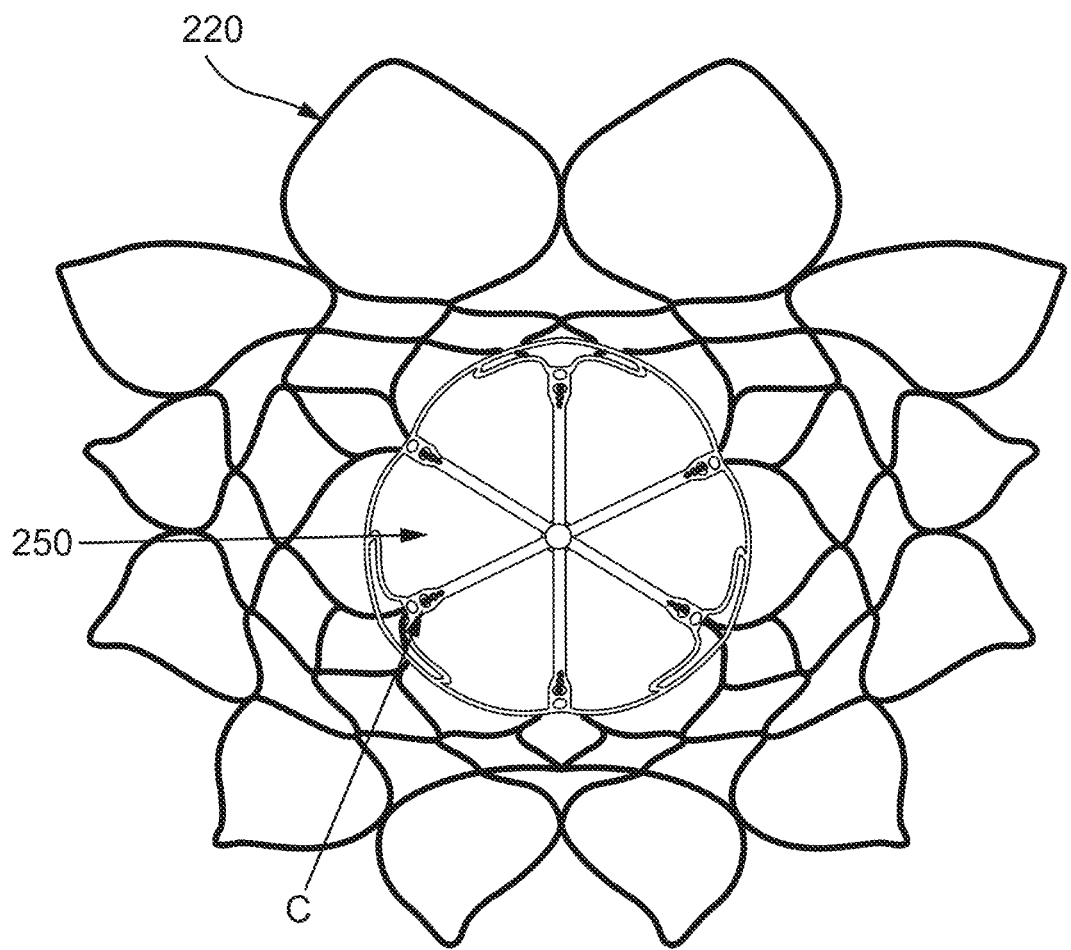

Outer frame 220 and inner frame 250 are shown coupled together in FIGS. 10-12, in front, side, and top views, respectively. The two frames collectively form a structural support for a prosthetic valve such as valve 200. The frames support the valve leaflet structure (e.g., leaflets 270) in the desired relationship to the native valve annulus, support the coverings (e.g., outer covering 230, inner covering 232, outer covering 260) for the two frames to provide a barrier to blood leakage between the atrium and ventricle, and couple to the tether (e.g., tether assembly 290) (by the inner frame 250) to aid in holding the prosthetic valve 200 in place in the native valve annulus by the tether connection to the ventricle wall. The outer frame 220 and the inner frame 250 are connected at six coupling points (representative points are identified as "C"). In this embodiment, the coupling points are implemented with a mechanical fastener, such as a short length of wire, passed through an aperture (such as aperture 271A) in outer frame coupling portion 271 and corresponding openings in inner frame coupling portion 245 (e.g., longitudinal posts, such as post 242A) in body portion 242 of inner frame 250. Inner frame 250 is thus disposed within the outer frame 220 and securely coupled to it.

As described above, various apparatus, systems and methods are described herein for limiting or preventing LVOT obstruction and SAM in conjunction with an implanted prosthetic valve (e.g., prosthetic mitral valve) such as, for example, the prosthetic valve 200 described above. Details regarding the various different approaches to limit or prevent LVOT obstruction and SAM are described below with reference to specific embodiments.

Figure 13:
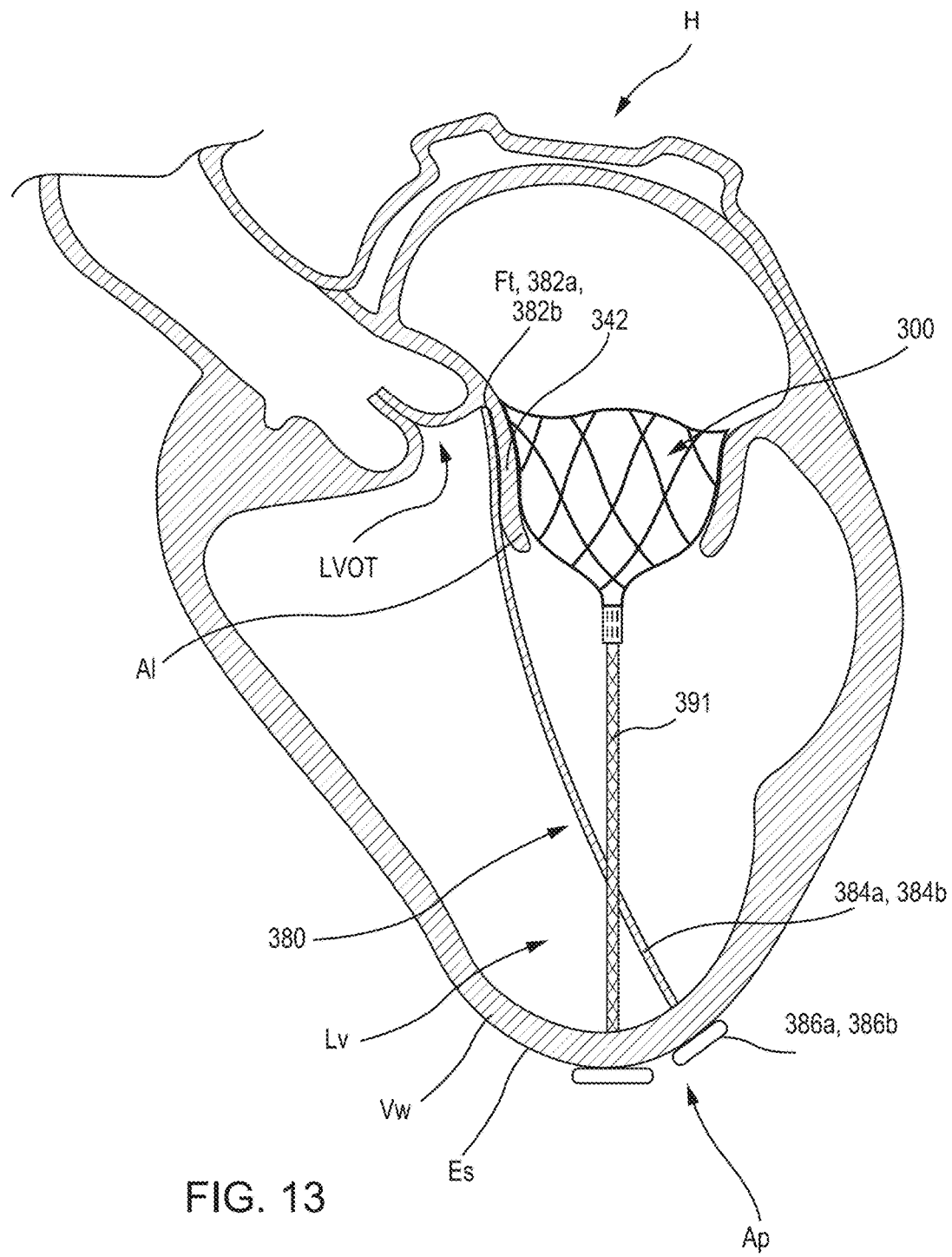
FIGS. 13 and 14 are cross-sectional front and side views, respectively, of a heart having a prosthetic mitral valve and a tether-anchor apparatus implanted therein, according to an embodiment.
Figure 14:
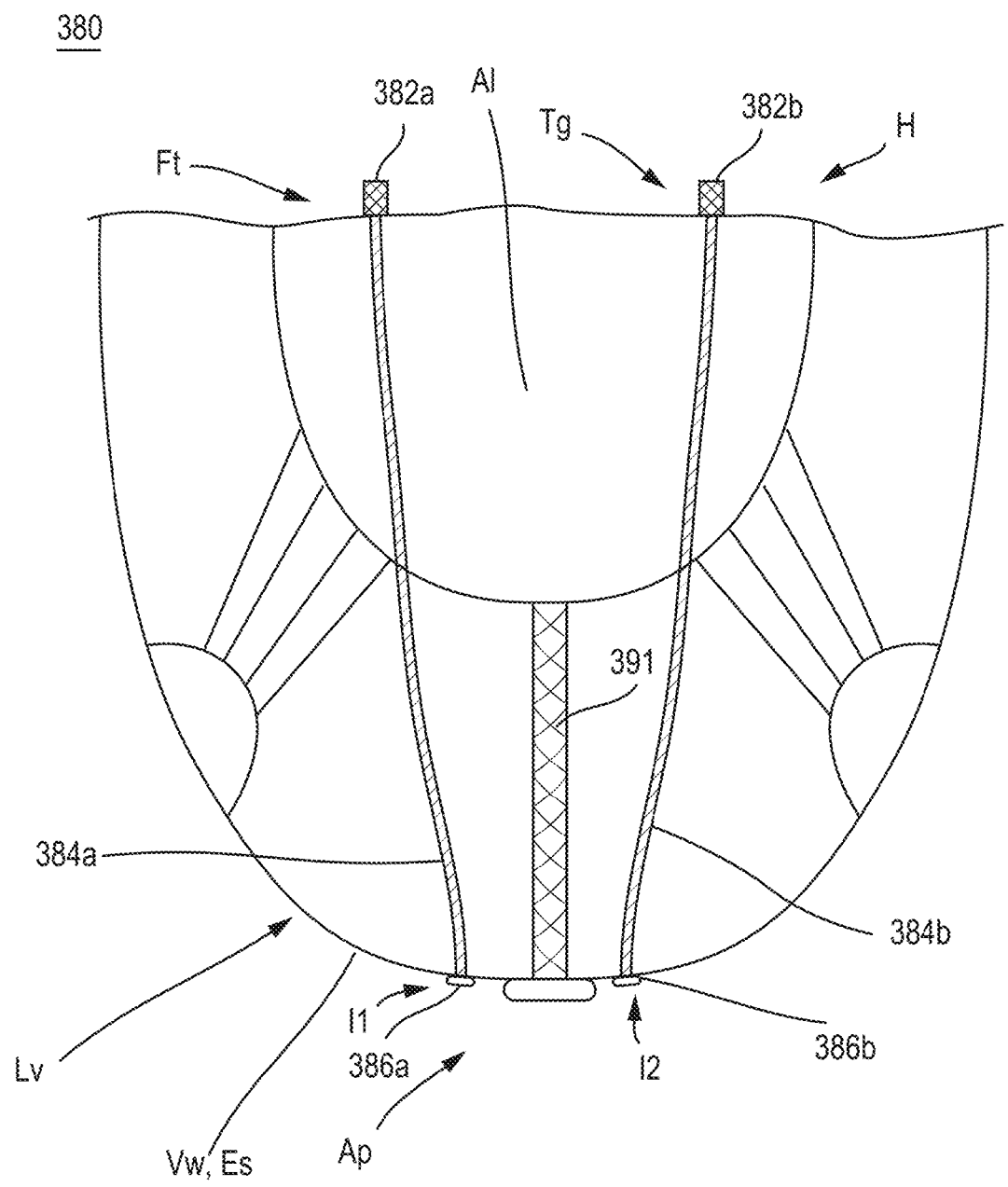

In some embodiments, a method includes implantation of one or more tether-anchors into a fibrous trigone of a native mitral valve of a patient. FIGS. 13 and 14 illustrate in cross-sectional front and side views, respectively, a portion of a heart with such a tether-anchor and a prosthetic mitral valve implanted therein, according to an embodiment. When implanted, the tether-anchor 380 is configured to bias the anterior native valve leaflet A1 of the heart H towards the prosthetic mitral valve 300 and away from the LVOT, thereby preventing or otherwise limiting obstruction by the anterior native valve leaflet A1 of the LVOT. Similarly stated, when implanted, the tether-anchor 380 can immobilize the anterior native valve leaflet A1 of the heart H in a suitable position away from the LVOT. In some embodiments, when implanted, the tether-anchor 380 is configured to exert a force on the native mitral valve apparatus sufficient to modify or reshape the geometry of the native mitral valve apparatus, the left ventricle Lv, and/or LVOT to enhance functioning of the heart H.

The tether-anchor 380 includes a first tether 384a with a first anchor 382a coupled to a distal end portion of the first tether 384a, and a first apical pad 386a coupled to a proximal end portion of the first tether 384a. The tether-anchor further includes a second tether 384b with a second anchor 382b coupled to a distal end portion of the second tether 384b, and a second apical pad 386b coupled to a proximal end portion of the second tether 384b. The prosthetic valve 300 can be constructed the same as or similar to the prosthetic valve 200 described above, and can function in a similar manner. For example, as shown in FIGS. 13 and 14, the prosthetic valve 300 can be coupled to a tether 391 extending from the valve 300 through the left ventricle Lv and out an incision in the apical region of the heart H, to aid in holding the prosthetic valve 300 in place in the native valve annulus.

The tether-anchor 380 can, for example, be implanted percutaneously. In some instances, for example, appropriate incisions can be made in the apex region Ap of the heart H, and the tether-anchor 380 can then be introduced into the left ventricle Lv of the heart H and advanced (e.g., via a delivery device such as a delivery catheter) in such a manner to contact the fibrous trigone Ft adjacent to the LVOT. More specifically, the first anchor 382a and the second anchor 382b can be delivered and coupled to the fibrous trigone Ft (adjacent to the anterior native leaflet) of the native mitral valve (see e.g., FIG. 14). As shown, with the first anchor 382a and the second anchor 382b coupled to the fibrous trigone Ft, the first tether 384a and the second tether 384b can extend proximally from the anchors 382a, 382b, through the left ventricle LV and the incisions in the apex region Ap of the heart H, and be disposed outside the heart H and against the epicardial surface Es of the ventricular wall Vw. With the proximal end portion of the first tether 384a extending through a first incision I1 in the apex region Ap of the heart H, the first apical pad 386a can be secured to the proximal end portion of the first tether 384a and tightened against the epicardial surface Es of the ventricular wall Vw. Similarly, with the proximal end portion of the second tether 384b extending through a second incision I2 in the apex region Ap of the heart H, the second apical pad 386b can be secured to the proximal end portion of the second tether 384b and tightened against the epicardial surface Es of the ventricular wall Vw.

In this manner, as shown, the tether-anchor 380 can be implanted such that the native valve leaflet A1 (e.g., A2 leaflet) of the native mitral valve is disposed between the first tether 384a and the second tether 384b, and the body portion 342 of the valve 300. As such, the tether-anchor 380 can bias the native anterior leaflet towards the body portion 342 of the valve 300 and away from the LVOT, thereby preventing or otherwise limiting obstruction by the native valve leaflet A1 of the LVOT. Further, in some instances, the apical pads 386a, 386b can be adjusted (e.g., tightened) to apply tension on the tethers 384a, 384b (and in turn the anchors 382b, 382b and fibrous trigone Ft). Such tension can be applied to modify or reshape the geometry of the native mitral valve, the left ventricle Lv, and/or LVOT to enhance functioning of the heart. In some instances, prior to introducing into the heart a prosthetic valve, the tether-anchor can be introduced into the heart and implanted therein, and used to apply tension to the appropriate native structures to limit or prevent risk of SAM. Such manipulation of the appropriate native structures before introducing and implanting a prosthetic heart valve can reduce risk of complications or complexity which would be present if a prosthetic valve was implanted and suitably situated within a native annulus prior to reshaping or altering the native valve apparatus.

A tether-anchor can include an anchor having any shape, size and material suitable for anchoring tethers to a fibrous trigone of a heart. In some embodiments, a tether-anchor can include a helical anchor. FIG. 15A illustrates in side view a tether-anchor 480 having a helix coil shaped anchor, according to an embodiment. The tether-anchor 480 can be constructed the same as or similar to, and function the same as or similar to the tether-anchor 380 described above. Thus, some details regarding the tether-anchor 480 are not described below. It should be understood that for features and functions not specifically discussed, those features and functions can be the same as or similar to the tether-anchor 380.

As shown in FIG. 15A, the tether-anchor 480 includes an anchor 482 having a helix coil shape coupled to an apical pad 486 via a tether 484. Similar to previous embodiments, the tether-anchor 480 can be implanted percutaneously and through an incision made in the apex region of the heart. The tether-anchor 480 can further be introduced into the left ventricle of the heart and advanced such that the helix coil shape anchor 482 contacts a fibrous trigone (e.g., adjacent to the native mitral valve anterior leaflet). The tether-anchor 480 can be advanced further such that a distal end (e.g., a distal tip) of the anchor 482 pierces and screws into the fibrous trigone such that the anchor 482 is secured within a portion of the fibrous trigone. The tether-anchor 480 can be rotated or otherwise manipulated to advance the anchor 482 into the fibrous trigone a distance sufficient to secure the anchor 482 into the fibrous trigone such that the anchor 482 will remain anchored (i.e., not dislodge from the fibrous trigone) in response to forces generated during operation of the heart.

In other embodiments, a tether-anchor can include an expandable barbed anchor. FIG. 15B illustrates in side view a tether-anchor 580 having an expandable barbed anchor, according to an embodiment. The tether-anchor 580 can be constructed the same as or similar to, and function the same as or similar to the tether-anchors 280, 380 described above. Thus, some details regarding the tether-anchor 580 are not described below. It should be understood that for features and functions not specifically discussed, those features and functions can be the same as or similar to the tether-anchors 280, 380.

As shown in FIG. 15B, the tether-anchor 580 includes an expandable barbed anchor 582 coupled to an apical pad 586 via a tether 584. Similar to previous embodiments, the tether-anchor 580 can be implanted percutaneously and through an incision made in the apex region of the heart. More specifically, the tether-anchor 580 can be implanted through the incision when the anchor 582 is in its low-profile, smaller diameter, non-expanded configuration (not shown). With the anchor 582 in its non-expanded configuration, the anchor 582 can be introduced through a small incision in the apex region of the heart. The tether-anchor 580 can further be introduced into the left ventricle of the heart and advanced such that anchor 582 contacts a fibrous trigone (e.g., adjacent to the native mitral valve anterior leaflet). The tether-anchor 580 can be advanced further such that a distal end (e.g., a distal tip) of the anchor 582 pierces and enters the fibrous trigone. Once the anchor 482 is disposed at least partially within the fibrous trigone, the anchor 582 can be actuated or otherwise manipulated to change its configuration from the non-expanded configuration to an expanded configuration. In the expanded configuration, barbs of the anchor 482 can expand within the fibrous trigone to secure the anchor 482 therein.

Figure 16:
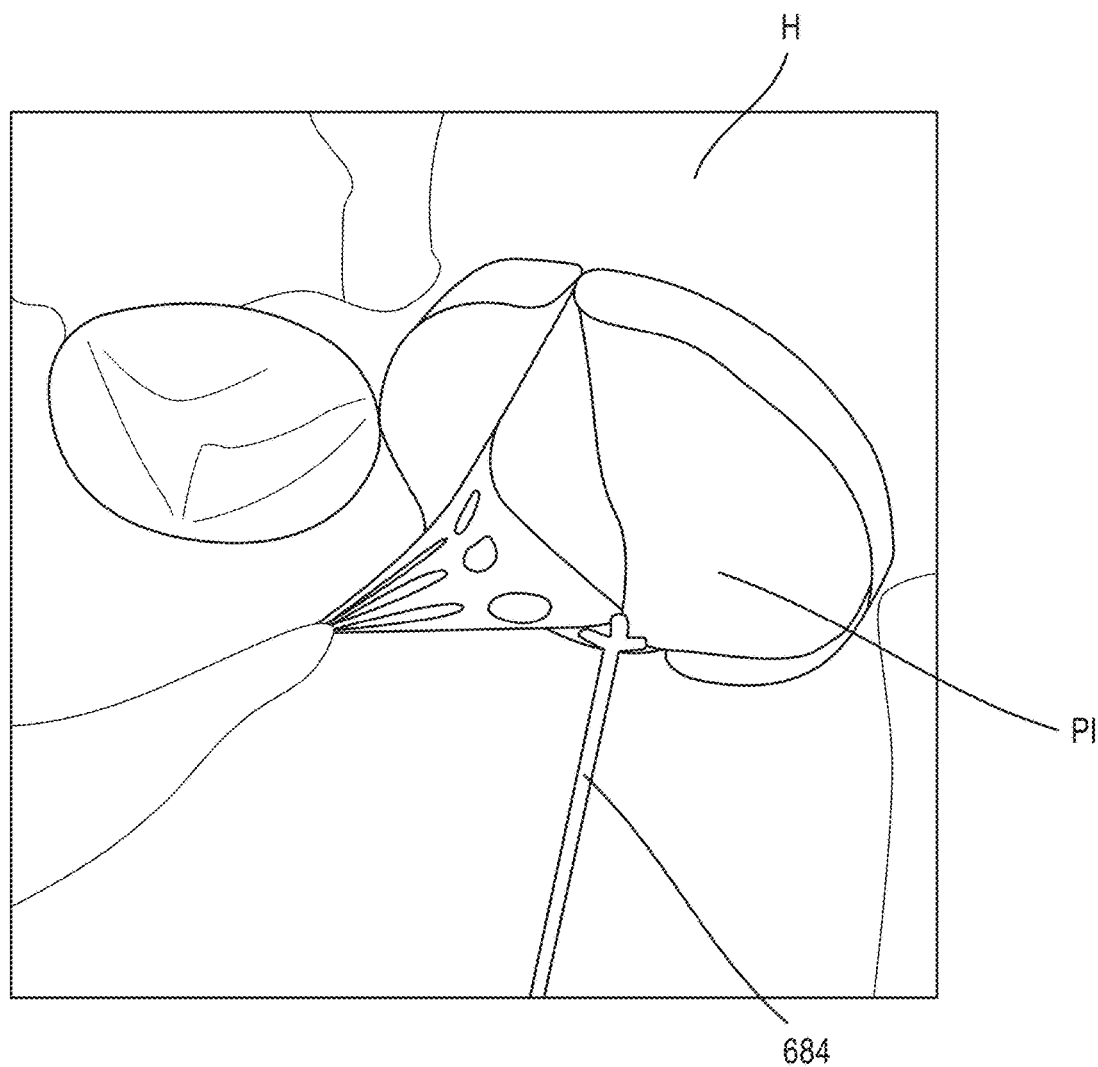
FIG. 16 is a perspective view of a portion of a heart having a tether-anchor apparatus implanted therein, according to an embodiment.

Instead of or in addition to securing a tether-anchor to a fibrous trigone, as discussed in previous embodiments, in some embodiments, a method includes anchoring a tether to one or more native leaflets (e.g., a native mitral valve anterior leaflet) to modulate the one or more native leaflets and relieve SAM. Similar to adjusting mitral valve leaflet coaptation to treat patients with mitral valve regurgitation (MR), tethering at prescribed locations within a heart can accomplish native leaflet (e.g., A2 leaflet) modulation and SAM relief. FIG. 16 illustrates a tether 684 anchored to a free-end portion of a native mitral valve posterior leaflet P1 of a heart H, according to an embodiment. Anchoring to a free-end portion of a native valve leaflet in such a manner allows an operator to bias and/or at least partially immobilize the native leaflet away from the LVOT, thereby limiting or preventing issues arising from SAM. Although the tether 684 in FIG. 16 is coupled to the native mitral valve posterior leaflet P1, in other embodiments, a tether can be coupled to a free-end portion of an anterior leaflet. The tether 684 can be made from any material suitable to be implanted within a body of a patient, for example, a standard surgical, non-absorbable suture (e.g., polyimide and/or ePTFE strands). In some embodiments, a method can include tethering and modulating a native leaflet and/or the native valve before implanting a prosthetic valve. In this manner, SAM can be relieved at least in part before implanting and/or seating a prosthetic valve in a native valve annulus.

Figure 17C:
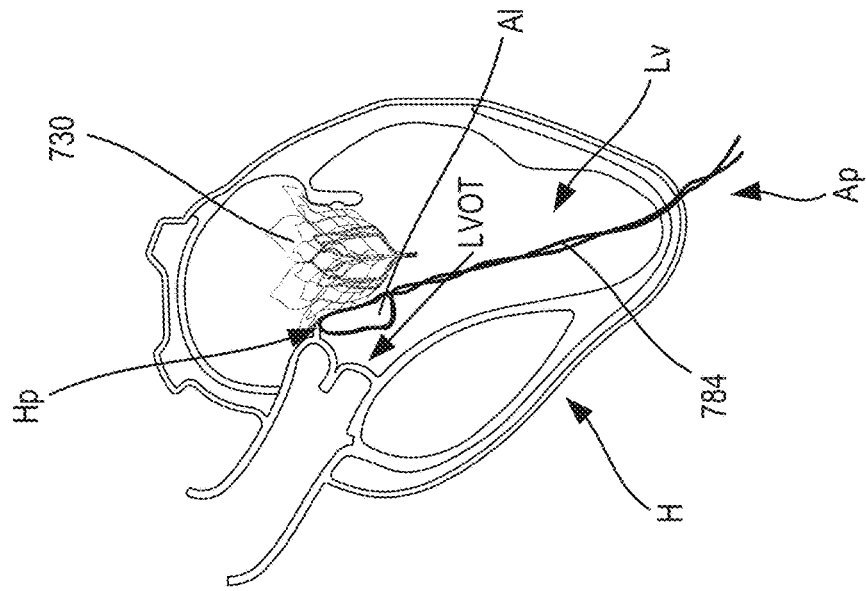
FIG. 17C is a cross-sectional side view of the heart with the leaflet tether apparatus shown in FIGS. 17A and 17B implanted and fully deployed therein, and including the prosthetic mitral valve of FIG. 17B implanted therein.
Figure 17B:
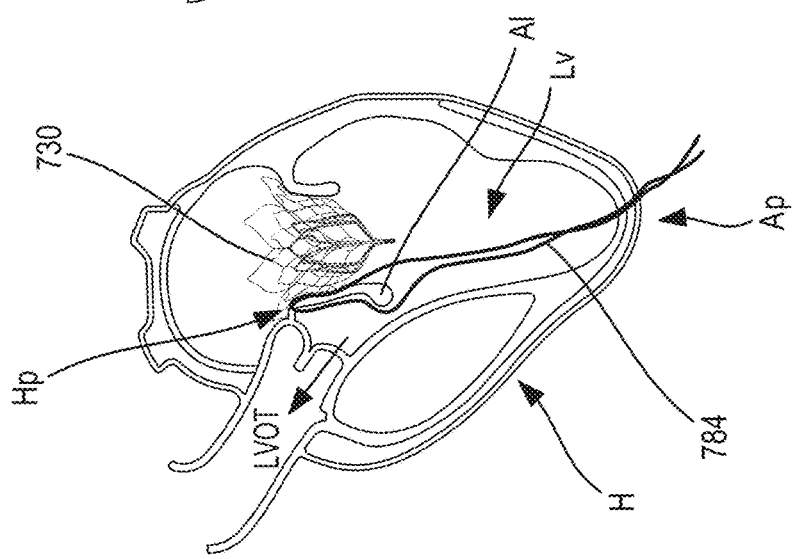
FIG. 17B is a cross-sectional side view of the heart and leaflet tether apparatus shown in FIG. 17A, and including a prosthetic mitral valve implanted therein.
Figure 17A:
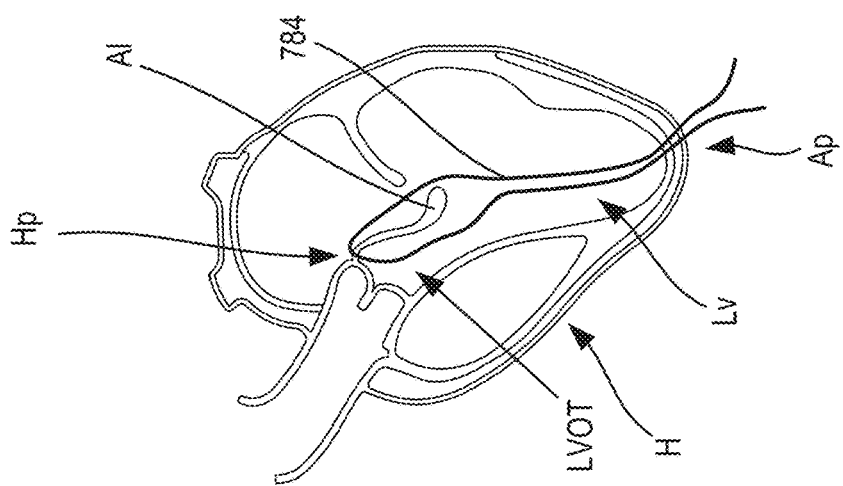
FIG. 17A is a cross-sectional side view of a heart having a leaflet tether apparatus implanted and deployed therein, according to an embodiment.

Instead of or in addition to securing a tether-anchor to a fibrous trigone and/or securing a tether to a free-end portion of a native leaflet, as discussed in previous embodiments, in some embodiments, a method includes anchoring a tether to a hinge-point portion of a native leaflet (e.g., anchoring a tether to the native leaflet near the annulus of the native valve). Securing a tether to a native leaflet in such a manner allows an operator to bias and/or at least partially immobilize the native leaflet away from the LVOT, thereby limiting or preventing issues arising from SAM. FIGS. 17A-17C illustrate a sequence of a tether 784 being anchored to a hinge-portion Hp of a native mitral valve anterior leaflet A1 of a heart H, and FIGS. 17B and 17C further include a prosthetic mitral valve 730 seated within the native mitral valve annulus, according to an embodiment.

In this embodiment, after an appropriate incision has been made in the apex region Ap of the heart H, the tether 784 is introduced into the left ventricle Lv of the heart H and advanced in such a manner so as to contact the hinge-portion Hp of the native anterior leaflet A1 of the heart H. Echocardiography guidance, for example, can be used to assist in the advancement of the tether 784 into the ventricle and into contact with and through the hinge-portion Hp of the anterior leaflet A1 (see e.g., FIG. 17A). With the tether 784 routed through the hinge-point Hp of the anterior leaflet A1, a distal end portion of the tether 784 can extend proximally towards and through the incision, as shown in FIG. 17A. With the tether 784 tethered or looped through and around a portion of the anterior leaflet A1, a prosthetic mitral valve 730 can be introduced and seated with a native annulus of the mitral valve, as shown in FIG. 17B. As discussed with respect to previous embodiments, and as shown in FIG. 17B, when introducing the prosthetic mitral valve 730 to the native annulus, the prosthetic mitral valve 730 may bias or push the native anterior leaflet A1 into the LVOT. To limit or prevent such LVOT obstruction, as shown in FIG. 17C, the method further includes forming a knot with the tether 784 such that a portion of the tether 784 is tightened and/or tensioned about the native anterior leaflet A1, with a remaining portion of the tether 784 extending proximally towards and through the incision in the apex region Ar of the heart H. With the tether 784 tensioned about the native anterior leaflet A1, as shown in FIG. 17C, the tether is manipulated to manipulate and/or bias the native anterior leaflet A1 away from the LVOT and towards the prosthetic mitral valve 730 to reduce or alleviate potential SAM. In some embodiments, before, during or after manipulating the native anterior leaflet A1 using the tether, SAM can be assessed to determine whether additional manipulation of the native anterior leaflet is necessary.

Figure 18:
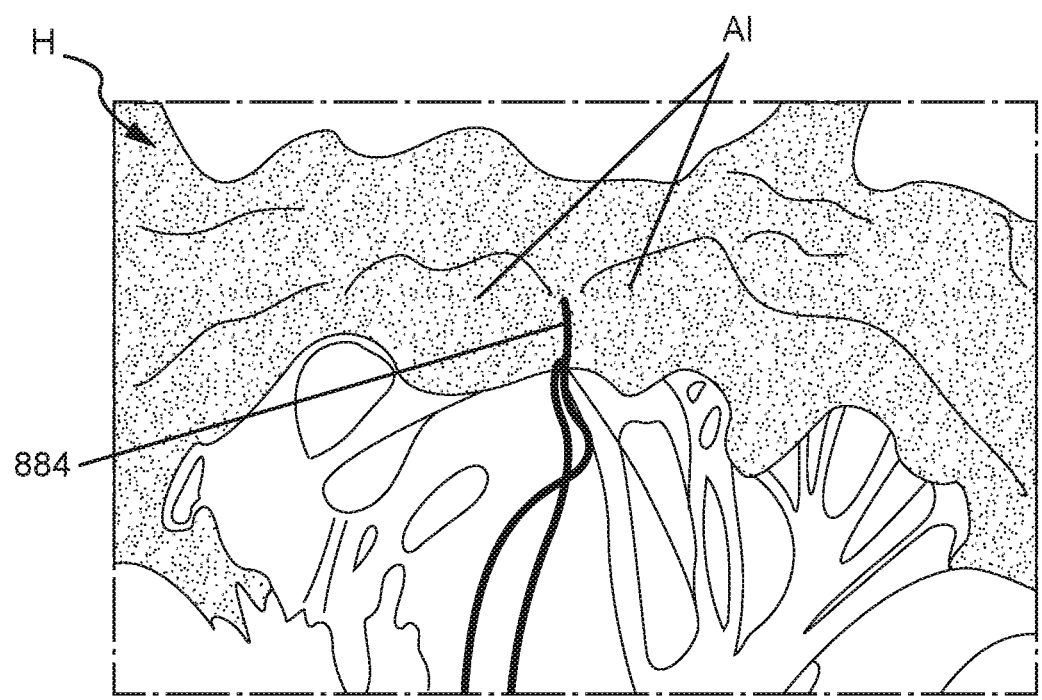
FIG. 18 is a front view of a native heart valve leaflet that has been plicated using a leaflet tether apparatus, according to an embodiment.

Instead of or in addition to securing a tether-anchor to a fibrous trigone and/or securing a tether to a free-end portion or hinge-portion of a native leaflet, as discussed in previous embodiments, in some embodiments, a method includes plicating a leaflet using a tether. FIG. 18 illustrates under gross examination a native mitral valve anterior leaflet A1 plicated using a tether 884. As shown, a portion of the tether 884 is wrapped around a portion of the anterior leaflet A1 and a slip knot is formed. In such a configuration, a free-end of the tether 884 may be pulled proximally to apply tension to the portion of the tether 884 wrapped around the anterior leaflet A1, thereby plicating the anterior leaflet, as shown in FIG. 18. In this manner, at least a portion of the anterior leaflet A1 is tented and/or isolated from the LVOT. In some embodiments, a method can further include securing the free-end of the tether 884 to the apex region (not shown) of the heart H (e.g., using a surgical knot and/or an apical pad) or tacking the free-end of the tether 884 at the apex region (not shown) of the heart H to maintain suitable tension of the tether 884 and plication of the anterior leaflet A1.

In some embodiments, a native anterior leaflet plication method includes introducing into a left ventricle of a heart and implanting therein a double suture through multiple (e.g., two) side portions of a native anterior leaflet. To ensure or otherwise promote the plication of the anterior leaflet is directed away from the LVOT, the method includes first piercing the anterior leaflet at positions radially outward or radially displaced from a center portion or center area of the native mitral valve. In this manner, the anterior leaflet can be plicated in an orientation away from the LVOT.

In some embodiments, a method includes tethering together (e.g., loosely coupled via a tether) a native mitral valve anterior leaflet (e.g., A2 leaflet) and a native mitral valve posterior leaflet (e.g., P2 leaflet). With the tether disposed about the anterior and posterior leaflets ("the leaflets"), appropriate tension is applied to the tether such that (1) the anterior leaflet is at least partially immobilized and/or biased away from the LVOT, and (2) a gap between the leaflets is present to preserve suitable flow therethrough (e.g., flow from the atrium to the ventricle across an implanted prosthetic mitral valve). In some embodiments, a similar method can further include modifying or reshaping the geometry associated with the native mitral valve (e.g., the mitral valve annulus, the left ventricle, the left atrium, the LVOT, and the like) by implanting one or more tethers to and between the native anterior leaflet (e.g., A2 leaflet) and associated papillary muscles and/or a portion of the septal wall.

In some embodiments, a method can include tethering together (e.g., using a loop or lasso) multiple chordae tendineae associated with a native anterior leaflet (e.g., A2 leaflet) to at least partially immobilize the anterior leaflet to limit or prevent LVOT obstruction. In some instances, the tether can be appropriately tightened or cinched when the tether loop is disposed adjacent to or relatively near to the anterior leaflet to at least partially immobilize the anterior leaflet. In other instances, with the tether loop tightened or cinched about the chordae tendineae near the papillary muscles (or otherwise a distance away from the anterior leaflet), the tightened tether loop can be slid distally towards the anterior leaflet to at least partially immobilize the anterior leaflet. In some embodiments, tethers can be delivered and employed in conjunction with a prosthetic valve tether. In this manner, a tether loop can be formed and supported at least in part the prosthetic valve tether.

As described with respect to previous embodiments, in some instances, a native mitral valve anterior leaflet (e.g., an A2 leaflet) may at least partially obstruct the LVOT after a prosthetic mitral valve is implanted and seated within a native mitral valve annulus of a heart, resulting in various undesirable complications (e.g., SAM). Some known procedures include complete removal of a native mitral valve apparatus. Such procedures, however, for example, may alter a volume of the native annulus, resulting in perivalvular leaks (PVL). To preserve the native annulus volume and limit or prevent PVL, and to limit, prevent and/or treat such obstruction and/or SAM when a prosthetic mitral valve is implanted within a patient, in some embodiments, methods can include grasping and/or resecting a portion of the native anterior leaflet to limit or prevent obstruction of flow by the leaflet. A resected native anterior leaflet may promote sufficient flow through the LVOT by allowing flow through the resected space and/or by allowing a portion of the native anterior leaflet to not obstruct flow.

Figure 19A:
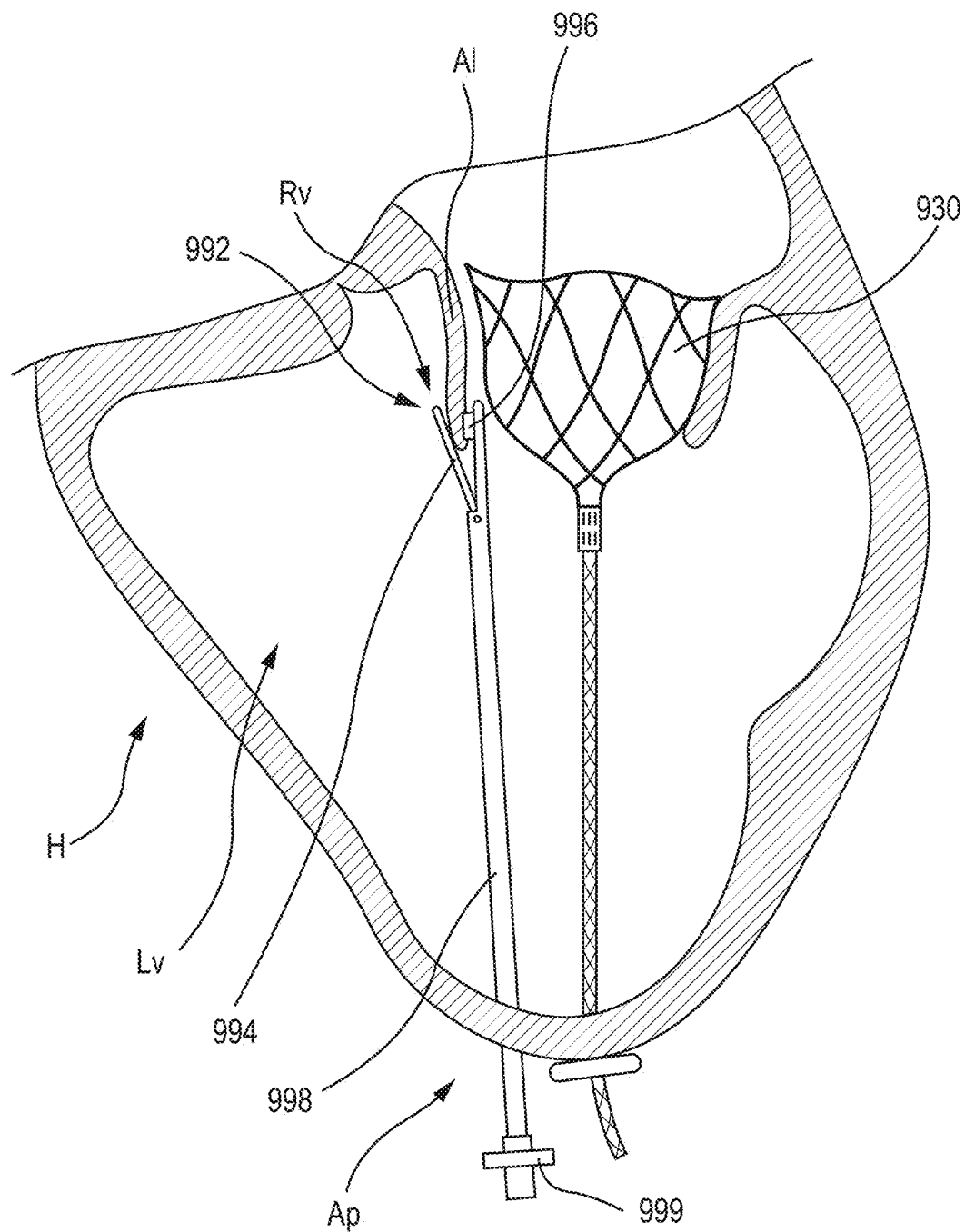
FIG. 19A is a cross-sectional front view of a heart having a prosthetic heart valve and a native heart valve leaflet cutter disposed therein, according to an embodiment.
Figure 19B:
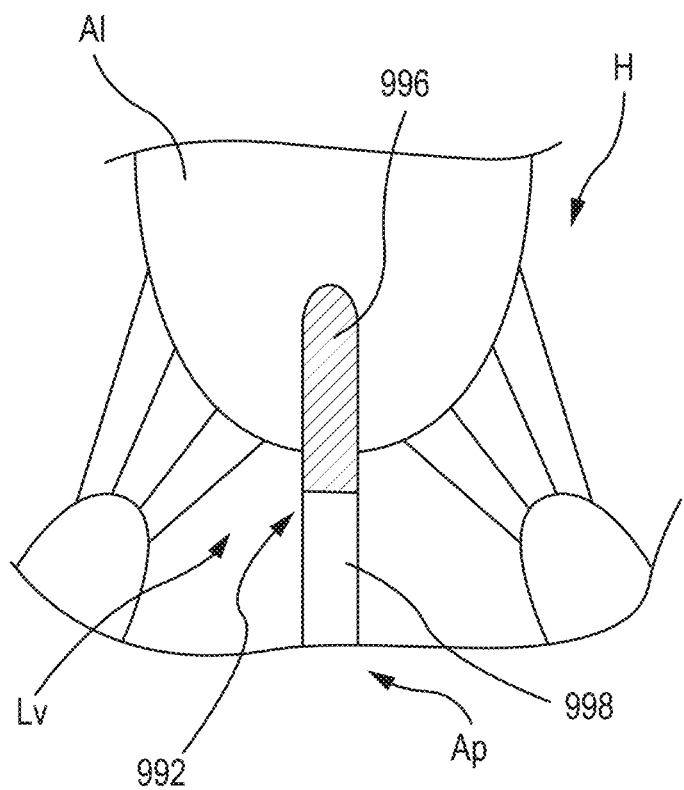
FIG. 19B is a cross-sectional partial side view of the native heart valve leaflet cutter of FIG. 19A, disposed within the heart.

FIGS. 19A and 19B illustrate a portion of a heart in cross-sectional front and side views, respectively, with both a native leaflet cutter 992 in an open configuration and an implanted prosthetic mitral valve 930 (not shown in FIG. 19B) disposed therein, according to an embodiment. In this embodiment, a method includes introducing via an incision in the apical region Ap of a heart H of a patient a native leaflet cutter 992 (also referred to herein as "leaflet cutter"). As shown in FIG. 19A, the leaflet cutter 992 includes a grasper 994 and a cutter 996 coupled to the grasper 994, and an elongate member 998 coupled to and extending from the grasper 994. The cutter 996 is disposed between end portions of the grasper 994 (as shown in FIG. 19A). In this manner, (e.g., during introduction to the heart H of the leaflet cutter 992 and prior to cutting or resecting of the anterior leaflet A1, and/or during removal of the leaflet cutter 992 from the heart H), the cutter 996 can be shielded to limit or prevent undesirable damage or interaction with the heart H. Similarly, the elongate member 998 (e.g., a 6-8 French sheath) has a distal end portion and a proximal end portion, and has a length such that the elongate member 998 extends from at or near the anterior leaflet A1, through the left ventricle Lv of the heart H and through the incision in the apical region Ar of the heart H. The leaflet cutter 992 further includes a handle 999 (FIG. 19A) coupled to the proximal end portion of the elongate member 998. The handle 999 includes an actuator (not shown) operably coupled to the grasper 994 and configured to actuate the grasper from an open configuration, in which the grasper 994 defines a leaflet receiving volume Rv such that at least a portion of the native mitral valve anterior leaflet A1 can be disposed in the leaflet receiving volume Rv, to a closed, grasping or cutting configuration (not shown), in which the grasper 994 at least in part closes or reduces the volume of the leaflet receiving volume Rv. In this manner, with the grasper 994 in its open configuration, the leaflet cutter 992 can be advanced distally such that at least a portion of the anterior leaflet A1 is disposed in the leaflet receiving volume Rv of the grasper 994. With the anterior leaflet A1 disposed within the leaflet receiving volume Rv of the grasper 994, the actuator can be manipulated (e.g., an operator can manipulate the handle 999 to actuate the actuator) to transition the grasper 994 to its closed configuration. As the grasper 994 transitions from its open configuration to its closed configuration, the cutter 996 can contact and pierce, cut and/or resect a portion of the anterior leaflet A1.

In some instances, the leaflet cutter 992 can be used to make a single cut or resection in a portion of the anterior leaflet A1, while in other instances, the leaflet cutter 992 can be used to make multiple cuts or resections in the anterior leaflet A1. In this manner, one or more cuts or resections of the anterior leaflet A1 effectively defines one or more additional cusps in the leaflet A1. As such, each cusp of the leaflet A1 can interact, move or articulate independent from one another, thereby limiting or reducing blood flow and/or LVOT obstruction by the leaflet A1. Similarly, such cuts or resections of the leaflet A1 may desirably reduce interaction by the leaflet A1 with blood flow during late diastole/systole by reducing in flow effect during diastole and venturi during systole. Forming discrete portions on the free edge of the leaflet A1 may allow additional blood flow through the resected space, thereby limiting and/or reducing SAM. Further, cutting or resecting a leaflet A1 in this manner allows for reduction of SAM without delivering a permanent implant for purposes of managing the anterior leaflet A1.

In some instances, the anterior leaflet A1 can be resected at or near a center portion of the anterior leaflet A1 to limit or prevent undesirable damage to or cutting of a native chordae or sub-annular structure.

Although the leaflet cutter 992 is shown and described using transapical delivery methods, in other embodiments, a leaflet cutter can be introduced into the heart via other delivery methods, such as, for example, a transfemoral delivery method.

In some embodiments, a leaflet cutter includes markers (e.g., radiopaque and/or echo lucent markers) to assist an operator of the leaflet cutter with alignment of the leaflet cutter and cutting and resection of the native leaflet. In some embodiments, a leaflet cutter further includes markers (e.g., radiopaque and/or echo lucent marker) configured to indicate how much of an anterior leaflet has been captured, cut and/or resected.

Figure 20B:
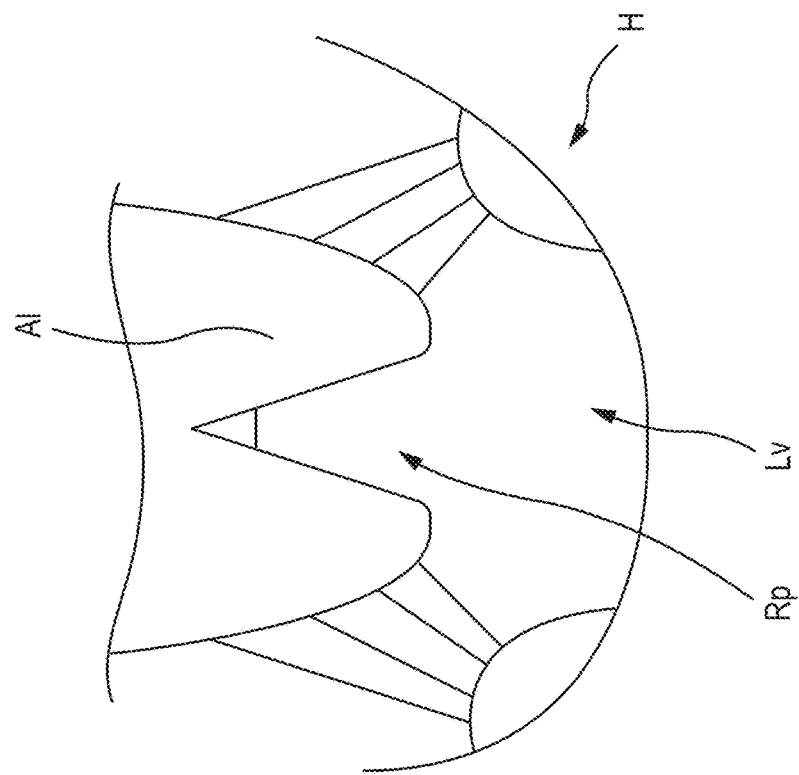
FIG. 20B is a cross-sectional side view of a resected native valve leaflet.
Figure 20A:
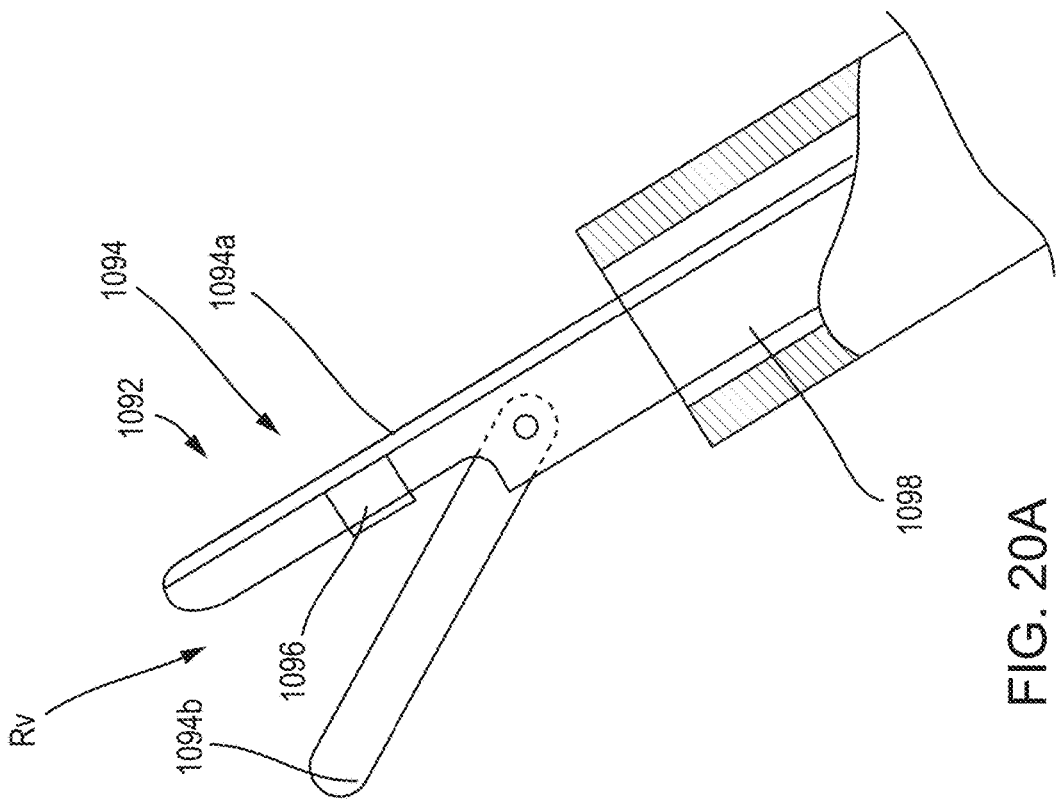
FIG. 20A is a side view of a distal portion of a native heart valve leaflet cutter, in an open configuration, according to an embodiment

In some embodiments, a leaflet cutter can be configured to grasp a native anterior leaflet and cut or resect a portion of the anterior leaflet when the leaflet cutter is advanced linearly within the heart. FIG. 20A illustrates a distal portion of a leaflet cutter 1092 in an open configuration, and FIG. 20B illustrates a native anterior leaflet A1 that has been resected by the leaflet cutter 1092, according to an embodiment. The leaflet cutter 1092 can be constructed the same as or similar to, and function the same as or similar to the leaflet cutter 992 described above. Thus, some details regarding the leaflet cutter 1092 are not described below. It should be understood that for features and functions not specifically discussed, those features and functions can be the same as or similar to the leaflet cutter 992.

In this embodiment, as shown in FIG. 20A, the leaflet cutter 1092 includes a grasper 1094 having a first arm 1094a and a second arm 1094b configured to rotate or pivot relative to the first arm 1094a. The first arm 1094a is coupled and in a fixed position relative to an elongate member 1098 of the leaflet cutter 1092. The first arm 1094a and the second arm 1094b collectively define therebetween a native leaflet receiving volume Rv configured to receive at least a portion of a native leaflet. As shown in FIG. 20A, a cutter 1096 is coupled to the first arm 1094a and configured to cut, pierce and/or resect a portion of the native leaflet A1. Similar to as described in previous embodiments, a method can include introducing transapically or transfemorally into a native left ventricle Lv of a heart H of a patient the leaflet cutter 1092. The leaflet cutter 1092 can be advanced distally within the left ventricle Lv of the heart H such that at least a portion of the anterior leaflet A1 is disposed in the leaflet receiving volume Rv of the grasper 1094. With a portion of the anterior leaflet A1 disposed within the leaflet receiving volume Rv of the grasper 1094, an actuator (not shown) of the leaflet cutter 1092 can be actuated to articulate or rotate the second arm 1094b relative to the first arm 1094a to grasp or at least temporarily and/or partially retain (or limit movement of) a portion of the anterior leaflet A1 between the first arm 1094a and the second arm 1094b. Further, with a portion of the anterior leaflet A1 disposed within the leaflet receiving volume Rv of the grasper 1094, the leaflet cutter 1092 can be advanced distally and linearly such that the cutter 1096 contacts, pierces, cuts and/or resects a portion of the anterior leaflet A1 (e.g., the cutting can be initiated at or near a surface of the anterior leaflet A1). In this manner, an operator can control the linear movement of the leaflet cutter 1092 to control a length or amount of cut or resection of the anterior leaflet A1. As discussed with respect to previous embodiments, a resected portion Rp (see FIG. 20B) of the anterior leaflet A1 can allow blood flow therethrough, thereby limiting and/or reducing potential LVOT and/or SAM.

Figure 21C:
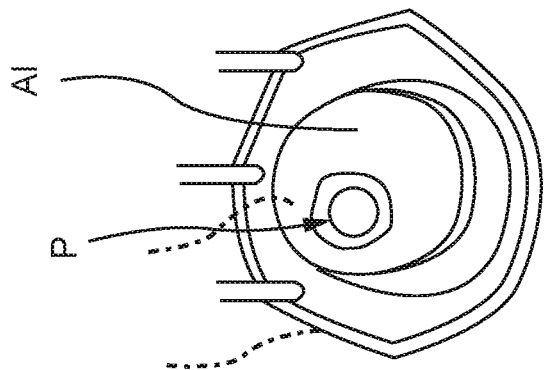
FIG. 21C is a detailed view of a punctured native valve leaflet.
Figure 21B:
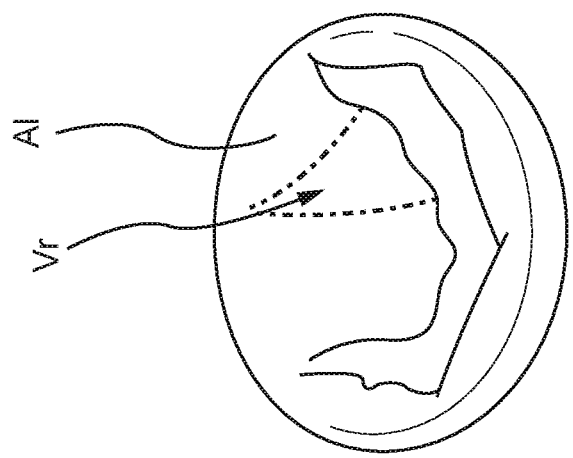
FIG. 21B is a detailed view of a V-shaped resection of a native valve leaflet.
Figure 21A:
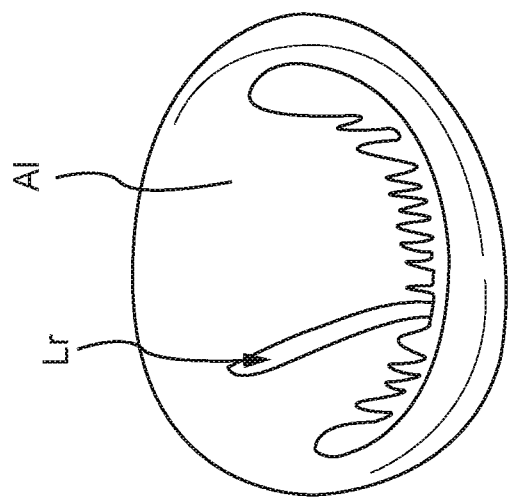
FIG. 21A is a detailed view of a linear resection of a native valve leaflet.

As discussed above with respect to previous embodiments, resecting, cutting, or otherwise manipulating a native leaflet (e.g., an A2 native anterior mitral valve leaflet) can limit, prevent, and/or treat LVOT obstruction and/or SAM. FIGS. 21A-21C illustrate various examples of how an A2 native anterior mitral valve leaflet can be manipulated to limit, prevent, and/or treat LVOT obstruction and/or SAM. Such leaflet manipulation can be accomplished, for example, by methods and apparatus discussed above with respect to previous embodiments, e.g., using the leaflet cutter 992, leaflet cutter 1092, etc. In some instances, for example, cutting, resecting or puncturing the leaflet, as shown in FIGS. 21A-21C, can be accomplished using endoscopic forceps. The endoscopic forceps, for example, can be introduced transapically to a heart. In yet further instances, for example, arthroscopic forceps could be used with echocardiographic guidance to cut, resect or otherwise manipulate a leaflet.

FIG. 21A illustrates in top view a single linear resection Lr of an A2 native anterior mitral valve leaflet A1, according to an embodiment. Although in this embodiment the leaflet incurs only a single linear resection, in other embodiments a leaflet can incur multiple linear resections. FIG. 21B illustrates in top view a V-shaped or triangular-shaped resection Vr of an A2 native anterior mitral valve leaflet A1, according to an embodiment. FIG. 21C illustrates in top view a puncture P of an A2 native anterior mitral valve leaflet A1, according to an embodiment. Although in this embodiment the leaflet incurs only a single puncture, in other embodiments a leaflet can incur multiple punctures. In some embodiments, an incision (e.g., whether a linear resection, a v-shaped resection, or a puncture) can be located at or aligned with the LVOT, thereby at least partially incapacitating the valve leaflet while allowing the native valve annulus to remain substantially intact. In some embodiments, a method may include any combination of the leaflet manipulation discussed and described with respect to FIGS. 21A-21C. For example, in some embodiments, a method can include resecting an A2 native anterior mitral valve leaflet at one or more locations (see e.g., FIGS. 21A and 21B), and puncturing the A2 native anterior mitral valve leaflet in one or more locations (see e.g., FIG. 21C). In some instances, determining the type(s) of leaflet manipulation may depend at least in part on a patient's particular anatomy and/or susceptibility to LVOT obstruction and/or SAM.

In addition to or instead of manipulating a native heart valve leaflet as described in previous embodiments, in some embodiments a prosthetic mitral valve apparatus and/or system can include a leaflet manipulation component. For example, in some embodiments, a prosthetic mitral valve can include one or more leaflet clips (e.g., monolithically formed with the prosthetic mitral valve or formed separately and then coupled to the prosthetic mitral valve) configured to capture (e.g., grab, coupled to, connect with, bias, pierce, enclose, etc.) a native valve leaflet. For example, when a prosthetic heart valve is implanted into the native annulus of the heart, the leaflet clip can capture the native valve leaflet (e.g., the A2 mitral valve leaflet) such that the native leaflet is disposed between the leaflet clip and a body portion of the prosthetic valve. In this manner, the native leaflet can be selectively positioned, for example, outside of the LVOT, thereby limiting and/or reducing LVOT obstruction, SAM, undesirable blood flow turbulence, eddies, or similar interference by the native leaflet during operation of the prosthetic heart valve. Similarly, over time as the native leaflet stiffens, due to calcification for example, or otherwise changes form, the leaflet clip can retain the native leaflet in a desirable position such that a desirable blood flow profile is maintained. Various embodiments of a leaflet management system, including a leaflet manipulation component, are described herein. Other embodiments of apparatus, systems, and methods for securing, controlling, capturing, or otherwise manipulating native heart valve leaflets when a prosthetic heart valve is delivered to or disposed in a native annulus of an atrioventricular valve of a heart are described in U.S. Patent Application Publication No. 2016/0008131, the entire disclosure of which is incorporated herein by reference in its entirety.

Figure 22A:
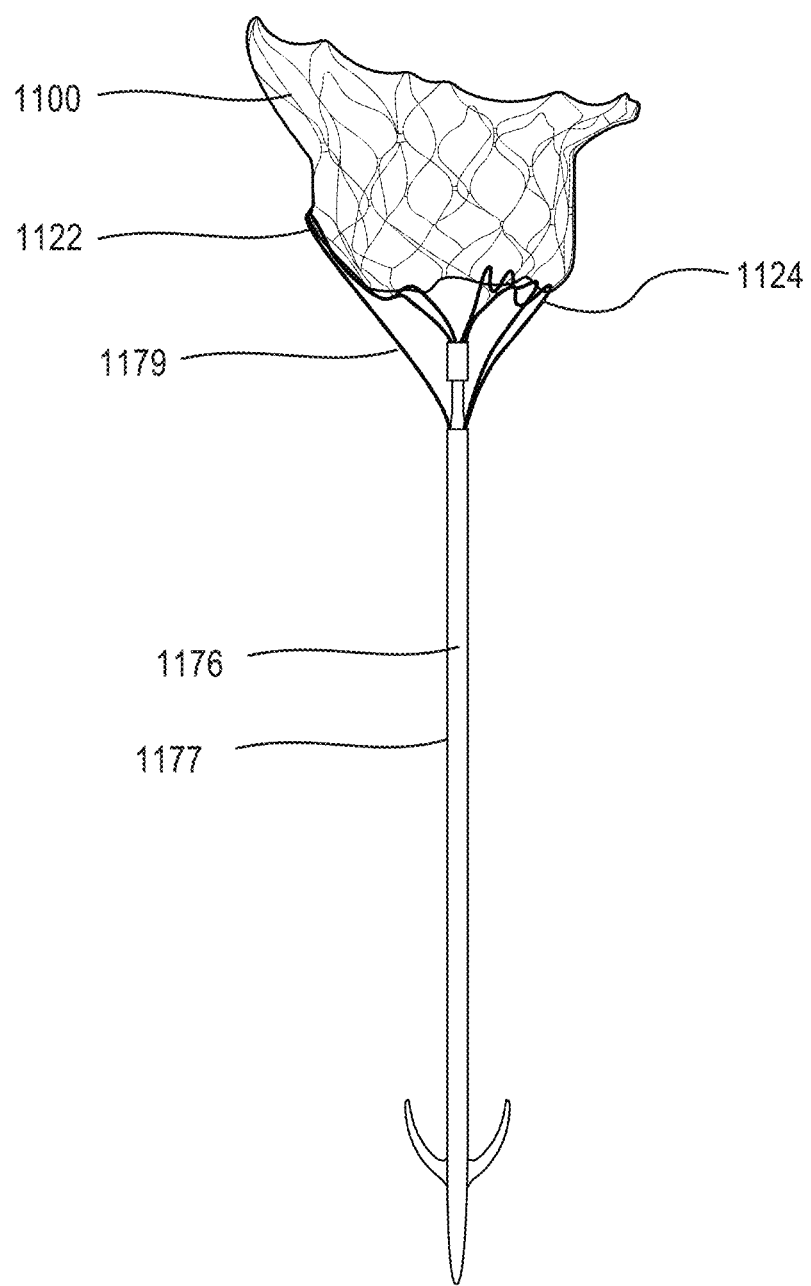
FIG. 22A is a front view of a prosthetic heart valve and a native leaflet manipulation system, according to an embodiment.
Figure 22B:
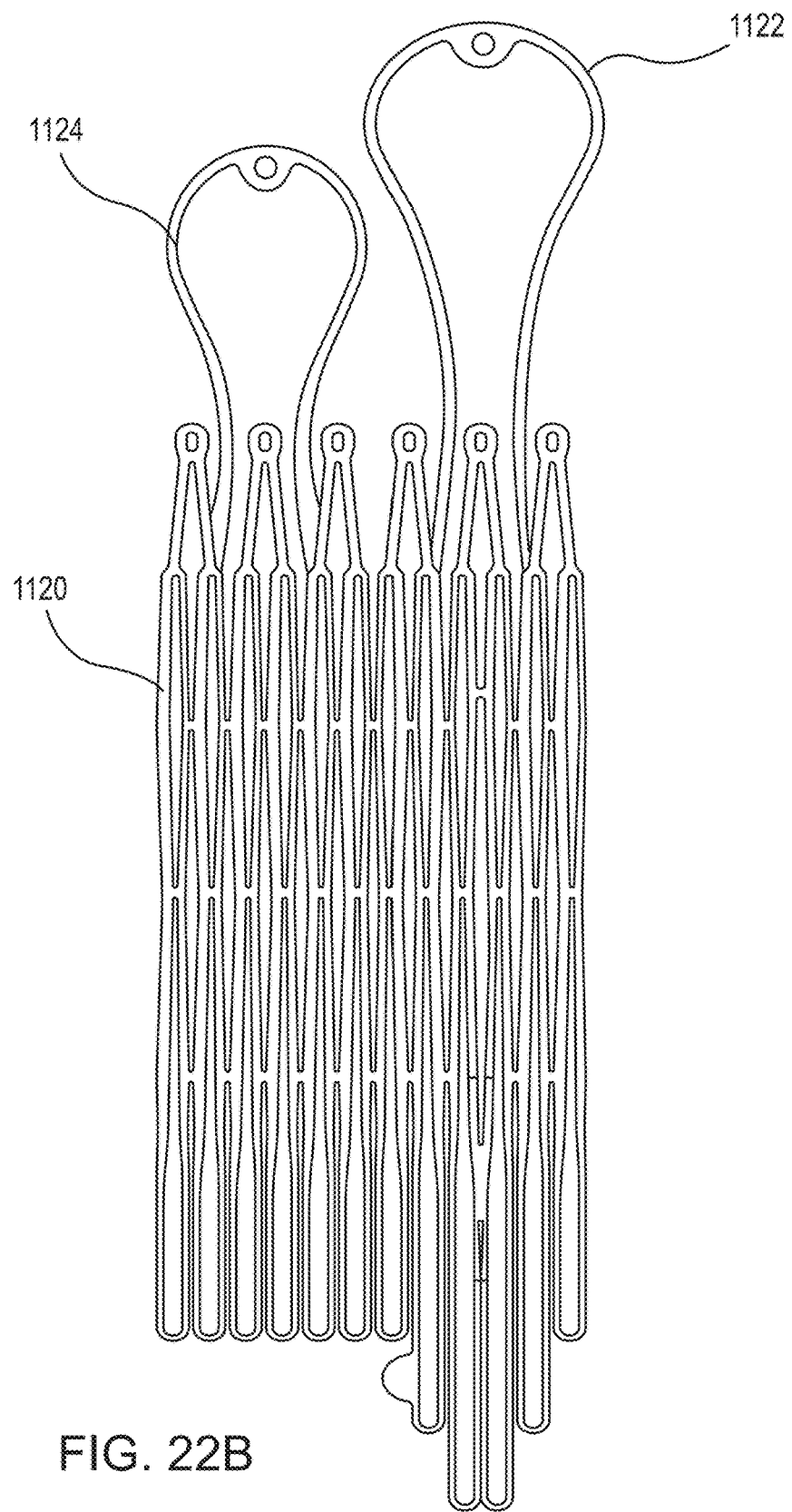
FIG. 22B is an opened and flattened view of the outer frame of the valve of FIG. 22A, in an unexpanded configuration.

FIG. 22A illustrates in front view a native leaflet manipulation system including a prosthetic heart valve 1100, a tether 1176, a delivery sheath 1177, a first leaflet clip 1122 and a second leaflet clip 1124 (also referred to herein collectively as "leaflet clips"), and a control element 1179; and FIG. 22B illustrates an outer frame 1120 of the valve 1100, according to an embodiment. As shown, the outer frame 1120 of the prosthetic heart valve 1100 defines the first leaflet clip 1122 and second leaflet clip 1124. In this embodiment, the outer frame 1120 is formed from a laser-cut tube of Nitinol®. The outer frame 1120 is illustrated in FIG. 22B in an undeformed, initial state, i.e., as laser-cut, but cut and unrolled into a flat sheet for ease of illustration. The valve 1100, including the outer frame 1120, can be constructed the same as or similar to the prosthetic valves described above (e.g., valve 200, outer frame 220).

The leaflet clips 1122, 1124 can be configured to be transitioned between a first configuration in which the prosthetic valve can be inserted into a heart, and a second configuration in which the leaflet clips 1122, 1124 are disposed to capture native valve leaflets between the leaflet clips 1122, 1124 and the prosthetic mitral valve body 1142 when the body 1142 is disposed in a native annulus of a mitral valve of a heart. In some embodiments, leaflet clips can be identical, while in other embodiments, leaflet clips can be configured differently, e.g., to capture and engage with different leaflets or portions of a patient's heart. In this embodiment, the leaflet clips 1122, 1124 are sized differently from each other. Specifically, the first leaflet clip 1122 is configured to capture an A2 mitral valve leaflet, and the second leaflet clip 1124 is configured to capture a P2 mitral valve leaflet.

The control element 1179 is operably coupled to the leaflet clips 1122, 1124 and has a length sufficient to extend from the leaflet clips 1122, 1124 through a ventricle of the heart and out a wall of the ventricle when the valve 1100 is disposed in the native annulus of the heart valve. The control element 1179 is further configured to allow a user to transition the leaflet clips 1122, 1124 from their first configuration to their second configuration (either individually or simultaneously) when the valve 1100 is disposed in the native annulus of the heart valve.

With the leaflet clips 1122, 1124 incorporated with the outer frame 1120, as shown, the prosthetic valve 1100, including the leaflet clips 1122, 1124, can be delivered within the delivery sheath 1177 to the mitral annulus of a heart of a patient. With the valve 1100 seated or disposed in the mitral annulus, the control element 1179 can be actuated to selectively manipulate the leaflet clips 1122, 1124 between configurations. In this manner, an operator of the control element 1179 can monitor and control a rate of movement or release of the leaflet clips 1122, 1124 to promote proper capture of the native leaflets.

Figure 23:
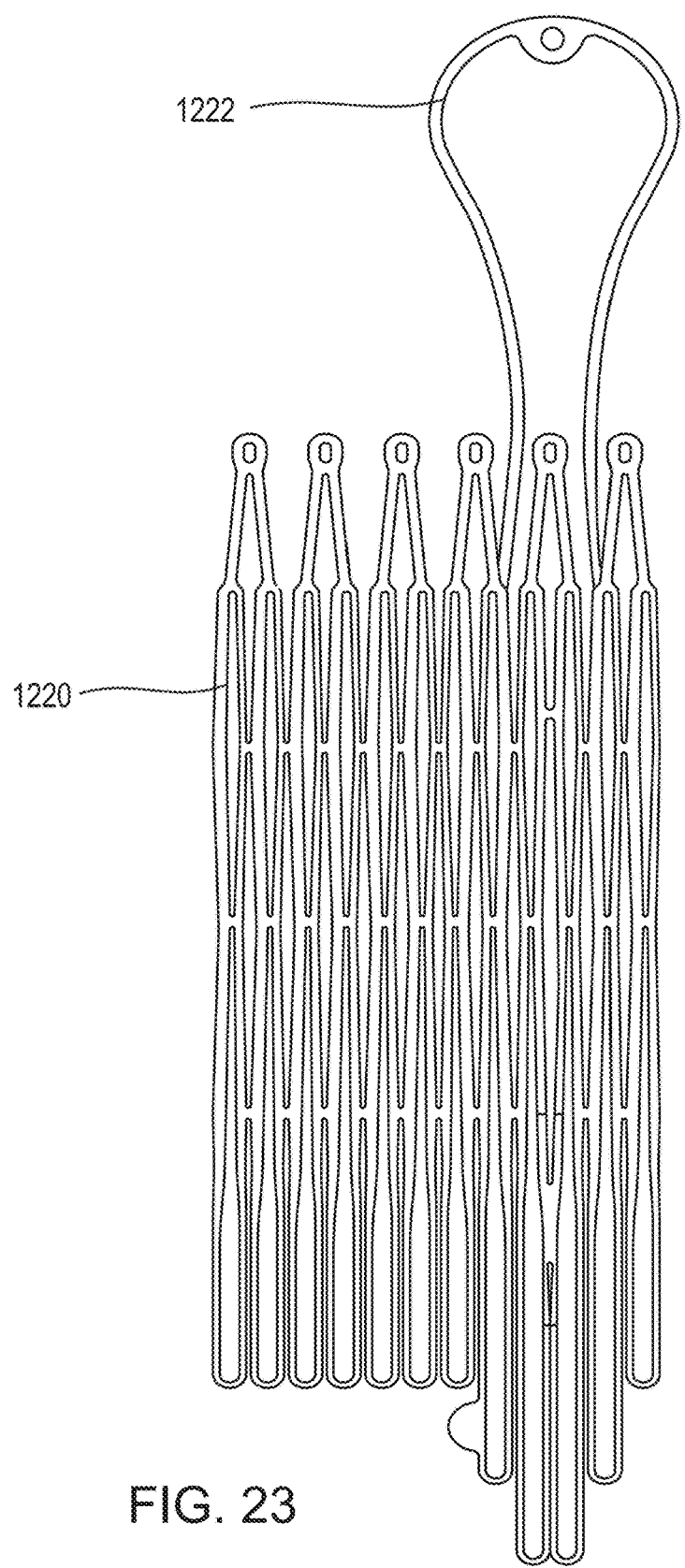
FIG. 23 is an opened and flattened view of an outer frame of a prosthetic valve, in an unexpanded configuration, according to an embodiment.

In some embodiments, a prosthetic valve and leaflet management system can include only a single leaflet clip (e.g., to capture a native A2 leaflet). For example, FIG. 23 illustrates an outer frame 1220, according to an embodiment. The outer frame 1220 can be constructed similar to the outer frame 1120 described above, but defines only a single leaflet clip 1222. In this embodiment, the outer frame 1220 is formed from a laser-cut tube of Nitinol®. The outer frame 1220 is illustrated in FIG. 23 in an undeformed, initial state, i.e., as laser-cut, but cut and unrolled into a flat sheet for ease of illustration. The leaflet clip 1222 can function the same as or similar to the leaflet clips described above (e.g., the leaflet clips 1122, 1124). For example, in use, the leaflet clip 1222 can be implanted within a heart and manipulated to capture a native A2 leaflet.

In some embodiments, instead of or in addition to incorporating leaflet clips into the prosthetic valve, one or more leaflet clips can be delivered and deployed into a heart of a patient via a tether (e.g., similar to tether 1176). For example, the one or more leaflet clips can be delivered in an over-the-wire (OTW) manner in which the leaflet clips can be slid across the tether. In this manner, the leaflet clips can be delivered when desired, e.g., simultaneously delivered with the prosthetic valve, or delivered after the prosthetic valve is delivered and deployed. In other embodiments, an OTW leaflet clip system could be rotated into engagement with a native A2 leaflet, e.g., the leaflet clip could move in a twisting motion to capture the native leaflet. In yet further embodiments, a rotational clip system can be used to target and capture or lasso one or more native chordae tendineae that are attached to the native leaflet (e.g., the A2 leaflet). The native chordae tendineae can be manipulated in this manner to limit or restrict movement of the leaflet to which the chordae tendineae is attached.

Figure 24A:
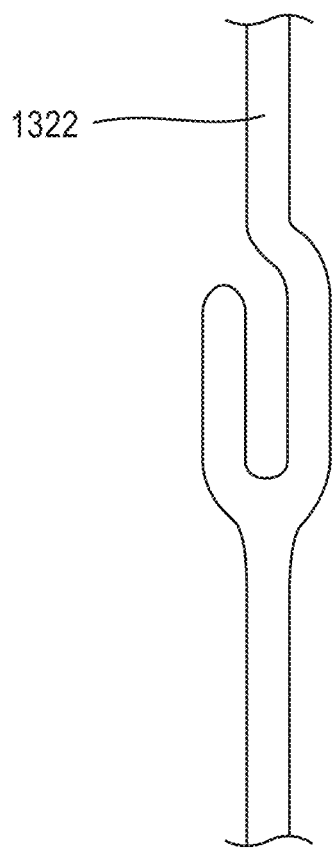
FIG. 24A is a side view of a leaflet barb, according to an embodiment.
Figure 24B:
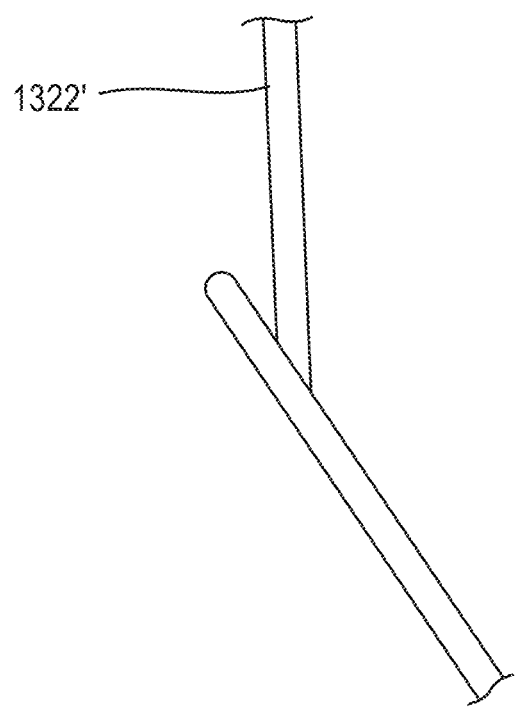
FIG. 24B is a side view of a leaflet barb, according to an embodiment.

Instead of or in addition to using leaflet clips to secure native valve leaflets to or against a prosthetic valve body, barbs, pins, screws and/or sutures can be used for such securement. FIGS. 24A and 24B illustrate two examples of a leaflet capture barb portion 1322, 1322', respectively configured to engage with or otherwise secure a native valve leaflet to a prosthetic heart valve. In some embodiments, the barb portion 1322, 1322' can be monolithically formed (e.g., located at or near struts of the valve) with an outer frame of a prosthetic valve (not shown), while in other embodiments, the barb portion 1322, 1322' can be formed separately and activated as desired. For example, with the barb portion 1322, 1322' formed separately from the prosthetic valve, the barb portion 1322, 1322' can be disposed within a volume defined or partially enclosed by the prosthetic valve, and can extend radially away from a center of the prosthetic valve and through spaces defined by the struts of the outer frame (e.g., and below a covering of the valve). The barb portion 1322, 1322' can be activated (e.g., manipulated to engage with a native leaflet) in any suitable manner, e.g., via application of tension, employing threads, and/or advancing a suitably configured curved shaft containing the barbs within the prosthetic valve body. As a further example, in some instances, a suction force or other suitable force can be applied to encourage engagement of the native leaflet with the barb portion 1322, 1322' to secure the native leaflet to the prosthetic valve.

Figure 25:
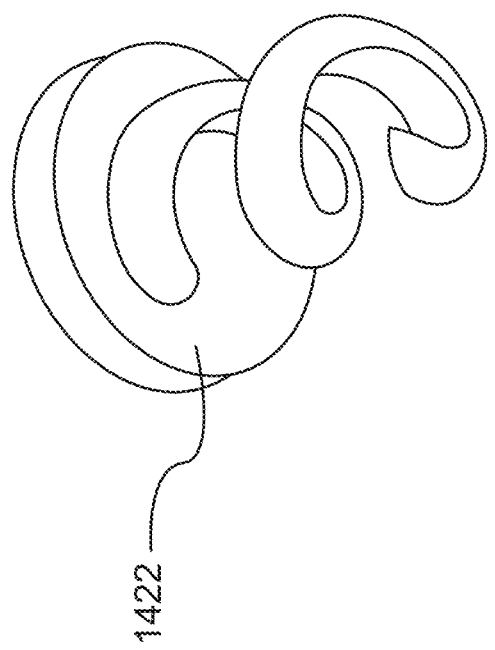
FIG. 25 is a side view of a heart valve leaflet coil, according to an embodiment.

Instead of or in addition to securing a native leaflet with one or more barbs, as described above, in some embodiments, one or more coil screws or pins could be used to secure a native leaflet to the prosthetic valve. FIG. 25 illustrates a coil screw 1422 configured to engage or pierce a native leaflet and/or valve structure below the mitral annulus plane, thereby promoting immobilization of the native leaflet to limit or prevent LVOT obstruction or SAM. The coil screw 1422 can be formed with or coupled to a prosthetic valve similar to as described with respect to the barb portions 1322, 1322' above.

In some embodiments, one or more pins could be delivered and employed through a specialized catheter to accomplish native leaflet securement. In yet further embodiments, a pressurized (e.g., high pressure) balloon catheter could be inflated within the LVOT to ease or enable delivery of one or more pins through a native leaflet. Further, in some embodiments, a suture could be used to secure a native leaflet to a prosthetic valve by passing the suture through the native leaflet with a needle (e.g., a curved needle), and extending or looping the suture through or around portions (e.g., struts) of the prosthetic valve. With the suture extending through the leaflet and engaged with the prosthetic valve, the suture can be secured, e.g., via a knot or other suitable securement mechanism. In such embodiments, in some instances, a non-linear or curved delivery sheath can be used to delivery and/or employ the suture.

Instead of or in addition to the native leaflet securement methods and apparatus discussed above with respect to previous embodiments, in some embodiments, a substance, such as a bio-adhesive, for example) can be applied to a prosthetic heart valve (e.g., to an outer surface of the prosthetic valve). The bio-adhesive on the valve can promote engagement with and securement of the native leaflet away from the LVOT. Further, with the prosthetic valve deployed within the native annulus of a heart, over time, native tissue ingrowth at and around the connection between the leaflet and the prosthetic valve can provide further adherence and securement between the same.

Instead of or in addition to the native leaflet securement methods and apparatus discussed above with respect to previous embodiments, in some embodiments, a native heart valve (e.g., the native mitral valve) can be altered to prevent or treat SAM. In some embodiments, native valve alteration can occur prior to prosthetic valve implantation. In this manner, LVOT obstruction or SAM can be treated without interference with an implanted prosthetic heart valve. In other embodiments, native valve apparatus alteration can occur subsequent to prosthetic valve implantation.

In some embodiments, ablation can be used and applied to alter a native heart valve; for example, ablation can be applied to one or more native valve leaflets, septal wall, papillary muscles, chordae and/or the like. Ablation, for example, can include cryogenic energy and/or radio frequency energy. Ablation can be used to denature native valve architecture, resulting in changes to native valve tissue characteristics. Tissue exposed to RF energy and/or cryogenic conditions, for example, can become necrotic and replaced by fibrotic mass. Such changes may limit or prevent SAM, for example, by resulting in significant tissue contractility and increased chordal tension. Further, in some embodiments, instead of or in addition to RF energy or cryogenic conditions, absolute alcohol and/or hydrogen peroxide can be used to denature native heart architecture and promote tissue necrosis. Thus, to improve or resolve issues with SAM, in some embodiments, leaflet motion may be desirably restricted or immobilized from ablation, necrosis, or increased chordal support via induction of a contractile tissue response on the surrounding native anatomy.

Figure 26B:
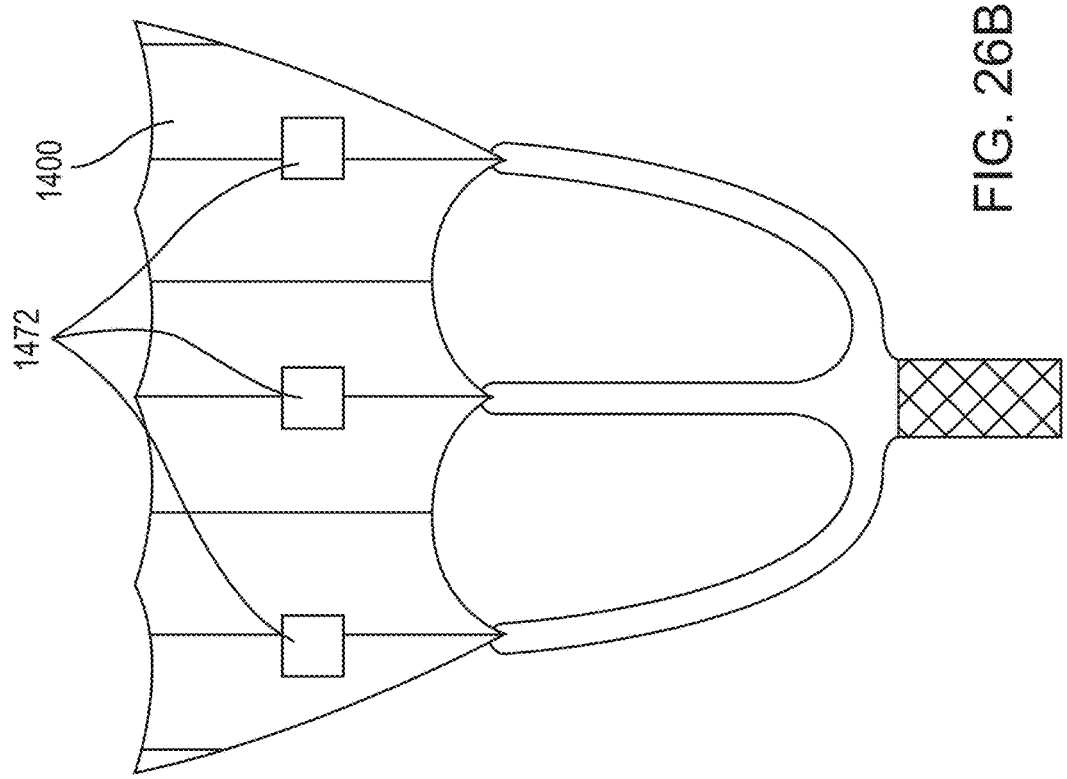
FIG. 26B is a side view of the prosthetic heart valve of FIG. 26A.
Figure 26A:
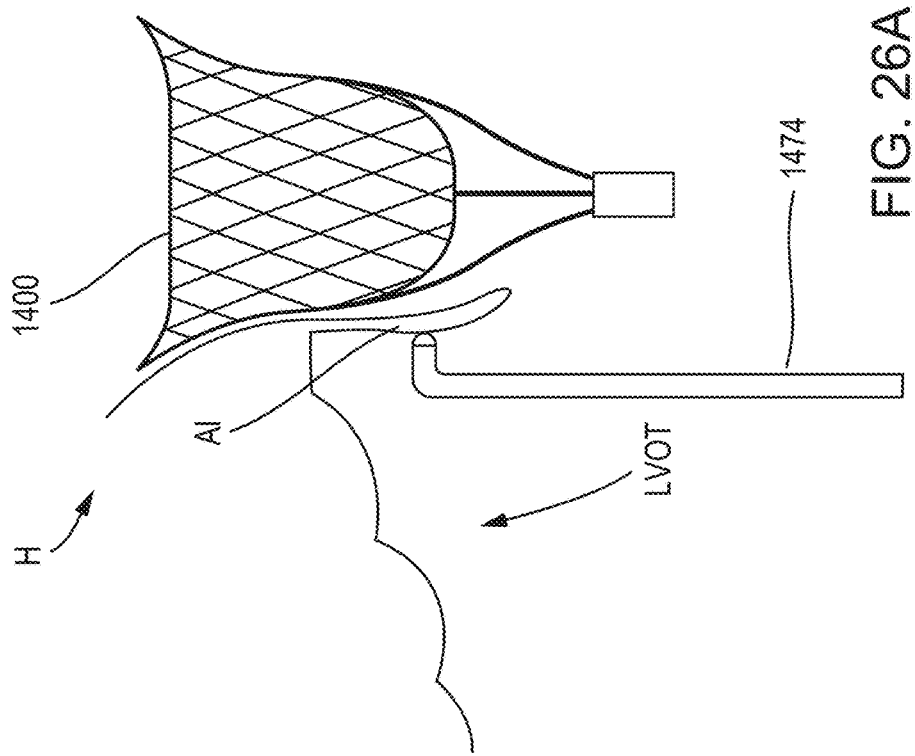
FIG. 26A is a cross-sectional front view of a heart having an ablation catheter disposed therein and a prosthetic heart valve implanted therein, according to an embodiment.

FIG. 26A illustrates in front view a prosthetic heart valve 1400 configured for ablation procedures, according to an embodiment. As shown, the prosthetic heart valve 1400 includes tissue receiving portions 1472. The tissue receiving portions 1472 are configured to receive and engage with a portion of a native leaflet in connection with an ablation procedure. The tissue receiving portions 1472 can be at least partially radiopaque (e.g., a border or perimeter of each tissue receiving portion 1472 can be radiopaque) to promote ease of orientation of the prosthetic valve 1400 and suitable ablation of the valve to the native leaflet. In some embodiments, a method includes, subsequent to implantation of the prosthetic heart valve 1400, attachment of a native leaflet to a portion of the prosthetic heart valve 1400. FIG. 26B illustrates such an embodiment and shows in cross-sectional side view a portion of a heart having an ablation catheter 1474 disposed therein and the prosthetic heart valve 1400 of FIG. 26A implanted therein. The prosthetic heart valve 1400 can be constructed the same as or similar to the prosthetic valves described above (e.g., prosthetic valve 200), and can function in a similar manner.

As illustrated by FIG. 26B, with the prosthetic valve 1400 implanted and seated within the native annulus of the heart H, the ablation catheter 1474 can be used to attach (e.g., weld) a native A2 mitral valve leaflet A1 to a side portion of the prosthetic valve 1400, i.e., by applying energy from the ablation catheter 1474 to the native leaflet A1 at or near the tissue receiving portions 1472 of the prosthetic valve 1400. Utilizing the tissue receiving portions 1472 may promote repeatable and suitable attachment and securement of the native leaflet A1 to the prosthetic valve 1400. In this manner, as shown in FIG. 26B, the native leaflet A1 can be positioned away from the LVOT, thereby limiting and/or preventing LVOT obstruction or SAM. Further, in some embodiments, to promote suitable and strong adhesion or coupling of the native leaflet to the prosthetic valve, tissue (e.g., porcine tissue) can be attached or applied to a portion (e.g., the A2 portion) of the outer surface of the prosthetic valve. For example, one or more patches of porcine tissue can be placed on the tissue receiving portions of the prosthetic valve.

Figure 27:
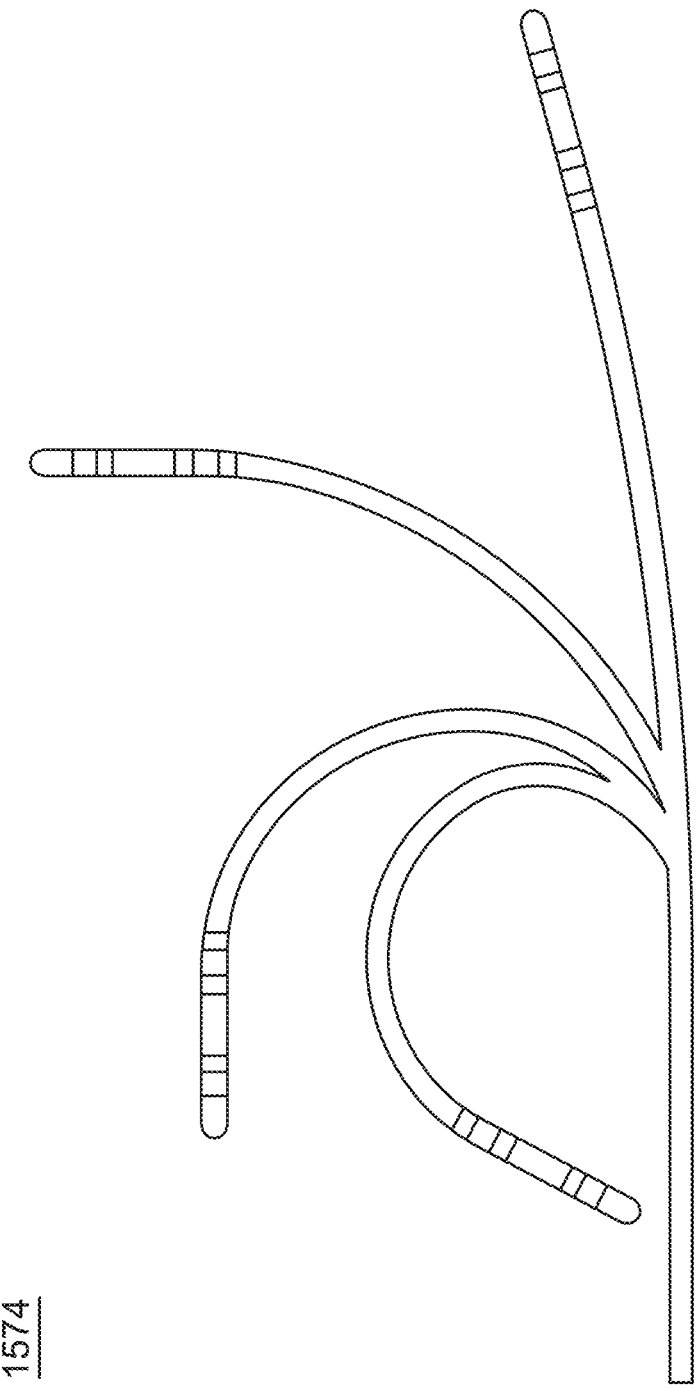
FIG. 27 illustrates an articulating radiofrequency (RF) catheter, in various configurations, according to an embodiment.

In some ablation embodiments, methods include using an articulating single electrode catheter to approximate a native valve leaflet against a prosthetic heart valve. FIG. 27 illustrates an exemplary articulating RF catheter 1574, in various orientations. In some instances, with the native leaflet approximated against the prosthetic valve, the articulating single electrode catheter can deliver RF energy to fuse or secure the mating surfaces (i.e., the leaflet and the valve) together (e.g., similar to procedures that involve sealing or cauterizing vasculature for hemostasis).

Figure 28:
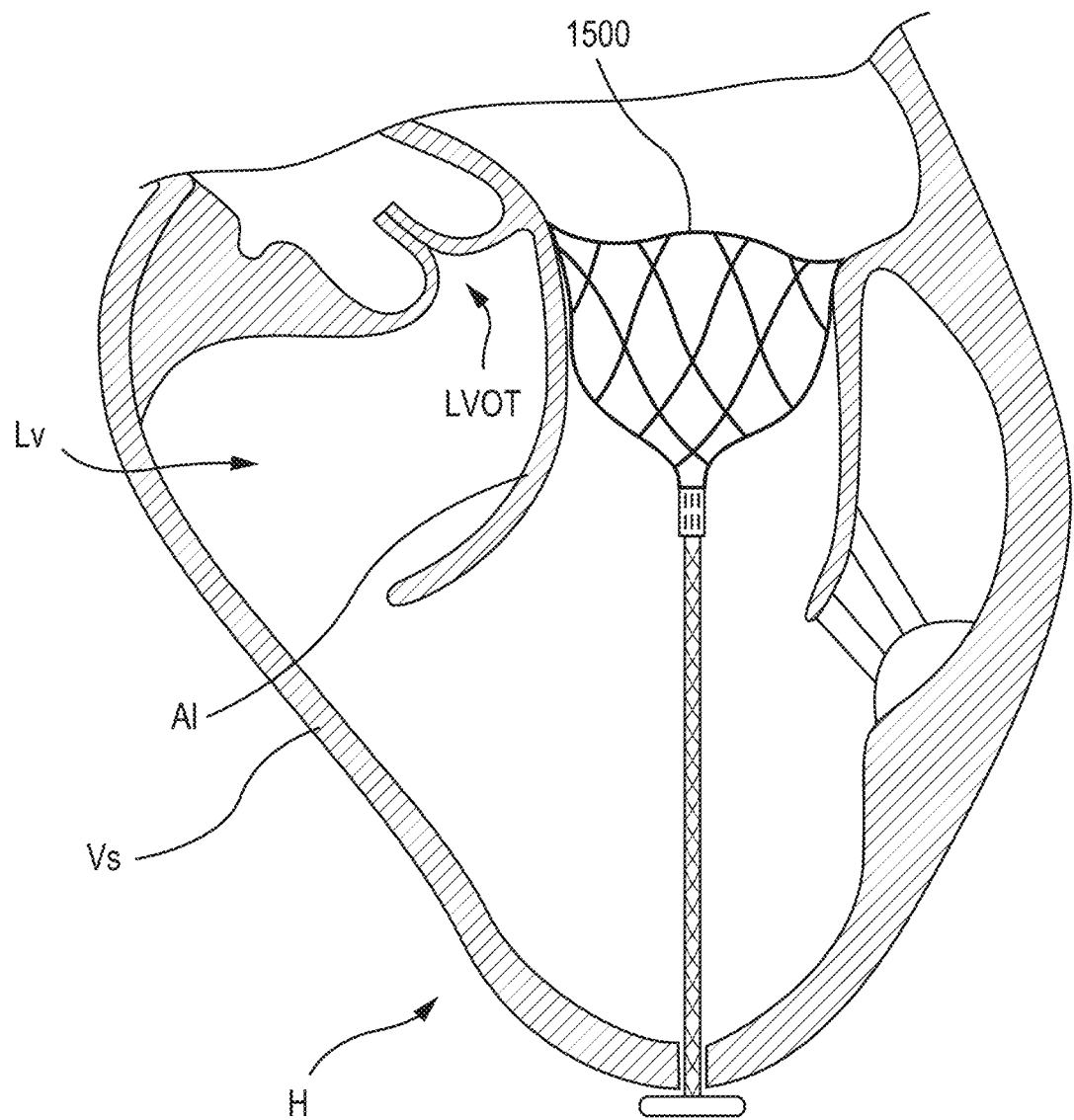
FIG. 28 is a cross-sectional front view of a heart having a prosthetic heart valve implanted therein, and a native anterior valve leaflet disposed within the LVOT, according to an embodiment.

In some embodiments, a stent can be delivered and deployed within a left ventricle of a heart to limit or prevent LVOT obstruction. With the stent implanted and radially expanded within the left ventricle, the stent creates and/or expands a passageway in the LVOT, and limits or prevents the native A2 leaflet from occluding the passageway. FIG. 28 illustrates a cross-sectional front view of a heart H having a prosthetic heart valve 1500 implanted therein, and a native anterior valve leaflet A1 disposed partially within the LVOT; and FIG. 29 illustrates a cross-sectional front view of the heart H and the prosthetic heart valve 1500 of FIG. 28, including an LVOT stent 1584 implanted therein and configured to limit or prevent LVOT obstruction by the native anterior valve leaflet A1, according to an embodiment.

The prosthetic heart valve 1500 can be constructed the same as or similar to, and function the same as or similar to any of the prosthetic heart valves discussed with respect to previous embodiments. Thus, some details regarding the prosthetic heart valve 1500 are not described below. As shown by FIG. 28, with the prosthetic heart valve 1500 implanted within the heart H, the native anterior leaflet A1 may undesirably obstruct at least a portion of the LVOT, as discussed with respect to previous embodiments. To limit or prevent such LVOT obstruction, in this embodiment, as shown by FIG. 29, the LVOT stent 1584 is delivered and deployed within the left ventricle Lv of the heart H. The LVOT stent 1584 can be delivered via any suitable approach, e.g., a femoral approach, an aortic approach, or an apical approach. The LVOT stent 1584 has a biased expanded configuration and can be manipulated and/or deformed (e.g., compressed and/or constrained) and, when released, return to its original unconstrained shape. The LVOT stent 1584 is delivered to the heart in its deformed shape, and is then released within the left ventricle Lv and allowed to radially expand, thereby creating and/or expanding a passageway in the LVOT, and limiting and/or preventing the native anterior leaflet A1 from obstructing the passageway. More specifically, the LVOT stent 1584 radially expands between the ventricular septum Vs and the anterior leaflet A1 (and the prosthetic valve 1500). As shown in FIG. 29, the LVOT stent 1584 biases the anterior leaflet A1 towards and against the prosthetic valve 1500. In this manner, the LVOT stent 1584 and the prosthetic valve 1500 are configured to collectively immobilize the anterior leaflet A1 in a position away from the LVOT, thereby limiting or preventing complications due to LVOT obstruction and/or SAM.

Figure 29:
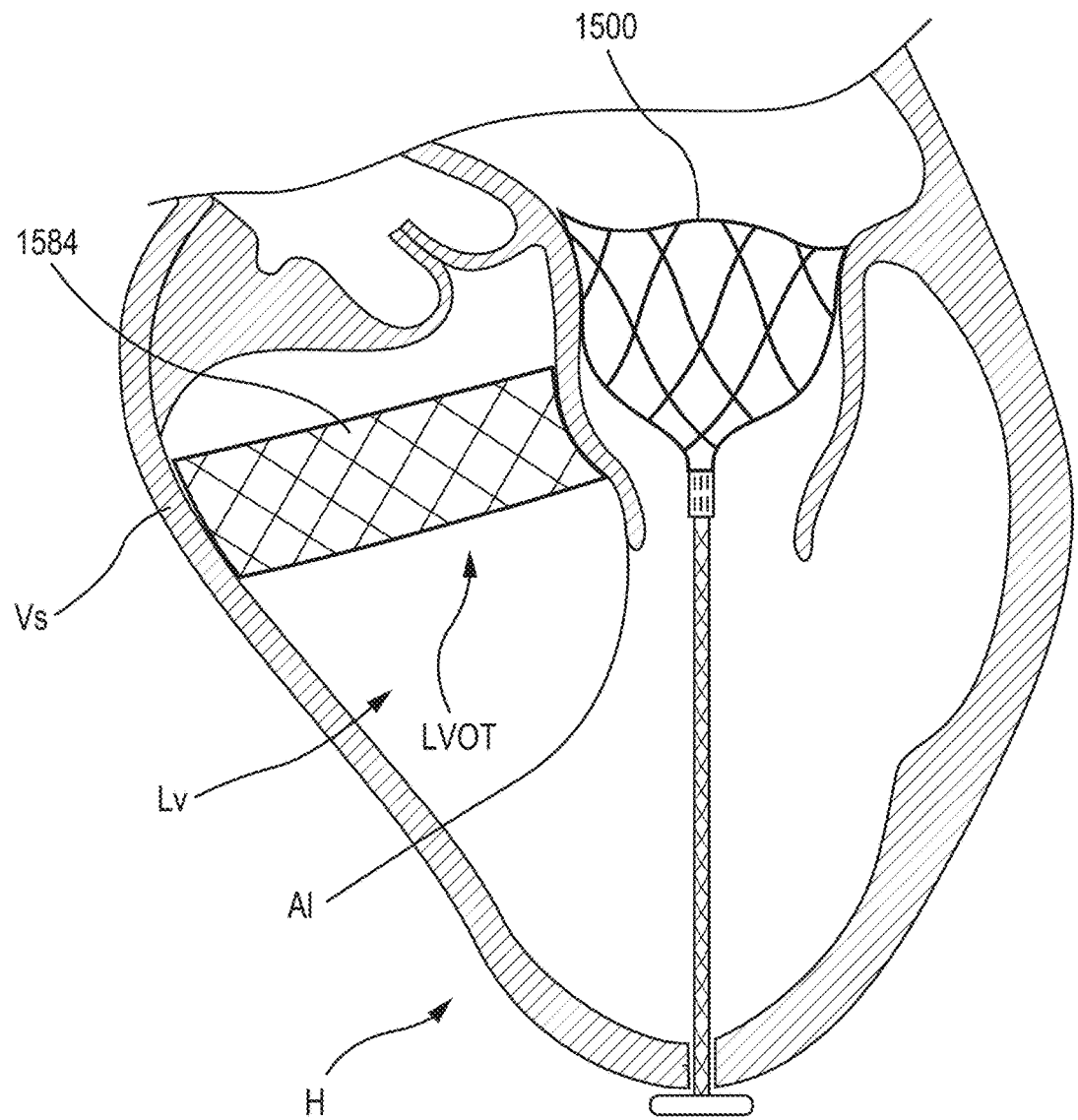
FIG. 29 is a cross-sectional front view of the heart and prosthetic heart valve of FIG. 28, including an LVOT stent implanted therein, according to an embodiment.
Figure 30:
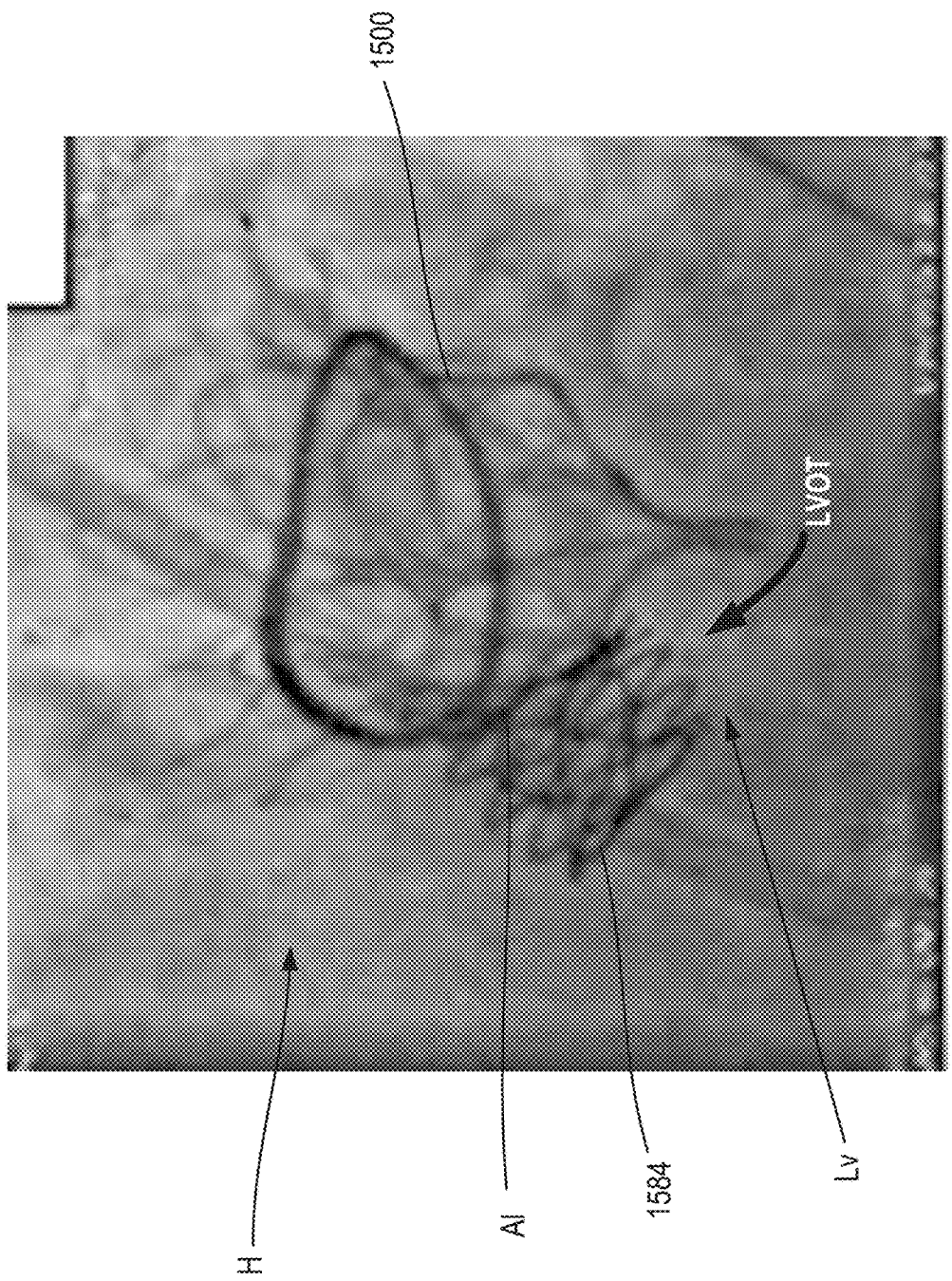
FIG. 30 is a fluoroscopic image of the LVOT stent of FIG. 28 implanted in a heart of a patient.

FIG. 30 illustrates a fluoroscopic image of the LVOT stent 1584 of FIG. 29 implanted in a heart of a patient. As shown, the LVOT stent 1584 is radially expanded in the left ventricle Lv of the heart H such that the anterior leaflet A1 is biased into a position between the LVOT stent 1584 and the prosthetic heart valve 1500 and away from the LVOT. In this manner, the LVOT stent 1584 and the prosthetic heart valve 1500 collectively limit or prevent the anterior leaflet A1 from obstructing the LVOT.

An LVOT stent can be constructed from any suitable materials, such as metals or plastics that have shape memory properties. In this embodiment, as shown best in FIG. 30, the LVOT stent 1584 is constructed from Nitinol®. In other embodiments, other shape memory allows, such as Cu—Zn—Al—Ni alloys, and Cu—Al—Ni alloys, may also be used. In some embodiments, balloon expandable material such as stainless steel or cobalt chromium may be used. Multiple sizes (e.g., length, thickness, diameter), optionally including tapers, could be produced such that a user can select a particular size that is suitable for a particular patient's anatomy. Further, LVOT stents can be customized according to a particular patient's anatomy.

Figure 31:
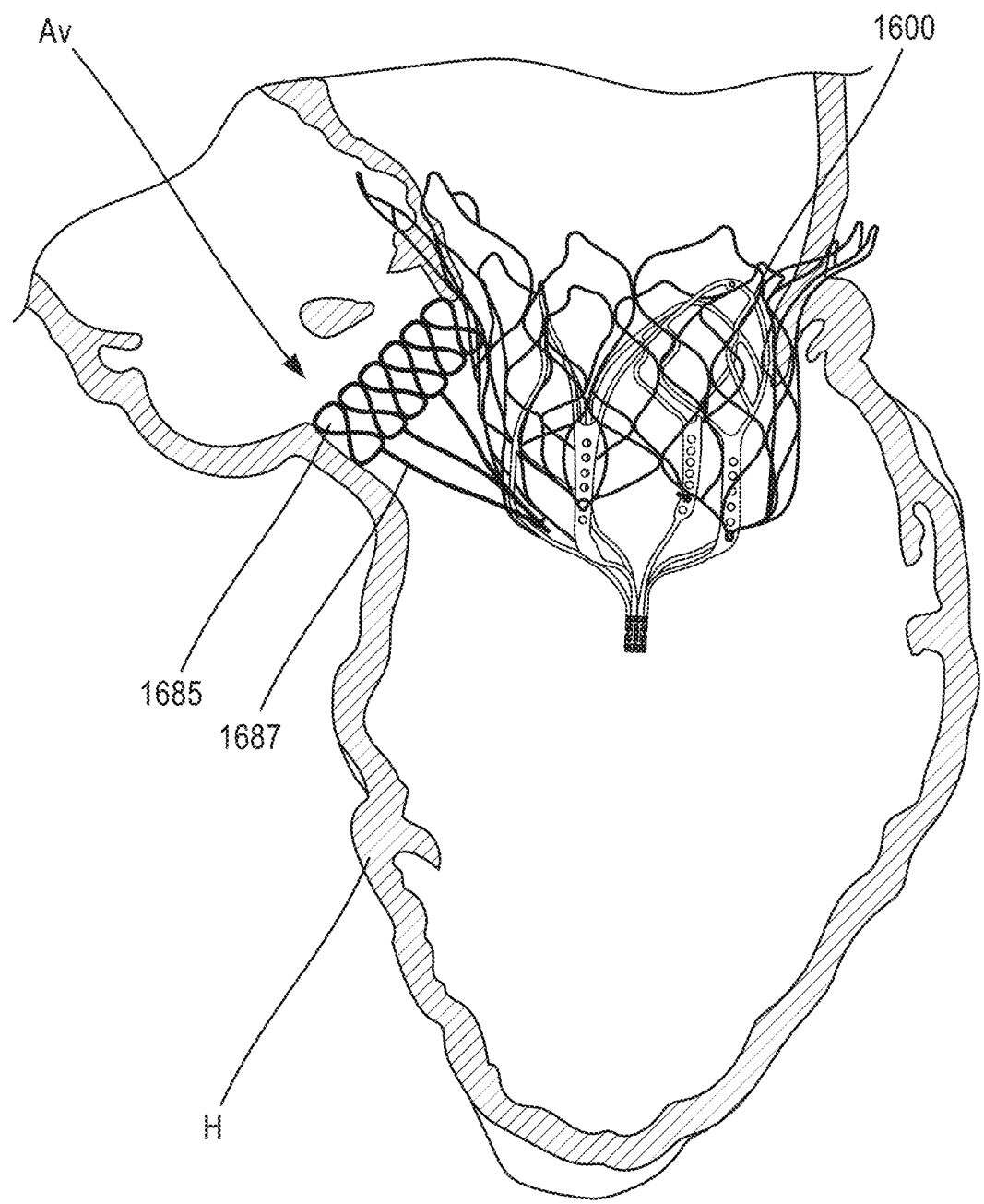
FIG. 31 is a cross-sectional front view of a heart and a prosthetic heart valve implanted therein, and an LVOT stent implanted therein, according to an embodiment.

In some embodiments, an LVOT stent can be deployed and implanted adjacent to or immediately below the aortic valve of a heart, and can include an elongate member extending from near the aortic valve to a portion of an implanted prosthetic mitral valve. FIG. 31 illustrates such an embodiment. As shown in FIG. 31, the LVOT stent 1685 is implanted immediately below the aortic valve Av of the heart H, and adjacent to an implanted prosthetic mitral valve 1600. With the LVOT stent 1685 disposed immediately below the aortic valve Av, an elongate member 1687 of the LVOT stent 1685 extends towards the prosthetic valve 1600. In this manner, the elongate member 1687 biases the anterior leaflet (not shown) towards and into contact with the prosthetic valve 1600 and away from the LVOT. Similarly stated, the elongate member 1687 and the prosthetic valve 1600 are configured to collectively restrain or immobilize the anterior leaflet away from the LVOT, thereby limiting or preventing undesirable LVOT obstruction by the anterior leaflet. Thus, the LVOT stent 1687 can both radially expand near the aortic valve, thereby expanding or supporting a passageway in the LVOT, and restrain the anterior leaflet (using the elongate member 1687 of the LVOT stent 1685) away from the LVOT.

Because an LVOT stent can be formed separately from a prosthetic valve, an LVOT stent can be implanted with various prosthetic valves, and can be implanted when necessary, e.g., to treat occurrence of SAM. In some embodiments, an LVOT stent can be coupled to or covered in a material (e.g., a fabric) for purposes of tissue ingrowth.

Figure 32:
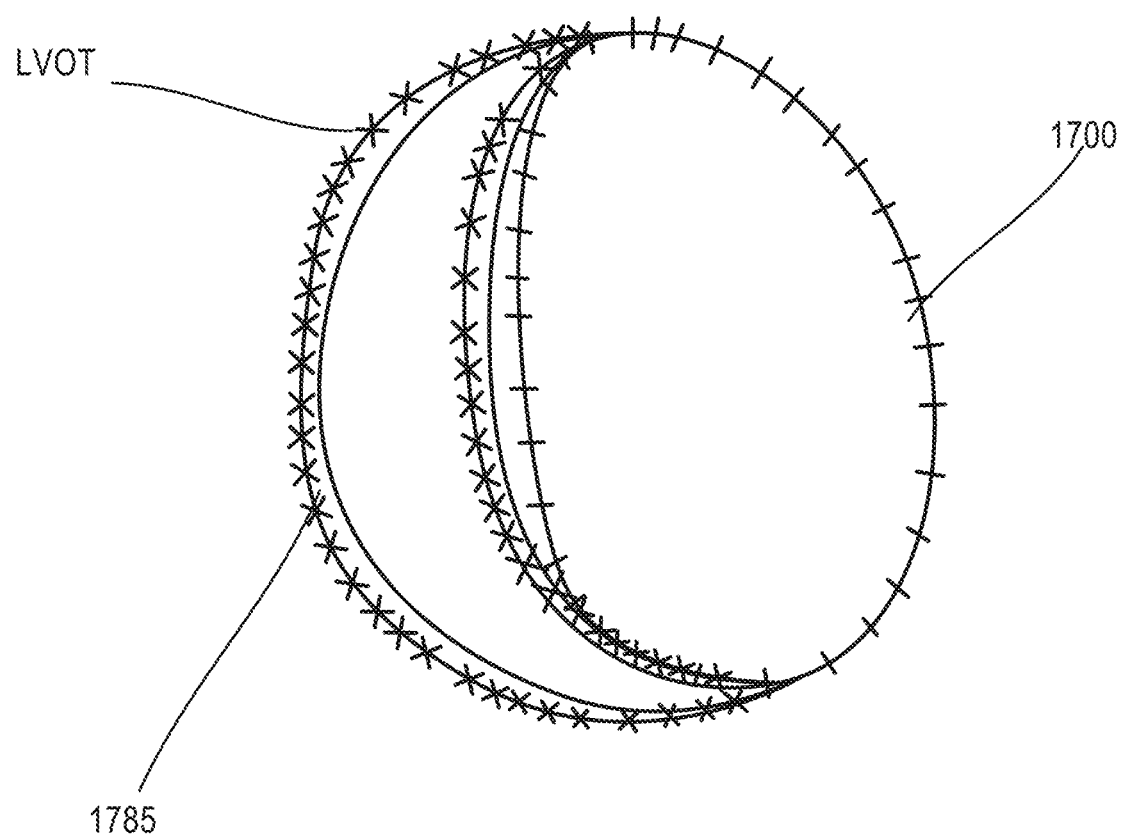
FIG. 32 is a perspective view of an LVOT basket, according to an embodiment.

In some embodiments, it is necessary to capture and/or isolate a native anterior leaflet. A variety of remote grasping apparatus may be employed to capture or isolate the leaflet. In some embodiments, a method can include a kissing balloon technique in the LVOT to bias and position the leaflet into opposition with the prosthetic valve body. In some embodiments, a basket (e.g., formed of Nitinol®; un-balloon) can be delivered and deployed to bias the leaflet away from the LVOT and preserve blood flow through the aorta. For example, FIG. 32 illustrates in a top view (a plane just below the mitral annulus), a LVOT distal protection basket 1785 implanted within the LVOT and adjacent to a prosthetic mitral valve 1700 implanted within the native mitral valve annulus. The basket 1785 can be shaped to match the LVOT and prosthetic mitral valve 1700. As with previous embodiments, the basket 1785 biases the anterior leaflet (not shown) towards and into contact with the prosthetic valve 1700 and away from the LVOT. In yet further embodiments, surgical suction can be employed to enable benign leaflet capture prior to adjunctive leaflet management. Further, various methods to access the heart can be used, e.g., an apical approach, a femoral retrograde approach, a trans-septal approach, etc. In some embodiments, the heart may be selectively paced to temporarily minimize leaflet mobility to facilitate leaflet capture and/or selective alteration of the leaflet and/or surrounding anatomy.

In some embodiments, a native leaflet reversal method can include detaching a native anterior mitral valve leaflet from one or more native tendineae chordae. By untethering or decoupling the native leaflet, the anterior leaflet is at least partially released and allowed to prolapse into the left atrium of the heart, and away from the LVOT. Such a procedure may, in some embodiments, be performed prior to prosthetic valve implantation (e.g., when SAM is anticipated). Detachment of the native leaflet can be accomplished by cutting or severing the tendineae chordae. In some embodiments, following such detachment, the native leaflet may be temporarily or permanently tethered or pinned in the atrium. With the native leaflet secured in the atrium, a prosthetic heart valve can be delivered and deployed, similar to as described with respect to previous embodiments. With the prosthetic heart valve properly seated in the native mitral annulus, the prosthetic valve may function to prevent the native leaflet from entering the left ventricle, and in turn, the LVOT. In some embodiments, the leaflet pins or tethers could be optionally removed.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components, and/or features of the different embodiments described.

What is claimed is:

1. A method, comprising:
   delivering to a mitral valve annulus of a heart a prosthetic heart valve having a body expandable from a collapsed, delivery configuration to an expanded, deployed configuration;
   after the delivering, causing the prosthetic heart valve to move from the delivery configuration to the deployed configuration;
   delivering and securing an anchor to at least one of a fibrous trigone of the heart or an anterior native leaflet of the mitral valve; and
   with the prosthetic heart valve disposed in the mitral valve annulus and in its deployed configuration, securing an anchoring tether extending from the anchor to a wall of the heart to urge the anterior native leaflet towards the body of the prosthetic heart valve.

2. The method of claim 1,
   wherein the securing the anchoring tether includes coupling an epicardial pad device to the anchoring tether and securing the epicardial pad device to an apex region of the heart.

3. The method of claim 1, wherein the securing the anchoring tether includes securing the anchoring tether extending from the anchor to the wall of the heart such that the anterior native leaflet is urged away from a left ventricular outflow tract (LVOT) of the heart.

4. The method of claim 1, wherein the securing the anchoring tether includes securing the anchoring tether extending from the anchor to the wall of the heart such that the anterior native leaflet is immobilized relative to the body of the prosthetic heart valve.

5. The method of claim 1, wherein the anchor is a first anchor and the anchoring tether is a first anchoring tether, the method further comprising:
   delivering and securing a second anchor to at least one of the anterior native leaflet or the fibrous trigone of the heart; and
   with the prosthetic heart valve disposed in the mitral valve annulus and in its deployed configuration, securing a second anchoring tether extending from the second anchor to the wall of the heart to urge the anterior native leaflet of the mitral valve towards the body of the prosthetic heart valve.

6. The method of claim 1, wherein:
   the securing the anchoring tether includes applying tension on the anchoring tether to modify a geometry of the mitral valve annulus.

7. The method of claim 1, wherein:
   the anchor includes at least one of a helix coil shape or an expandable barb.

8. The method of claim 1, wherein:
   the securing the anchor includes securing the anchor to a free-end portion of the anterior native leaflet.

9. The method of claim 1, wherein:
   the securing the anchor includes securing the anchor to a hinge-point portion of the anterior native leaflet.

* * * * *